US009034855B2

(12) United States Patent
Fürstner et al.

(10) Patent No.: US 9,034,855 B2
(45) Date of Patent: May 19, 2015

(54) SUBSTITUTED PHENYLACETATE AND PHENYLPROPANE AMIDES AND USE THEREOF

(75) Inventors: Chantal Fürstner, Mülheim/Ruhr (DE); Joerg Keldenich, Wuppertal (DE); Martina Delbeck, Heiligenhaus (DE); Peter Kolkhof, Wuppertal (DE); Axel Kretschmer, Wuppertal (DE); Elisabeth Pook, Wuppertal (DE); Carsten Schmeck, Mülheim (DE); Hubert Trübel, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 33 days.

(21) Appl. No.: 13/819,885

(22) PCT Filed: Sep. 14, 2011

(86) PCT No.: PCT/EP2011/065961
§ 371 (c)(1),
(2), (4) Date: Apr. 19, 2013

(87) PCT Pub. No.: WO2012/035075
PCT Pub. Date: Mar. 22, 2012

(65) Prior Publication Data
US 2013/0231313 A1  Sep. 5, 2013

(30) Foreign Application Priority Data
Sep. 16, 2010 (DE) .......................... 10 2010 040 924

(51) Int. Cl.
*C07D 249/12* (2006.01)
*C07D 409/04* (2006.01)
*A61K 31/4196* (2006.01)
*A61K 45/06* (2006.01)

(52) U.S. Cl.
CPC .......... *A61K 31/4196* (2013.01); *C07D 249/12* (2013.01); *C07D 409/04* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,276,049 A | 1/1994 | Himmelsbach et al. |
| 5,281,614 A | 1/1994 | Ashton et al. |
| 5,326,776 A | 7/1994 | Winn et al. |
| 5,468,448 A | 11/1995 | Nicolson et al. |
| 5,585,394 A | 12/1996 | Di Malta et al. |
| 5,681,841 A | 10/1997 | Himmelsbach et al. |
| 6,469,012 B1 | 10/2002 | Ellis et al. |
| 6,531,142 B1 | 3/2003 | Rabe et al. |
| 6,693,102 B2 | 2/2004 | Stasch et al. |
| 6,743,798 B1 | 6/2004 | Straub et al. |
| 6,746,989 B1 | 6/2004 | Müller et al. |
| 6,762,152 B1 | 7/2004 | Müller et al. |
| 6,833,364 B1 | 12/2004 | Straub et al. |
| 6,838,415 B1 | 1/2005 | Müller et al. |
| 6,864,287 B1 | 3/2005 | Alonso-Alija et al. |
| 6,924,251 B1 | 8/2005 | Schwarz et al. |
| 6,969,697 B2 | 11/2005 | Muller et al. |
| 7,080,644 B2 | 7/2006 | Gumaste |
| 7,173,037 B2 | 2/2007 | Alonso-Alija et al. |
| 7,279,444 B2 | 10/2007 | Muller et al. |
| 7,642,275 B2 | 1/2010 | Bressi et al. |
| 7,674,825 B2 | 3/2010 | Alonso-Alija et al. |
| 8,084,481 B2 | 12/2011 | Meier et al. |
| 2001/0020100 A1 | 9/2001 | Manning et al. |
| 2002/0045651 A1 | 4/2002 | Brenner et al. |
| 2002/0172644 A1 | 11/2002 | Haslwanter et al. |
| 2003/0161790 A1 | 8/2003 | Wahi et al. |
| 2004/0071757 A1 | 4/2004 | Rolf et al. |
| 2004/0082798 A1 | 4/2004 | Alonso-Alija et al. |
| 2004/0176446 A1 | 9/2004 | Alonso-Alija et al. |
| 2006/0148779 A1 | 7/2006 | Bell et al. |
| 2007/0225333 A1 | 9/2007 | Bryans et al. |
| 2007/0281937 A1 | 12/2007 | Zelle et al. |
| 2008/0058314 A1 | 3/2008 | Alonso-Alija et al. |
| 2008/0139560 A1 | 6/2008 | Zelle et al. |
| 2010/0261771 A1 | 10/2010 | Bruggemeier et al. |
| 2011/0245308 A1 | 10/2011 | Bruggemeier et al. |
| 2012/0053218 A1 | 3/2012 | Brüggemeier et al. |
| 2012/0208852 A1 | 8/2012 | Furstner et al. |
| 2012/0238607 A1 | 9/2012 | Brüggemeier et al. |
| 2013/0225646 A1 | 8/2013 | Fürstner et al. |

FOREIGN PATENT DOCUMENTS

| | | |
|---|---|---|
| EP | 0051829 | 5/1982 |
| EP | 0412594 | 7/1990 |

(Continued)

OTHER PUBLICATIONS

Horig, H., Pullman, W. From bench to clinic and back: Perspective on the 1st IPQC Translational Research Conference. Journal of Translational Medicine. Dec. 2004, 2, 44.*
Schafer, S., Kolkhof, P. Failure is an option: learning from unsuccessful proof-of-concept trials. Drug Discovery Today. Nov. 2008, 13, 913-916.*
Verbalis, J. G. AVP receptor antagonists as aquaretics: Review and assessment of clinical data. Cleveland Clinic Journal of Medicine. Sep. 2006, 73, S24-S33.*
Chang et al., Triazolinones as Nonpeptide Angiotensin II Antagonists. 1. Synthesis and Evaluation of Potent 2, 4, 5-Trisubstituted Triazoloinones, J. Med. Chem. 1993, vol. 36, Nr. 17, 2558-2568.

(Continued)

*Primary Examiner* — Alicia L Otton
(74) *Attorney, Agent, or Firm* — Karen B. King

(57) ABSTRACT

The present application relates to novel substituted phenylacetamides and phenylpropanamides, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

8 Claims, No Drawings

(56) References Cited

FOREIGN PATENT DOCUMENTS

| EP | 0533276 | 3/1993 |
|---|---|---|
| WO | 9931099 | 6/1999 |
| WO | 0100595 | 1/2001 |
| WO | 0119355 | 3/2001 |
| WO | 02066447 | 8/2002 |
| WO | 2006117657 | 11/2006 |
| WO | 2011104322 | 9/2011 |

OTHER PUBLICATIONS

Dobosz et al., "Synthesis and Some Pharmacological Properties of 3-(4-phenyl-5-oxo-1,2,4-triazolin-1-ylmethyl)-1,2,-triazolin-5-thione Derivatives," Acta Polomiae Pharmaceutica 2002, vol. 59, No. 4, 281-290.

Verbalis, J.G., "AVP receptor antagonists as aquaretics: Review and assessment of clinical data," Cleveland Clinic Journal of Medicine, Sep. 2009, 73, S24-S33.

Finley, et al., "Arginine Vasopressin Antagonists for the Treatment of Heart Failure and Hyponatremia," Circulation 2008, 118:410-421, p. 412, col. 2.

Gines, P. et al., "Effects of stavaptan, a selective vasopressin V2 receptor antagonist, on ascites and serum sodium cirrhosis with hyponatremia," Hepatology, 2008, 48(1):204-212.

Goldsmith, et al., "Current treatments and novel pharmacologic treatments for hyponatremia in congestive heart failure," Am. J. Cardiol, 2005, 95(suppl): 14B-23B.

Patani, et al.: "Bioisosterism: A Rational Approach in Drug Design," Chem. Rev., 1996, 96:3147-3176.

Schrier, Robert W., The sea within us: Disorders of body water homeostasis, Current Opinion in Investigational Drugs, 2007, 8(4):304-311.

Bronson, et al.,:"Discovery of the First Antibactrial Small Molecule Inhibitors of MurB," Bioorganic & Medicinal Chemistry Letters, 2003, 13: 873-875.

DeLuca, et al.,:"Hyponatremia in Paitents with Heart Failure," Am. J. Cardiol., 2005, vol. 96 (suppl.), 19L-23L.

Francis, et al.:"Comparison of Neuroendocrine Activation in Patients with Left Ventricular Dysfunction with and without Congestive Heart Failure," Circulation, Nov. 1990, 82(5): 1724-1729.

Lemmens-Gruber, et al.:"Vasopressin Antagonists," Cell. Mol. Life Sci., 2006, 63:1766-1779.

Palm, et al.:"Vasopressin Antagonists as Aquaretic Agents for the Treatment of Hyponatremia," Am. J. Med., 2006, 119(7A): S87-S92.

Saghi, et al.:"Vasopressin Antagonism: A Future Treatment Option in Heart Failure," Europ. Heart J., 2005, 26: 538-543.

Schrier, et al.:"Hormones and Hemodynamics in Heart Failure," New Engl. J. Med., Aug. 19, 1999, 341(8): 577-585.

Tang, et al.:"Vasopressin Receptor Antagonists in the Management of Acute Heart Failure," Expert Opin. Investig. Drugs, 2005, 14(5): 593-600.

Hassan et al., "Aryl-Aryl Bond Formation One Century after the Discovery of the Ulmann Reaction," Chem Rev 2002, 102:1359-1469.

Arnswald, et al., "Unconventional Regiospecific Synthesis of Aromatic Carbonamides and Thiocarbonamides by Means of Tin-Mediated Friedel-Crafts Reactions." J. Org. Chem., 1993 58(25): 7022-7028.

Papadopoulos et al.,"Friedel-Crafts Thioacylation with Ethoxycarbonyl Isothiocyanate: A One-Step Synthesis of Aromatic Thioamides," J. Org. Chem 1976, 41(6): 962-965.

* cited by examiner

SUBSTITUTED PHENYLACETATE AND PHENYLPROPANE AMIDES AND USE THEREOF

The present application relates to novel substituted phenylacetamides and phenylpropanamides, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

The liquid content of the human body is subject to various physiological control mechanisms whose purpose is to keep it constant (volume homeostasis). In the process, both the volume filling of the vascular system and also the osmolarity of the blood plasma are continuously recorded by appropriate sensors (baroreceptors and osmoreceptors). The information which these sensors supply to the relevant centres in the brain regulates drinking behaviour and controls fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurons in the nucleus supraopticus and n. para-ventricularis in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatraemia (sodium concentration <135 mmol/L); it is the most important electrolyte abnormality in hospital patients, with an incidence of about 5% or 250 000 cases per year in the USA alone. If the plasma sodium concentration falls below 115 mmol/L, comatose states and death are imminent.

Depending on the underlying cause, a distinction is made between hypovolaemic, euvolaemic and hypervolaemic hyponatraemia. The forms of hypervolaemia with oedema formation are clinically significant. Typical examples of this are the syndrome of inadequate ADH/vasopressin secretion (SIAD) (e.g. after craniocerebral trauma or as paraneoplasia in carcinomas) and hypervolaemic hyponatraemia in liver cirrhosis, various renal diseases and heart failure [De Luca L. et al., *Am. J. Cardiol.* 96 (suppl.), 19L-23L (2005)]. In particular, patients with heart failure, in spite of their relative hyponatraemia and hypervolaemia, often display elevated vasopressin levels, which is seen as the consequence of generally disturbed neurohumoral regulation in heart failure [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavourable haemodynamic consequences associated therewith in terms of increased backload, the emptying of the left ventricle, the pressure in the pulmonary blood vessels and cardiac output are also adversely affected by V1a-mediated vasoconstriction.

Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of heart failure. In particular, compounds with combined activity on both vasopressin receptors (V1a and V2) should both have desirable renal and also haemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle hypertrophy, could be further intensified [Saghi P. et al., *Europ. Heart J.* 26, 538-543 (2005)].

WO 99/54315 discloses substituted triazolones having neuroprotective action, and WO 2006/117657 describes triazolone derivatives as antiinflammatory agents. Furthermore, EP 503 548-A1 and EP 587 134-A2 claim cyclic urea derivatives and their use for the treatment of thromboses. Substituted triazolthiones as ion channel modulators are disclosed in WO 2005/097112. WO 2007/134862 describes substituted imidazol-2-ones and 1,2,4-triazolones as vasopressin receptor antagonists for the treatment of cardiovascular disorders. Variously substituted triazolones as vasopressin receptor antagonists are disclosed in WO 2010/105770, WO 2010/105750, WO 2011/104322 and WO 2011/023703.

It was an object of the present invention to provide novel compounds which act as potent selective, dual V1a/V2 receptor antagonists and have increased solubility in aqueous media, and as such are suitable for the treatment and/or prevention of diseases, more particularly for the treatment and/or prevention of cardiovascular disorders.

The present invention provides compounds of the general formula (I)

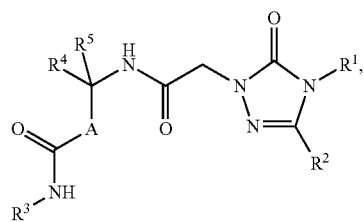

in which
A represents a bond or $C(R^{6A}R^{6B})$—,
where
$R^{6A}$ represents hydrogen, $(C_1-C_4)$-alkyl or trifluoromethyl,
$R^{6B}$ represents hydrogen or $(C_1-C_4)$-alkyl,
$R^1$ represents $(C_1-C_6)$-alkyl, $(C_2-C_6)$-alkenyl, $(C_2-C_6)$-alkynyl or $(C_3-C_7)$-cycloalkyl,
where $(C_1-C_6)$-alkyl, $(C_2-C_6)$-alkenyl and $(C_2-C_6)$-alkynyl may be substituted by 1 to 3 substituents independently of one another selected from the group consisting of deuterium, halogen, cyano, oxo, hydroxy, trifluoromethyl, $(C_3-C_7)$-cycloalkyl, $(C_1-C_6)$-alkoxy, trifluoromethoxy and phenyl,
in which $(C_3-C_7)$-cycloalkyl may be substituted by 1 or 2 substituents independently of one another selected from the group consisting of $(C_1-C_4)$-alkyl, oxo, hydroxy, $(C_1-C_4)$-alkoxy and amino,
and
in which $(C_1-C_6)$-alkoxy may be substituted by 1 or 2 substituents independently of one another selected from the group consisting of amino, hydroxy, $(C_1-C_4)$-alkoxy, hydroxycarbonyl and $(C_1-C_4)$-alkoxycarbonyl
and
in which phenyl may be substituted by 1 to 3 substituents independently of one another selected from the group consisting of halogen, cyano, nitro, $(C_1-C_4)$-alkyl, trifluoromethyl, hydroxy, hydroxymethyl, $(C_1-C_4)$-alkoxy, trifluoromethoxy, $(C_1-C_4)$-alkoxymethyl, hydroxycarbonyl, $(C_1-C_4)$-alkoxycarbonyl, aminocarbonyl, mono-$(C_1-C_4)$-alkylaminocarbonyl and di-$(C_1-C_4)$-alkylaminocarbonyl,
and
where $(C_3-C_7)$-cycloalkyl may be substituted by 1 or 2 substituents independently of one another selected from the group consisting of fluorine, $(C_1-C_4)$-alkyl, $(C_1-C_4)$-alkoxy, hydroxy, amino and oxo, $R^2$ represents benzothienyl, phenyl, thienyl or furyl,
where benzothienyl, phenyl, thienyl and furyl may be substituted by 1 to 3 substituents independently of one another selected from the group consisting of halogen, cyano, nitro, $(C_1-C_4)$-alkyl, trifluoromethyl, hydroxy, $(C_1-C_4)$-alkoxy and trifluoromethoxy,
$R^3$ represents a group of the formula

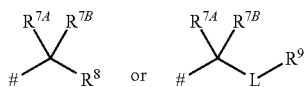

where
# represents the point of attachment to the nitrogen atom,
L represents $(C_1-C_4)$-alkanediyl,
where $(C_1-C_4)$-alkanediyl may be substituted by 1 to 3 substituents independently of one another selected from the group consisting of fluorine and $(C_1-C_4)$-alkyl,
$R^{7A}$ represents hydrogen or $(C_1-C_4)$-alkyl,
$R^{7B}$ represents hydrogen or $(C_1-C_4)$-alkyl,
or
$R^{7A}$ and $R^{7B}$ together with the carbon atom to which they are attached form a 3- to 6-membered carbocycle,
$R^8$ represents hydroxycarbonyl, $(C_1-C_4)$-alkoxycarbonyl, aminocarbonyl, mono-$(C_1-C_4)$-alkylaminocarbonyl or di-$(C_1-C_4)$-alkylaminocarbonyl,
$R^9$ represents hydroxy, trifluoromethoxy, $(C_1-C_4)$-alkoxy, hydroxycarbonyl, $(C_1-C_4)$-alkoxycarbonyl, aminocarbonyl, mono-$(C_1-C_4)$-alkylaminocarbonyl or di-$(C_1-C_4)$-alkylaminocarbonyl,
$R^4$ represents phenyl, naphthyl or 5- to 10-membered heteroaryl, where phenyl, naphthyl and 5- to 10-membered heteroaryl may be substituted by 1 to 3 substituents independently of one another selected from the group consisting of halogen, cyano, nitro, $(C_1-C_4)$-alkyl, difluoromethyl, trifluoromethyl, hydroxy, $(C_1-C_4)$-alkoxy, difluoromethoxy and trifluoromethoxy,
$R^5$ represents hydrogen, deuterium, trifluoromethyl or $(C_1-C_4)$-alkyl,
and their salts, solvates and solvates of the salts.

Compounds according to the invention are the compounds of the formula (I) and their salts, solvates, and solvates of the salts; the compounds of the below-specified formulae embraced by formula (I), and their salts, solvates, and solvates of the salts; and also the compounds specified below as working examples and embraced by formula (I), and their salts, solvates, and solvates of the salts; insofar as the below-specified compounds embraced by formula (I) are not already salts, solvates, and solvates of the salts.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of conventional mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanol-amine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl in the context of the invention is a straight-chain or branched alkyl radical having 1 to 6 or 1 to 4 carbon atoms. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Alkandiyl in the context of the invention represents a straight-chain divalent alkyl radical having 1 to 4 carbon atoms. The following may be mentioned by way of example and by way of preference: methylene, ethane-1,2-diyl, propane-1,3-diyl and butane-1,4-diyl.

Cycloalkyl in the context of the invention is a monocyclic saturated alkyl radical having 3 to 7 or 3 to 6 carbon atoms. The following may be mentioned by way of example and by way of preference: cyclopropyl, cyclobutyl, cyclopentyl, cyclohexyl and cycloheptyl.

Carbocycle in the context of the invention represents a monocyclic saturated alkyl radical having 3 to 6 carbon atoms. The following may be mentioned by way of example and by way of preference: cyclopropyl, cyclobutyl, cyclopentyl and cyclohexyl.

Alkenyl in the context of the invention is a straight-chain or a branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkenyl in the context of the invention is a straight-chain or branched alkynyl radical having 2 to 6 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkoxy in the context of the invention is a straight-chain or branched alkoxy radical having 1 to 6 or 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkoxycarbonyl in the context of the invention is a straight-chain or branched alkoxy radical having 1 to 4 carbon atoms and a carbonyl group attached to the oxygen. By way of example and for preference it includes the following: methoxycarbonyl, ethoxycarbonyl, n-propoxycarbonyl, isopropoxycarbonyl and tert-butoxycarbonyl.

Monoalkylaminocarbonyl in the context of the invention represents an amino group which is attached via a carbonyl group and which has one straight-chain or branched alkyl substituent having 1 to 4 carbon atoms. The following may be mentioned by way of example and by way of preference: methylaminocarbonyl, ethylaminocarbonyl, n-propylaminocarbonyl, isopropyl-aminocarbonyl, n-butylaminocarbonyl and tert-butylaminocarbonyl.

Dialkylaminocarbonyl in the context of the invention represents an amino group which is attached via a carbonyl group and which has two identical or different straight-chain or branched alkyl substituents having 1 to 4 carbon atoms each.

The following may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Heteroaryl in the context of the invention represents a mono- or optionally bicyclic aromatic heterocycle (heteroaromatic) having a total of 5 to 10 ring atoms which contains up to three identical or different ring heteroatoms from the group consisting of N, O and S and is attached via a ring carbon atom or optionally via a ring nitrogen atom. The following may be mentioned by way of example: furyl, pyrrolyl, thienyl, pyrazolyl, imidazolyl, thiazolyl, oxazolyl, isoxazolyl, iso-thiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to three ring heteroatoms from the group consisting of N, O and S such as furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

Halo= in the context of the invention includes fluorine, chlorine, bromine and iodine. Preference is given to chlorine or fluorine.

An oxo group in the context of the invention is an oxygen atom attached via a double bond to a carbon atom.

In the formulae of the groups possible for $R^3$ or $R^4$, the end point of the line where there is a sign # or * does not represent a carbon atom or a CH2 group but forms part of the bond to the atom which is designated in each case and to which $R^3$ and $R^4$, respectively, are attached.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred. Very particular preference is given to substitution by one substituent.

In the context of the present invention, preference is given to compounds of the formula (I) in which
A represents a bond or —C($R^{6A}R^{6B}$)—,
where
$R^{6A}$ represents hydrogen,
$R^{6B}$ represents hydrogen,
$R^1$ represents ($C_1$-$C_6$)-alkyl, ($C_2$-$C_6$)-alkenyl or ($C_3$-$C_6$)-cycloalkyl,
where ($C_1$-$C_6$)-alkyl and ($C_2$-$C_6$)-alkenyl may be substituted by 1 to 3 substituents independently of one another selected from the group consisting of fluorine, chlorine, cyano, oxo, hydroxy, trifluoromethyl, ($C_3$-$C_6$)-cycloalkyl, ($C_1$-$C_4$)-alkoxy, trifluoromethoxy and phenyl,
in which ($C_3$-$C_6$)-cycloalkyl may be substituted by 1 or 2 substituents independently of one another selected from the group consisting of methyl, ethyl, oxo, hydroxy, methoxy, ethoxy and amino,
and
in which phenyl may be substituted by a substituent selected from the group consisting of fluorine, chlorine, cyano, methyl, ethyl, trifluoromethyl, methoxy, ethoxy, trifluoromethoxy, methoxymethyl, ethoxymethyl, hydroxycarbonyl, methoxycarbonyl, ethoxycarbonyl and aminocarbonyl,
and
where ($C_3$-$C_6$)-cycloalkyl may be substituted by 1 or 2 substituents independently of one another selected from the group consisting of fluorine, methyl, ethyl, methoxy, ethoxy, hydroxy, amino and oxo,
$R^2$ represents phenyl or thienyl,
where phenyl and thienyl may be substituted by 1 or 2 substituents independently of one another selected from the group consisting of fluorine, chlorine, bromine, methyl, ethyl, trifluoromethyl, hydroxy, methoxy, ethoxy and trifluoromethoxy,
$R^3$ represents a group of the formula

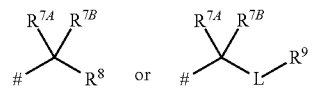

# represents the point of attachment to the nitrogen atom,
L represents methylene,
where methylene may be substituted by 1 or 2 methyl substituents,
$R^{7A}$ represents hydrogen or methyl,
$R^{7B}$ represents hydrogen or methyl,
or
$R^{7A}$ and $R^{7B}$ together with the carbon atom to which they are attached form a cyclopropyl ring,
$R^8$ represents hydroxycarbonyl, methoxycarbonyl, ethoxycarbonyl, aminocarbonyl, methylaminocarbonyl, ethylaminocarbonyl, dimethylaminocarbonyl or diethylaminocarbonyl,
$R^9$ represents hydroxy, trifluoromethoxy, methoxy, ethoxy, hydroxycarbonyl, methoxycarbonyl, ethoxycarbonyl, aminocarbonyl, methylaminocarbonyl, ethylaminocarbonyl, dimethylaminocarbonyl or diethylaminocarbonyl,
$R^4$ represents phenyl,
where phenyl is substituted by 1 to 3 substituents independently of one another selected from the group consisting of fluorine, chlorine, cyano, methyl, ethyl, difluoromethyl, trifluoromethyl, methoxy, difluoromethoxy and trifluoromethoxy,
$R^5$ represents hydrogen or methyl,
and to their salts, solvates and solvates of the salts.

Particular preference in the context of the present invention is given to compounds of the formula (I) in which
A represents a bond or —C($R^{6A}R^{6B}$)—,
where
$R^{6A}$ represents hydrogen,
$R^{6B}$ represents hydrogen,
$R^1$ represents ($C_2$-$C_4$)-alkyl, ($C_2$-$C_4$)-alkenyl or cyclopropyl,
where ($C_2$-$C_4$)-alkyl and ($C_2$-$C_4$)-alkenyl may be substituted by 1 or 2 substituents independently of one another selected from the group consisting of fluorine, oxo, hydroxy and trifluoromethyl,
$R^2$ represents phenyl,
where phenyl is substituted by a substituent selected from the group consisting of fluorine and chlorine,
$R^3$ represents a group of the formula

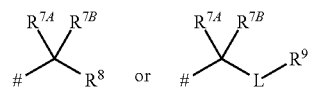

where
# represents the point of attachment to the nitrogen atom,
L represents methylene,
$R^{7A}$ represents hydrogen or methyl,
$R^{7B}$ represents hydrogen or methyl, or $R^{7A}$ and $R^{7B}$ together with the carbon atom to which they are attached form a cyclopropyl ring, $R^8$ represents hydroxycarbonyl, methoxycarbonyl, ethoxycarbonyl or aminocarbonyl, $R^9$ represents hydroxy, methoxy, hydroxycarbonyl, methoxycarbonyl, ethoxycarbonyl or aminocarbonyl, $R^4$ represents a group of the formula

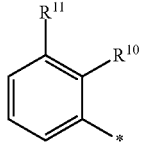

where

\* represents the point of attachment to the group —C($R^5$)(AC(=O)NH$R^3$)—, $R^{10}$ represents hydrogen, chlorine, trifluoromethyl, trifluoromethoxy or methoxy, $R^{11}$ represents hydrogen, fluorine, chlorine, trifluoromethyl, trifluoromethoxy or methoxy, where at least one of the radicals $R^{10}$ and $R^{11}$ is different from hydrogen, $R^5$ represents hydrogen or methyl, and to their salts, solvates and solvates of the salts.

Preference in the context of the present invention is also given to compounds of the formula (I) in which $R^2$ represents p-chlorophenyl, and to their salts, solvates and solvates of the salts.

Preference in the context of the present invention is also given to compounds of the formula (I) in which $R^1$ represents 3,3,3-trifluoroprop-1-en-1-yl, and to their salts, solvates and solvates of the salts.

Preference in the context of the present invention is also given to compounds of the formula (I) in which $R^1$ represents 3,3,3-trifluoropropyl, and to their salts, solvates and solvates of the salts.

Preference in the context of the present invention is also given to compounds of the formula (I) in which $R^1$ represents 1,1,1-trifluoropropan-2-ol-3-yl, and to their salts, solvates and solvates of the salts.

Preference in the context of the present invention is also given to compounds of the formula (I) in which $R^1$ represents ($C_2$-$C_4$)-alkyl or ($C_2$-$C_4$)-alkenyl, where ($C_2$-$C_4$)-alkyl and ($C_2$-$C_4$)-alkenyl are substituted by 1 or 2 substituents independently of one another selected from the group consisting of fluorine, hydroxy, oxo and trifluoromethyl and to their salts, solvates and solvates of the salts.

Preference in the context of the present invention is also given to compounds of the formula (I) in which $R^1$ represents cyclopropyl, and to their salts, solvates and solvates of the salts.

Preference in the context of the present invention is also given to compounds of the formula (I) in which A represents C($R^{6A}R^{6B}$)—, where $R^{6A}$ represents hydrogen, $R^{6B}$ represents hydrogen, and to their salts, solvates and solvates of the salts.

Preference in the context of the present invention is also given to compounds of the formula (I) in which A represents C($R^{6A}R^{6B}$)—, where $R^{6A}$ represents hydrogen, $R^{6B}$ represents hydrogen, $R^3$ represents a group of the formula

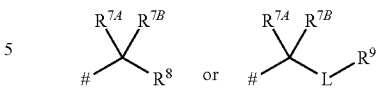

where

\# represents the point of attachment to the nitrogen atom,

L represents methylene, $R^{7A}$ represents hydrogen or methyl, $R^{7B}$ represents hydrogen or methyl, or $R^{7A}$ and $R^{7B}$ together with the carbon atom to which they are attached form a cyclopropyl ring, $R^8$ represents hydroxycarbonyl, methoxycarbonyl, ethoxycarbonyl or aminocarbonyl, $R^9$ represents hydroxy, methoxy, hydroxycarbonyl, methoxycarbonyl, ethoxycarbonyl or aminocarbonyl, and to their salts, solvates and solvates of the salts.

Preference in the context of the present invention is also given to compounds of the formula (I) in which $R^4$ represents a group of the formula

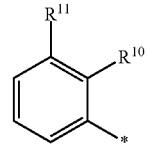

where

\* represents the point of attachment to the group —C($R^5$)(AC(=O)NH$R^3$)—, $R^{10}$ represents hydrogen, trifluoromethoxy, chlorine, trifluoromethyl and methoxy, $R^{11}$ represents hydrogen, trifluoromethoxy, fluorine, chlorine, trifluoromethyl and methoxy, where at least one of the radicals $R^{10}$ and $R^{11}$ is different from hydrogen, and to their salts, solvates and solvates of the salts.

Preference in the context of the present invention is also given to the following compounds of the formula (I):

ethyl 1-({[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylate (diastereomer mixture)

1-({[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylic acid (diastereomer mixture)

1-({[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylic acid (diastereomer 2)

methyl N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninate (diastereomer mixture)

N-{[({3-(4-chlorophenyl)-5-oxo-4-[(2S)-3,3,3-trifluoro-2-hydroxypropyl]-4,5-dihydro-1H-1,2,4-triazol-1- yl}acetyl)amino][3-(trifluoromethyl)phenyl]acetyl}-beta-alanine (diastereomer mixture)

$N^3$-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninamide (diastereomer 2)

$N^3$-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-beta-alaninamide methyl N-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalaninate N-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalanine $N^2$-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalaninamide methyl N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninate (diastereomer mixture)

N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer mixture)

N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer 2)

$N^2$-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer mixture)

$N^2$-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer 2)

methyl N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninate N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalanine $N^2$-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninamide 2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(1-hydroxy-2-methylpropan-2-yl)-2-[3-(trifluoromethyl)phenyl]acetamide (diastereomer 1)

2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[2-(trifluoromethyl)phenyl]acetamide (diastereomer mixture)

2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[2-(trifluoromethyl)phenyl]acetamide (diastereomer 2)

2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer mixture)

2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer 2)

2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethoxy)phenyl]acetamide (diastereomer mixture)

(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[2-(trifluoromethyl)phenyl]propanamide (3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[3-(trifluoromethyl)phenyl]propanamide (3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[3-(trifluoromethyl)phenyl]propanamide 2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-[2-(trifluoromethoxy)ethyl]-2-[3-(trifluoromethyl)phenyl]acetamide (diastereomer 2).

Particular preference in the context of the present invention is also given to the following compounds of the formula (I):

$N^3$-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninamide (diastereomer 2)

$N^3$-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-beta-alaninamide methyl-N-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalaninate N-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalanine $N^2$-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalaninamide N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer mixture)

N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer 2)

$N^2$-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer 2)

N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalanine 2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(1-hydroxy-2-methylpropan-2-yl)-2-[3-(trifluoromethyl)phenyl]-acetamide (diastereomer 1)
2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer mixture)
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[3-(trifluoromethyl)phenyl]propanamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[3-(trifluoromethyl)phenyl]propanamide.

Preference in the context of the present invention is also given to the following compounds of the formula (I):
methyl N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninate
N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalanine
$N^2$-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[2-(trifluoromethyl)phenyl]propanamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[3-(trifluoromethyl)phenyl]propanamide
(3S)-3-({[3-(4-chlorophenyl)-4-cyclopropyl-5-oxo-4,5-dihydro-1H-1,2,4-triazol-1-yl]acetyl]amino)-N-(2-hydroxyethyl)-3-[2-(trifluoromethyl)phenyl]propanamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[3-(trifluoromethyl)phenyl]propanamide.

Particular preference in the context of the present invention is also given to the following compounds of the formula (I):
N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalanine
$N^2$-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[2-(trifluoromethyl)phenyl]propanamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[3-(trifluoromethyl)phenyl]propanamide
(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[3-(trifluoromethyl)phenyl]propanamide.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention furthermore provides a process for preparing the compounds of the formula (I) according to the invention, characterized in that

[A] a compound of the formula (II)

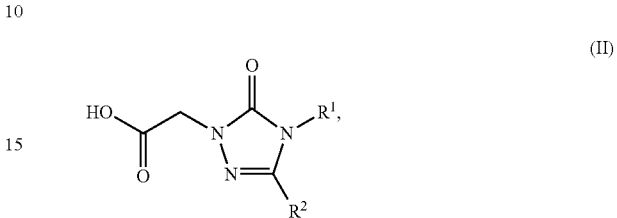

in which $R^1$ and $R^2$ each have the meanings given above,
is coupled in an inert solvent with activation of the carboxylic acid function with a compound of the formula (III)

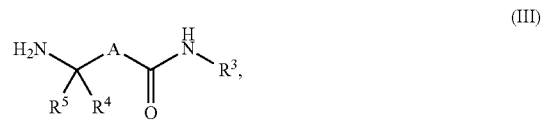

in which A, $R^3$, $R^4$ and $R^5$ each have the meanings given above, or

[B] a compound of the formula (IV)

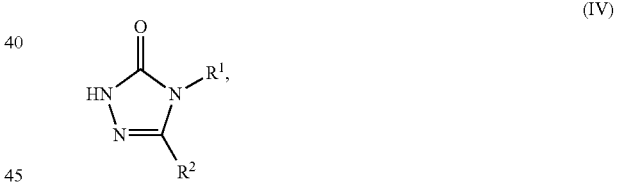

in which $R^1$ and $R^2$ each have the meanings given above,
is reacted in an inert solvent in the presence of a base with a compound of the formula (V)

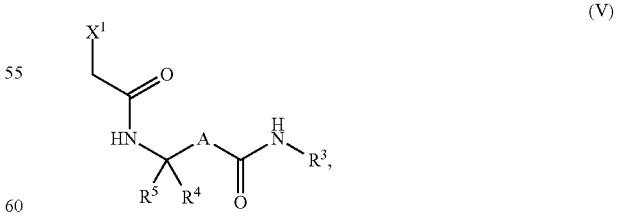

in which A, $R^3$, $R^4$ and $R^5$ each have the meanings given above,
and $X^1$ represents a leaving group, for example halogen, mesylate or tosylate, or

[C] a compound of the formula (VI)

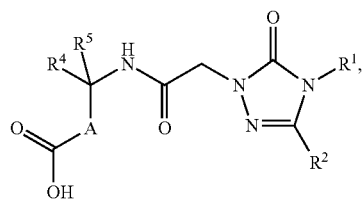

in which A, R$^1$, R$^2$, R$^4$ and R$^5$ each have the meanings given above, is coupled in an inert solvent with activation of the carboxylic acid function with a compound of the formula (VII)

H$_2$N—R$^3$   (VII), in which R$^3$ has the meaning given above,
and the resulting compounds of the formula (I) are optionally converted with the appropriate (i) solvents and/or (ii) acids or bases into their solvates, salts and/or solvates of the salts.

Inert solvents for the process steps (II)+(III)→(I) and (VI)+(VII)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N'-dimethylpropyleneurea (DMPU) or N-methylpyrrolidone (NMP). It is also possible to use mixtures of the solvents mentioned. Preference is given to acetonitrile, dichloromethane, tetrahydrofuran, dimethylformamide or mixtures of these solvents.

Suitable condensing agents for the amide formation in process steps (II)+(III)→(I) and (VI)+(VII)→(I) are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methyl-isoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with other additives such as 1-hydroxybenzotriazole (HOBt) or N-hydroxysuccinimide (HOSu), and, as bases, alkali metal carbonates, e.g. sodium or potassium carbonate or hydrogen carbonate, or organic bases such as trialkylamines, e.g. triethylamine, N-methylmorpholine, N-methylpiperidine or N,N-diisopropylethylamine. Preferably EDC in combination with HOBt or TBTU in the presence of N,N-diisopropylethylamine is used.

The condensations (II)+(III)→(I) and (VI)+(VII)→(I) are generally carried out in a temperature range of from −20° C. to +60° C., preferably at from 0° C. to +40° C. The reaction can be carried out at atmospheric, elevated or reduced pressure (for example from 0.5 to 5 bar). The reaction is generally carried out at atmospheric pressure.

Suitable inert solvents for the process step (IV)+(V)→(I) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, dimethyl sulphoxide, N,N'-dimethylpropyleneurea (DMPU), N-methylpyrrolidone (NMP) or pyridine. It is also possible to use mixture of the solvents mentioned. Preference is given to using acetonitrile, acetone or dimethylformamide.

Suitable bases for the process step (IV)+(V)→(I) are the customary inorganic or organic bases. These preferably include alkali metal hydroxides such as, for example, lithium hydroxide, sodium hydroxide or potassium hydroxide, alkali metal or alkaline earth metal carbonates such as lithium carbonate, sodium carbonate, potassium carbonate or caesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate or caesium carbonate.

Here, the base is employed in an amount of from 1 to 5 mol, preferably in an amount from 1 to 2.5 mol, per mole of the compound of the formula (IV). The reaction is generally carried out in a temperature range of from 0° C. to +100° C., preferably at from +20° C. to +80° C. The reaction can be carried out at atmospheric, elevated or reduced pressure (for example from 0.5 to 5 bar). The reaction is generally carried out at atmospheric pressure.

The preparation of the compounds according to the invention can be illustrated by the synthesis schemes below:

Scheme 1

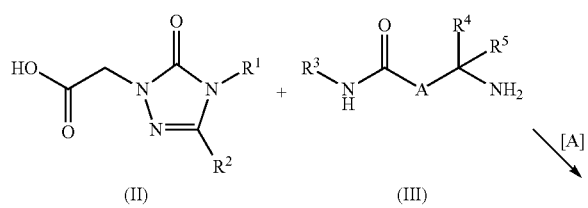

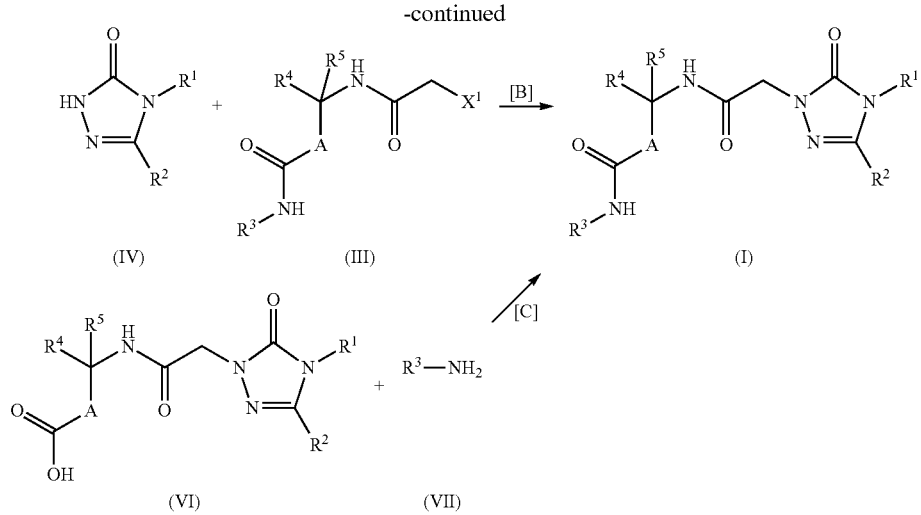

The compounds of the formulae (II), (IV) and (VI) are known from the literature (see, for example, WO 2007/134862), can be prepared analogously to processes known from the literature or as described in the present experimental part.

The compounds of the formulae (III), (V) and (VII) are commercially available, known from the literature or can be prepared analogously to processes known from the literature or as described in the present experimental part.

Further compounds according to the invention can also be prepared by converting functional groups of individual substituents, in particular those listed under $R^3$, starting with the compounds of the formula (I) obtained by the above processes. These conversions can be carried out by customary methods known to the person skilled in the art and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, formation of carboxamides, and also the introduction and removal of temporary protective groups.

The compounds according to the invention possess valuable pharmacological properties and can be used for the prevention and/or treatment of various diseases and disease-induced states in humans and animals.

The compounds according to the invention are potent, selective dual V1a/V2 receptor antagonists, which inhibit vasopressin activity in vitro and in vivo. Furthermore, the compounds according to the invention have increased solubility in aqueous media.

The compounds according to the invention are therefore particularly suitable for the prophylaxis and/or treatment of cardiovascular diseases. In this connection, the following may for example and preferably be mentioned as target indications: acute and chronic heart failure, arterial hypertension, coronary heart disease, stable and unstable angina pectoris, myocardial ischaemia, myocardial infarction, shock, arteriosclerosis, atrial and ventricular arrhythmias, transitory and ischaemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, oedema formation such as for example pulmonary oedema, cerebral oedema, renal oedema or heart failure-related oedema, and restenoses for example after thrombolysis treatments, percutaneous-transluminal angioplasties (PTA), transluminal coronary angioplasties (PTCA), heart transplants and bypass operations.

In the sense of the present invention, the term heart failure also includes more specific or related disease forms such as right heart failure, left heart failure, global insufficiency, ischaemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, diastolic heart failure and systolic heart failure.

Furthermore, the compounds according to the invention are suitable for use as a diuretic for the treatment of oedemas and in electrolyte disorders, in particular in hypervolaemic and euvolaemic hyponatraemia.

The compounds according to the invention are also suitable for the prophylaxis and/or treatment of polycystic kidney disease (PCKD) and the syndrome of inadequate ADH secretion (SIADH).

In addition, the compounds according to the invention can be used for the prophylaxis and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prophylaxis and/or treatment of central nervous disorders such as anxiety states and depression, of glaucoma and of cancer, in particular of pulmonary tumours.

Furthermore, the compounds according to the invention can be used for the prophylaxis and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example phaeochromocytoma and adrenal apoplexy, diseases of the intestine such as for example Crohn's disease and diarrhoea, or of menstrual disorders such as for example dysmenorrhoea or of endometriosis.

A further object of the present invention is the use of the compounds according to the invention for the treatment and/or prophylaxis of diseases, in particular of the diseases mentioned above.

A further object of the present invention is the compounds according to the invention for use in a method for the treatment and/or prophylaxis of acute and chronic heart failure, hypervolaemic and euvolaemic hyponatraemia, liver cirrhosis, ascites, oedemas, and the syndrome of inadequate ADH secretion (SIADH).

A further object of the present invention is the use of the compounds according to the invention for the production of a medicament for the treatment and/or prophylaxis of diseases, in particular of the diseases mentioned above.

A further object of the present invention is a method for the treatment and/or prophylaxis of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prophylaxis of the diseases mentioned above. As combination active substances suitable for this, the following may for example and preferably be mentioned:

organic nitrates and NO donors, such as for example sodium nitroprusside, nitroglycerine, isosorbide mononitrate, isosorbide dinitrate, molsidomine or SIN-1, and inhalational NO;

diuretics, in particular loop diuretics and thiazides and thiazide-like diuretics;

positive-inotropically active compounds, such as for example cardiac glycosides (digoxin), and beta-adrenergic and dopaminergic agonists such as isoproterenol, adrenalin, noradrenalin, dopamine and dobutamine;

compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as aminone and milrinone;

natriuretic peptides such as for example "atrial natriuretic peptide" (ANP, anaritide), "B-type natriuretic peptide" or "brain natriuretic peptide" (BNP, nesiritide), "C-type natriuretic peptide" (CNP) and urodilatin;

calcium sensitizers, such as for example and preferably levosimendan;

NO- and haem-independent activators of guanylate cyclase, such as in particular cinaciguat and also the compounds described in WO 01/19355, WO 01/19776, WO 01/19778, WO 01/19780, WO 02/070462 and WO 02/070510;

NO-independent, but haem-dependent stimulators of guanylate cyclase, such as in particular riociguat and also the compounds described in WO 00/06568, WO 00/06569, WO 02/42301 and WO 03/095451;

inhibitors of human neutrophil elastase (HNE), such as for example sivelestat or DX-890 (reltran);

compounds inhibiting the signal transduction cascade, such as for example tyrosine kinase inhibitors, in particular sorafenib, imatinib, gefitinib and erlotinib;

compounds influencing the energy metabolism of the heart, such as for example and preferably etomoxir, dichloroacetate, ranolazine or trimetazidine;

agents with antithrombotic action, for example and preferably from the group of the thrombocyte aggregation inhibitors, anticoagulants or profibrinolytic substances;

blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists and rho-kinase inhibitors; and/or active substances modifying the fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

In a preferred embodiment of the invention, the compounds according to the invention are administered in combination with a diuretic, such as for example and preferably furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerine, isosorbide, mannitol, amiloride or triamterene.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamole.

In a preferred embodiment of the invention, the compounds according to the invention are administered in combination with a thrombin inhibitor, such as for example and preferably ximela-gatran, melagatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably riva-roxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists, rho-kinase inhibitors and diuretics.

In a preferred embodiment of the invention, the compounds according to the invention are administered in combination with a calcium antagonist, such as for example and preferably nifedipine, amlodipine, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP).

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta-receptor blocker, such as for example and preferably propranolol, atenolol, timolol, pindolol, alprenolol, oxprenolol, penbutolol, bupranolol, meti-pranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenone, canrenone or potassium canrenoate.

In a preferred embodiment of the invention, the compounds according to the invention are administered in combination with a rho-kinase inhibitor, such as for example and preferably fasu-dil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, such as for example and preferably dalcetrapib, BAY 60-5521, anacetrapib or CETP-vaccine (CETi-1).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasi-mibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pio-glitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric bile acid adsorber, such as for example and preferably cholestyramine, colestipol, colesolvam, cholestagel or colestimide.

In a preferred embodiment of the invention, the compounds according to the invention are administered in combination with a bile acid reabsorption inhibitor, such as for example and preferably ASBT(=IBAT) inhibitors such as for example AZD-7806, S-8921, AK-105, BAR1-1741, SC-435 or SC-635.

In a preferred embodiment of the invention, the compounds according to the invention are administered in combination with a lipoprotein(a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable auxiliaries, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or otic routes or as an implant or stent.

For these administration routes, the compounds according to the invention can be administered in suitable administration forms.

For oral administration, administration forms which function according to the state of the art, releasing the compounds according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilisates, capsules (for example hard or soft gelatine capsules), sugar-coated tablets, granules, pellets, powders, emulsions, suspensions, aerosols or solutions are suitable.

Parenteral administration can be effected by omitting an absorption step (e.g. intravenous, intra-arterial, intracardial, intraspinal or intralumbar administration) or by involving absorption (e.g. intra-muscular, subcutaneous, intracutaneous, percutaneous or intraperitoneal administration). Suitable administration forms for parenteral administration include injection and infusion preparations in the form of solutions, suspensions, emulsions, lyophilisates or sterile powders.

For the other administration routes, for example inhalation formulations (including powder inhalers and nebulizers), nasal drops, solutions or sprays, tablets for lingual, sublingual or buccal administration, films/wafers or capsules, suppositories, aural or ophthalmic preparations, vaginal capsules, aqueous suspensions (lotions, shakable mixtures), lipophilic suspensions, ointments, creams, transdermal therapeutic systems (e.g. patches), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable auxiliaries. These auxiliaries include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as for example ascorbic acid), colorants (e.g. inorganic pigments such as for example iron oxides) and flavour and/or odour correctors.

In general, to achieve effective results in parenteral administration it has been found to be advantageous to administer quantities of about 0.01 to 1 mg/kg body weight. In oral administration, the dosage is about 0.01 to 100 mg/kg, preferably about 0.01 to 20 mg/kg and quite especially preferably 0.1 to 10 mg/kg body weight.

Nonetheless it can sometimes be necessary to deviate from said quantities, namely depending on body weight, administration route, individual response to the active substance, nature of the preparation and time or interval at which the administration takes place. Thus in some cases it can be sufficient to manage with less than the aforesaid minimum quantity, while in other cases the stated upper limit must be exceeded. In the event of administration of larger quantities, it may be advisable to divide these into several individual administrations throughout the day.

The following practical examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

A. EXAMPLES

Abbreviations

BOC tert-butoxycarbonyl
CI chemical ionization (in MS)
DCI direct chemical ionization (in MS)
DME 1,2-dimethoxyethane
DMF N,N'-dimethylformamide
DMSO dimethyl sulphoxide
EDC N'-(3-dimethylaminopropyl)-N-ethylcarbodiimide hydrochloride
eq. equivalent(s)
ESI electrospray ionization (in MS)
GC/MS gas chromatography-coupled mass spectrometry
sat. saturated
h hour(s)
HOBt 1-hydroxy-1H-benzotriazole hydrate
HPLC high pressure, high performance liquid chromatography
HV high vacuum
conc. concentrated
LC/MS liquid chromatography-coupled mass spectrometry
LDA lithium diisopropylamide
LiHMDS lithium hexamethyldisilazane
min minute(s)
MS mass spectrometry
MTBE methyl tert-butyl ether
NMR nuclear magnetic resonance spectrometry
rac racemic/racemate
$R_f$ retention factor (in thin-layer chromatography on silica gel)
RT room temperature
$R_t$ retention time (in HPLC)
THF Tetrahydrofuran
TMOF trimethyl orthoformate
UV ultraviolet spectrometry
v/v ratio by volume (of a solution)
LC/MS, HPLC and GC/MS Methods:

Method 1: MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 2: MS instrument type: Waters (Micromass) Quattro Micro; HPLC instrument type: Agilent 1100 Serie; column: Thermo Hypersil GOLD 3µ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml)→5.00 min 100% A; oven: 50° C.; flow rate: 2 ml/min; UV detection: 210 nm.

Method 3: Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.

Method 4: MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 5: Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 210-400 nm.

Method 6 (preparative HPLC): column: Grom-Sil 1200DS-4HE, 10 µm, SNr. 3331, 250 mm×30 mm mobile phase A: formic acid 0.1% in water, mobile phase B: acetonitrile; flow rate: 50 ml/min program: 0-6 min: 10% B; 6-27 min gradient to 95% B; 27-38 min: 95% B; 38-45 min: 10% B.

Method 7 (preparative HPLC): column: Reprosil C18, 10 µm, 250 mm×30 mm mobile phase A: formic acid 0.1% in water, mobile phase B: methanol; flow rate: 50 ml/min program: 0 to 4.25 min: 60% A/40% B; 4.25 to 4.50 min gradient to 60% B; 4.50 min to 17 min gradient to 100% B; 17 min to 19.50 min 100% B; 19.50 min to 19.75 min gradient to 40% B; 19.75 to 22 min (end): 60% A/40% B.

Method 8 (preparative HPLC): column: Reprosil C18, 10 µm, 250 mm×30 mm mobile phase A: formic acid 0.1% in water, mobile phase B: acetonitrile; flow rate: 50 ml/min program: 0 to 6 min: 90% A/10% B; 6 min to 27 min: gradient to 95% B; 27 min to 38 min 95% B; 38 min to 39 min gradient to 10% B; 39 min to 43 min (end): 60% A/40% B.

Method 9 (preparative HPLC): column: Grom-Sil 1200DS-4HE, 10 µm, SNo. 3331, 250 mm×30 mm mobile phase A: formic acid 0.1% in water, mobile phase B: acetonitrile; flow rate: 50 ml/min program: 0-6 min: 5% B; 6-34 min: gradient to 95% B; 34-38 min: 95% B; 38-45 min: 5% B.

Method 10 (chiral preparative HPLC): chiral stationary silica gel phase based on the selector poly-(N-methacryloyl-D-leucine-dicyclopropylmethylamide); column: 670 mm×40 mm; mobile phase: 100% ethyl acetate; flow rate: 80 ml/min, temperature: 24° C.; UV detector 260 nM.

Method 11 (chiral analytical HPLC): chiral stationary silica gel phase based on the selector poly-(N-methacryloyl-D-leucine-dicyclopropylmethylamide); column: 250 mm×4.6 mm, mobile phase ethyl acetate 100%, flow rate: 2 ml/min, temperature: 24° C.; UV detector 265 nM.

Method 12 (chiral preparative HPLC): chiral stationary vinyl silica gel phase based on the selector poly(N-methacryloyl-L-leucine-tert-butylamide); column: 670 mm×40 mm; mobile phase: isohexane/ethyl acetate 2:1; flow rate: 80 ml/min., temperature: 24° C.; UV detector 265 nM.

Method 13 (chiral analytical HPLC): chiral stationary vinyl silica gel phase based on the selector poly(N-methacryloyl-D-leucine-tert-butylamide); column: 250 mm×4.6 mm, mobile phase: isohexane/ethyl acetate 2:1; flow rate 1 ml/min, temperature 24° C.; UV-Detector 265 nM.

Method 14 (chiral preparative HPLC): stationary phase Daicel Chiralpak AD-H, 10 nm, column: 250 mm×20 mm; temperature: RT; UV detection: 230 nm; flow rate: 20 ml/min
   Method 14a: mobile phase: isohexane/isopropanol 70:30 (v/v).
   Method 14b: mobile phase: isohexane/isopropanol 50:50 (v/v).

Method 15 (chiral analytical HPLC): stationary phase Daicel Chiralpak AD-H, 5 nm, column: 250 mm×4.6 mm; temperature: 30° C.; UV detection: 230 nm; flow rate: 1.0 ml/min Various mobile phases:
   Method 15a: mobile phase: isohexane/isopropanol 70:30 (v/v).
   Method 15b: mobile phase: isohexane/isopropanol 50:50 (v/v).

Starting Materials and Intermediates

Example 1A

Ethyl N-({2-[(4-chlorophenyl)carbonyl]hydrazinyl}carbonyl)glycinate

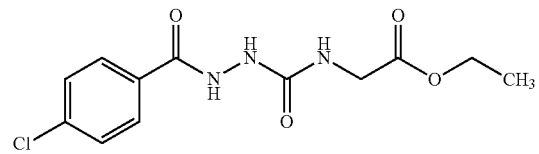 [SMILES: CCOC(=O)CNC(=O)NNC(=O)c1ccc(Cl)cc1]

A suspension of 12.95 g (75.9 mmol) of 4-chlorobenzhydrazide in 50 ml of dry THF was initially charged at 50° C., and a solution of 10.0 g (77.5 mmol) of ethyl 2-isocyanatoacetate in 100 ml of dry THF was added dropwise. Initially, a solution was formed, and then a precipitate. After the addition had ended, the mixture was stirred at 50° C. for a further 2 h and then allowed to stand overnight. The crystals were isolated by filtration, washed with a little diethyl ether and dried under HV. This gave 21.43 g (89% of theory) of the title compound.

LC/MS [Method 1]: $R_t$=1.13 min; m/z=300 (M+H)$^+$ $^1$H NMR (DMSO-d$_6$, 400 MHz): δ=10.29 (s, 1H), 8.21 (s, 1H), 7.91 (d, 2H), 7.57 (d, 2H), 6.88 (br.s, 1H), 4.09 (q, 2H), 3.77 (d, 2H), 1.19 (t, 3H)

Example 2A

[3-(4-Chlorophenyl)-5-oxo-1,5-dihydro-4H-1,2,4-triazol-4-yl]acetic acid

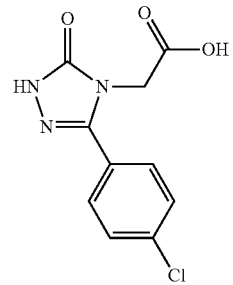 [SMILES: O=C(O)Cn1c(-c2ccc(Cl)cc2)n[nH]c1=O]

91 ml of a 3N aqueous sodium hydroxide solution were added to 21.43 g (67.93 mmol) of the compound of Example 1A, and the mixture was heated at reflux overnight. After cooling to RT, the mixture was adjusted to pH 1 by slow addition of about 20% strength hydrochloric acid. The precipitated solid was isolated by filtration, washed with water and dried under reduced pressure at 60° C. Yield: 17.55 g (90% of theory, about 88% pure).

LC/MS [Method 1]: $R_t$=0.94 min; m/z=254 (M+H)$^+$ $^1$H NMR (DMSO-d$_6$, 400 MHz): δ=13.25 (br.s, 1H), 12.09 (s, 1H), 7.65-7.56 (m, 4H), 4.45 (s, 2H).

Example 3A 5-(4-Chlorophenyl)-4-(3,3,3-trifluoro-2-oxopropyl)-
2,4-dihydro-3H-1,2,4-triazol-3-one (or as hydrate:
5-(4-chlorophenyl)-4-(3,3,3-trifluoro-2,2-dihydroxypropyl)-2,4-dihydro-3H-1,2,4-triazol-3-one)

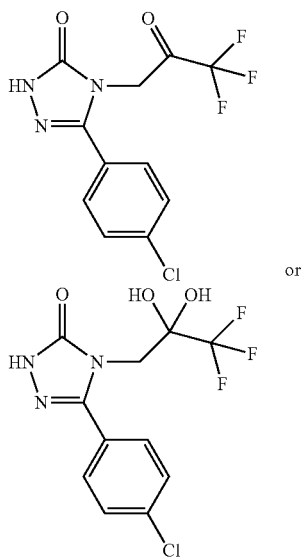

Under argon, 5 g (16.36 mmol) of the compound of Example 2A were dissolved in 200 ml of pyridine, and 17.18 g (81.8 mmol) of trifluoroacetic anhydride were then added. During the addition, the temperature increased to about 35° C. After 30 min, the pyridine was removed on a rotary evaporator and the residue was diluted with 1.5 l of 0.5N hydrochloric acid. This mixture was heated to 70° C. and then filtered whilst still hot. The solid was washed with a little water. The entire filtrate was extracted three times with ethyl acetate. The combined organic phases were washed with water, then with a saturated aqueous sodium bicarbonate solution, then with a saturated aqueous sodium chloride solution, dried over sodium sulphate and freed from the solvent on a rotary evaporator. The residue was dried under HV. Yield: 3.56 g (68% of theory) of the title compound as a hydrate.

LC/MS [Method 1]: $R_t$=1.51 min; m/z=306 (M+H)$^+$ and 324 (M+H)$^+$ (ketone or hydrate)

$^1$H NMR (DMSO-d$_6$, 400 MHz): δ=12.44 (s, 1H), 7.72 (d, 2H), 7.68 (br.s, 2H), 7.61 (d, 2H), 3.98 (s, 2H).

Example 4A 5-(4-Chlorophenyl)-4-(3,3,3-trifluoro-2-hydroxypropyl)-2,4-dihydro-3H-1,2,4-triazol-3-one

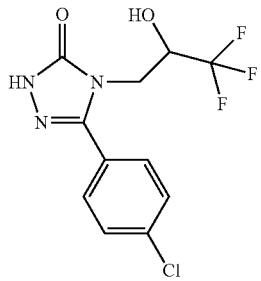 [SMILES: O=c1[nH]nc(-c2ccc(Cl)cc2)n1CC(O)C(F)(F)F]

3.56 g (11 mmol) of the compound of Example 3A were dissolved in 100 ml of methanol, and 3.75 g (99 mmol) of sodium borohydride were added with ice cooling (evolution of gas). After 1.5 h, 200 ml of 1M hydrochloric acid were added slowly. The methanol was removed on a rotary evaporator, and the residue was diluted with 500 ml of water and extracted three times with ethyl acetate. The combined organic phases were washed with a saturated aqueous sodium bicarbonate solution and then with a saturated aqueous sodium chloride solution, dried over sodium sulphate and freed from the solvent on a rotary evaporator. The residue was dried under HV. This gave 3.04 g (90% of theory) of the title compound.

LC/MS [Method 2]: $R_t$=1.80 min; m/z=308 (M+H)$^+$.

$^1$H NMR (DMSO-d$_6$, 400 MHz): δ=12.11 (s, 1H), 7.75 (d, 2H), 7.62 (d, 2H), 6.85 (d, 1H), 4.34-4.23 (m, 1H), 3.92 (dd, 1H), 3.77 (dd, 1H).

Example 5A

Methyl[3-(4-chlorophenyl)-5-oxo-4-(3,3,3-trifluoro-
2-hydroxypropyl)-4,5-dihydro-1H-1,2,4-triazol-1-yl]
acetate

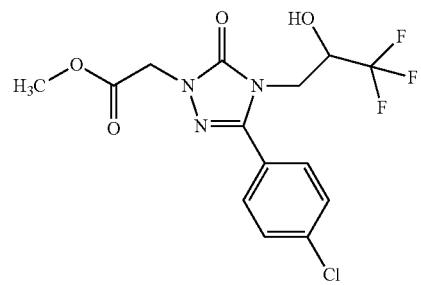 [SMILES: COC(=O)Cn1nc(-c2ccc(Cl)cc2)n(CC(O)C(F)(F)F)c1=O]

3.04 g (9.9 mmol) of the compound of Example 4A were dissolved in 100 ml of acetonitrile, and 1.07 g (9.9 mmol) of methyl chloroacetate, 2.73 g (19.8 mmol) of potassium carbonate and a small spatula tip of potassium iodide were added. The reaction mixture was heated at reflux for 1 h, allowed to cool to RT and filtered. The filtrate was freed from the volatile components on a rotary evaporator and the residue was dried under HV. Yield: 3.70 g (89% of theory) of the title compound in a purity of about 90%.

LC/MS [Method 3]: $R_t$=1.10 min; m/z=380 (M+H)$^+$.

$^1$H NMR (DMSO-d$_6$, 400 MHz): δ=7.78 (d, 2H), 7.64 (d, 2H), 6.91 (d, 1H), 4.72 (s, 2H), 4.16-4.35 (m, 1H), 3.99 (dd, 1H), 3.84 (dd, 1H), 3.70 (s, 3H).

The racemic compound of Example 5A was, as described in WO 2007/134862, separated by preparative HPLC on a chiral phase into the enantiomers Example 6A and Example 7A.

Column: chiral silica gel phase based on the selector poly (N-methacryloyl-L-isoleucine-3-pentylamide, 430 mm×40 mm; mobile phase: stepped gradient isohexane/ethyl acetate 1:1 (v/v)→ethyl acetate→isohexane/ethyl acetate 1:1 (v/v); flow rate: 50 ml/min; temperature: 24° C.; UV detection: 260 nm.

In this manner, 3.6 g of the racemic compound of Example 5A (dissolved in 27 ml of ethyl acetate and 27 ml of isohexane and separated in three portions on the column) gave 1.6 g of enantiomer 1 (Example 6A), which eluted first, and 1.6 g of enantiomer 2 (Example 7A), which eluted later.

Example 6A

Methyl{3-(4-chlorophenyl)-5-oxo-4-[(2S)-3,3,3-trifluoro-2-hydroxypropyl]-4,5-dihydro-1H-1,2,4-triazol-1-yl}acetate (enantiomer 1)

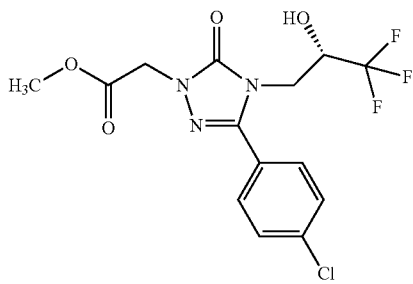 [SMILES: COC(=O)Cn1nc(-c2ccc(Cl)cc2)n(C[C@H](O)C(F)(F)F)c1=O]

First-eluting enantiomer from the racemate separation of Example 5A.

$R_t$=3.21 min [column: chiral silica gel phase based on the selector poly(N-methacryloyl-L-isoleucine-3-pentylamide, 250 mm×4.6 mm; mobile phase: isohexane/ethyl acetate 1:1; flow rate: 1 ml/min; UV detection: 260 nm].

Example 7A

Methyl{3-(4-chlorophenyl)-5-oxo-4-[(2R)-3,3,3-trifluoro-2-hydroxypropyl]-4,5-dihydro-1H-1,2,4-triazol-1-yl}acetate (enantiomer 2)

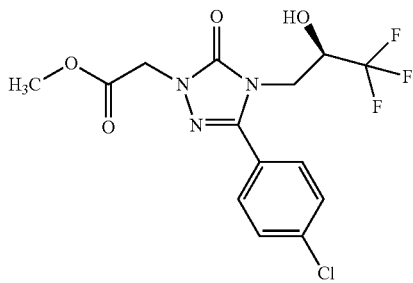 [SMILES: COC(=O)Cn1nc(-c2ccc(Cl)cc2)n(C[C@@H](O)C(F)(F)F)c1=O]

Last-eluting enantiomer from the racemate separation of Example 5A.

$R_t$=4.48 min [column: chiral silica gel phase based on the selector poly(N-methacryloyl-L-isoleucine-3-pentylamide, 250 mm×4.6 mm; mobile phase: isohexane/ethyl acetate 1:1; flow rate: 1 ml/min; UV detection: 260 nm].

Example 8A

{3-(4-Chlorophenyl)-5-oxo-4-[(2S)-3,3,3-trifluoro-2-hydroxypropyl]-4,5-dihydro-1H-1,2,4-triazol-1-yl}acetic acid

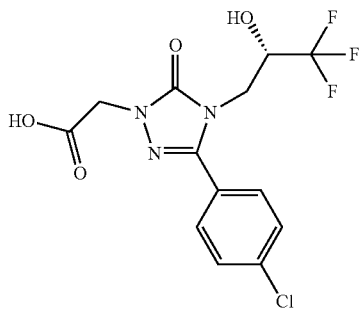 [SMILES: O=C(O)Cn1nc(-c2ccc(Cl)cc2)n(C[C@H](O)C(F)(F)F)c1=O]

The enantiomerically pure ester of Example 6A (1.6 g, 4.21 mmol) was dissolved in 77 ml of methanol, and 17 ml of a 1M solution of lithium hydroxide in water were added. The mixture was stirred at RT for 1 h and then concentrated on a rotary evaporator. The residue was diluted with 100 ml of water and acidified to pH 1-2 with 1N of hydrochloric acid. The precipitated product was filtered off, washed successively with water and cyclohexane and sucked dry. Further drying under HV gave the title compound (1.1 g, 71% of theory).

[α]$_D$'=+3.4° (methanol, c=0.37 g/100 ml)

LC/MS [Method 1]: $R_t$=1.51 min; m/z=366 (M+H)$^+$ $^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 9A

{3-(4-Chlorophenyl)-5-oxo-4-[(2R)-3,3,3-trifluoro-2-hydroxypropyl]-4,5-dihydro-1H-1,2,4-triazol-1-yl}acetic acid

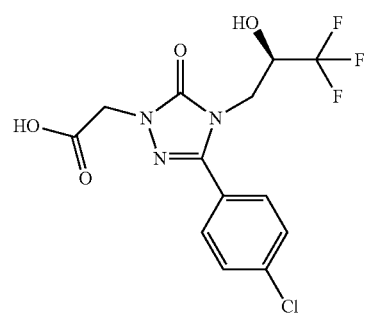 [SMILES: O=C(O)Cn1nc(-c2ccc(Cl)cc2)n(C[C@@H](O)C(F)(F)F)c1=O]

Analogously to Example 8A, Example 7A gave the title compound.

[α]$_D$'=-4.6° (methanol, c=0.44 g/100 ml)

LC/MS [Method 1]: $R_t$=1.53 min; m/z=366 (M+H)$^+$ $^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 10A

Methyl{3-(4-chlorophenyl)-5-oxo-4-[(1E)-3,3,3-trifluoroprop-1-en-1-yl]-4,5-dihydro-1H-1,2,4-triazol-1-yl}acetate

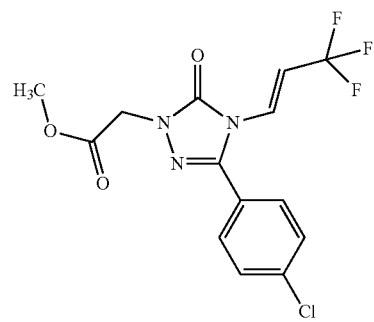 [SMILES: COC(=O)Cn1nc(-c2ccc(Cl)cc2)n(/C=C/C(F)(F)F)c1=O]

At RT, 280 mg (0.74 mmol) of the compound of Example 7A were initially charged together with 108 mg (0.89 mmol) of 4-dimethylaminopyridine in 5.3 ml of pyridine, 0.31 ml of trifluoromethanesulphonic anhydride (1.84 mmol) was added in portions and the mixture was stirred for 12 h. The pyridine was removed on a rotary evaporator. The residue was taken up in acetonitrile and 1N hydrochloric acid and purified by preparative HLPC [Method 9]. This gave 230 mg (86% of theory) of the title compound.

LC/MS [Method 4]: $R_t$=1.14 min; m/z=362 (M+H)$^+$ $^1$H-NMR (400 MHz, DMSO-d$_6$): δ [ppm]=3.72 (s, 3H), 4.78 (s, 2H), 6.85 (dd, 1H), 7.18 (d, 1H), 7.68 (s, 4H).

Example 11A

{3-(4-Chlorophenyl)-5-oxo-4-[(1E)-3,3,3-trifluoroprop-1-en-1-yl]-4,5-dihydro-1H-1,2,4-triazol-1-yl}acetic acid

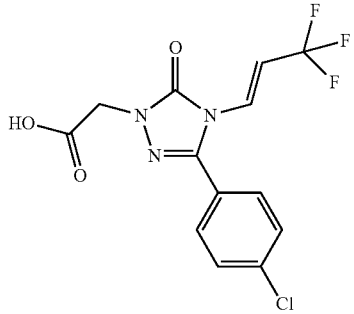 [SMILES: O=C(O)Cn1nc(-c2ccc(Cl)cc2)n(/C=C/C(F)(F)F)c1=O]

260 mg (0.72 mmol) of the compound of Example 10A were dissolved in 5 ml of methanol, and 2.87 ml (2.87 mmol) of a 1M aqueous lithium hydroxide solution were added. The mixture was stirred at RT for 1 h and then acidified with 1N hydrochloric acid and diluted with DMSO. The entire solution was purified by preparative HLPC [Method 9]. This gave 215 mg (86% of theory) of the title compound.

LC/MS [Method 4]: $R_t$=1.03 min; m/z=348 (M+H)$^+$ $^1$H-NMR (400 MHz, DMSO-d$_6$): δ [ppm]=4.64 (s, 2H), 6.79-6.92 (m, 1H), 7.19 (dd, 1H), 7.68 (s, 4H), 13.31 (br. s, 1H).

Example 12A

2-[(5-Chloro-2-thienyl)carbonyl]-N-(2-methoxyethyl)hydrazinecarboxamide

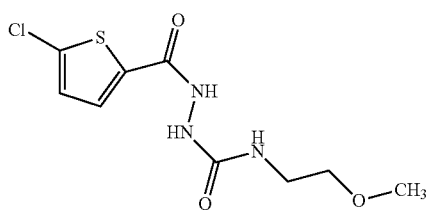 [SMILES: COCCNC(=O)NNC(=O)c1ccc(Cl)s1]

At 50° C., 3.1 g (17.55 mmol) of 5-chlorothiophene-2-carbohydrazide were finely suspended in 30 ml of dry THF. 1.81 g (17.90 mmol) of 1-isocyanato-2-methoxyethane dissolved in 30 ml of THF were then added dropwise. The mixture was stirred at 50° C. for 2.5 h. After cooling to RT, the solvent was removed on a rotary evaporator, and diethyl ether was added to the residue. The crystals were filtered off with suction, washed with diethyl ether and dried under high vacuum. This gave 4.87 g (100% of theory) of the title compound.

$^1$H-NMR (400 MHz, DMSO-d$_6$): δ=3.14-3.21 (m, 2H), 3.28-3.36 (m, 5H), 6.52 (br. s, 1H), 7.22 (d, 1H), 7.70 (d, 1H), 7.97 (s, 1H), 10.24 (s, 1H).

Example 13A 5-(5-Chloro-2-thienyl)-4-(2-methoxyethyl)-2,4-dihydro-3H-1,2,4-triazol-3-one

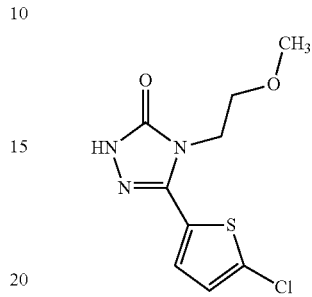

4.85 g (17.46) mmol of the compound of Example 12A were dissolved in 17 ml (52.39 mmol) of 3M aqueous sodium hydroxide solution and heated under reflux for 168 h. After 16, 40, 64 and 88 h, in each case 1.05 g (26.19 mmol, 104.76 mmol in total) of solid sodium hydroxide were added. Using 1M hydrochloric acid, the mixture was adjusted to pH 10, and the mixture was extracted twice with in each case 30 ml of ethyl acetate. The combined organic phases were dried over sodium sulphate, filtered, freed from the solvent on a rotary evaporator and dried under high vacuum. This gave 2.44 g (54% of theory) of the title compound.

$^1$H-NMR (400 MHz, DMSO-d$_6$): δ=3.20 (s, 3H), 3.53 (t, 2H), 3.92 (t, 2H), 7.24 (d, 1H), 7.51 (d, 1H), 12.04 (s, 1H).

Example 14A

Ethyl[3-(5-chloro-2-thienyl)-4-(2-methoxyethyl)-5-oxo-4,5-dihydro-1H-1,2,4-triazol-1-yl]acetate

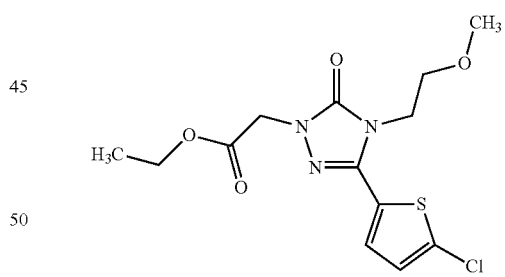

2.4 g (9.24 mmol) of the compound of Example 13A and 2.55 g (18.48 mmol) of potassium carbonate were suspended in 48 ml of acetonitrile. 1.08 ml (10.17 mmol) of ethyl chloroacetate were then added, and the mixture was heated under reflux at 80° C. for 4.5 h. Another 113 mg (0.92 mmol) of ethyl chloroacetate were added, and the mixture was stirred at 80° C. for 2 h. The suspension was filtered through a layer of silica gel, the silica gel was washed with ethyl acetate and the filtrate was evaporated on a rotary evaporator and dried under HV. This gave 3.24 g (100% of theory) of the title compound.

LC/MS [Method 22]: $R_t$=2.42 min; m/z=346 (M+H)$^+$.

$^1$H-NMR (400 MHz, DMSO-d$_6$): δ=1.21 (t, 3H), 3.30 (s, 3H), 3.55 (t, 2H), 3.99 (t, 2H), 4.15 (q, 2H), 4.65 (s, 2H), 7.27 (d, 1H), 7.58 (d, 1H).

Example 15A

[3-(5-Chloro-2-thienyl)-4-(2-methoxyethyl)-5-oxo-4,5-dihydro-1H-1,2,4-triazol-1-yl]acetic acid

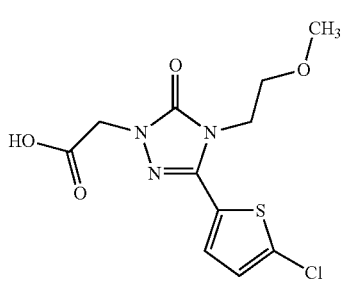 [SMILES: COCCn1c(-c2ccc(Cl)s2)nn(CC(=O)O)c1=O]

3.2 g (9.25 mmol) of the compound of Example 14A were dissolved in 28 ml of methanol. 2.82 ml of 20% strength aqueous potassium hydroxide solution were then added. The mixture was stirred at RT for 2 h. On a rotary evaporator, the proportion of methanol was reduced by half. The mixture was then diluted with water and extracted once with 15 ml of ethyl acetate. The aqueous phase was acidified with 920 µl of concentrated hydrochloric acid and extracted twice with in each case 15 ml of ethyl acetate. The combined organic phases were dried over sodium sulphate, filtered and concentrated on a rotary evaporator. Drying under high vacuum gave 2.34 g (80% of theory) of the title compound.

LC/MS [Method 22]: $R_t$=2.05 min; m/z=318 (M+H)$^+$.
$^1$H-NMR (400 MHz, DMSO-d$_6$): δ=3.20 (s, 3H), 3.55 (t, 2H), 3.99 (t, 2H), 4.53 (s, 2H), 7.27 (d, 1H), 7.58 (d, 1H), 13.14 (br. s, 1H).

Example 16A (2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoic acid

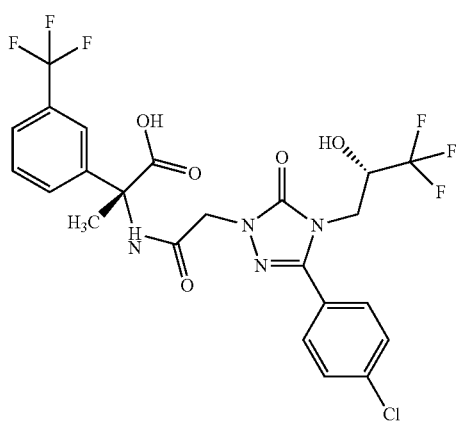 [SMILES: C[C@](NC(=O)Cn1nc(-c2ccc(Cl)cc2)n(C[C@H](O)C(F)(F)F)c1=O)(C(=O)O)c1cccc(C(F)(F)F)c1]

250 mg of the compound of Example 8A (0.68 mmol) of and 92 mg (0.68 mmol) of HOBt were initially charged in 5 ml of DMF, and 131 mg (0.68 mmol) of EDC were added. The mixture was stirred at RT for 20 min and then added dropwise to a solution of 221 mg (0.82 mmol) of (2R)-2-amino-2-[3-(trifluoromethyl)phenyl]propionic acid hydrochloride and 119 µl (0.68 mmol) of N,N-diisopropylethylamine in 2 ml of DMF. The reaction mixture was stirred at RT for 20 min, 1 ml of 1N hydrochloric acid was then added and the product was purified by preparative HPLC (Method 10). The appropriate fraction was concentrated on a rotary evaporator and the residue was dried under HV. This gave 260 mg (65% of theory) of the title compound.

LC-MS [Method 3]: $R_t$=1.23 min; MS [ESIpos]: m/z=581 (M+H)$^+$
$^1$H-NMR (400 MHz, DMSO-d$_6$): δ [ppm]=1.85 (s, 3H), 3.76-3.88 (m, 1H), 3.90-4.01 (m, 1H), 4.26 (br. s., 1H), 4.51-4.67 (m, 2H), 6.92 (d, 1H), 7.55-7.71 (m, 4H), 7.71-7.83 (m, 4H), 8.80 (s, 1H), 13.10 (s, 1H).

Example 17A

Ethyl 1-({[[(tert-butoxycarbonyl)amino][3-(trifluoromethyl)phenyl]acetyl}amino)cyclopropanecarboxylate

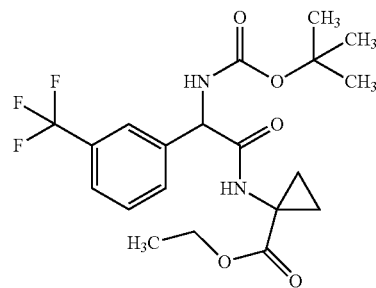 [SMILES: CCOC(=O)C1(NC(=O)C(NC(=O)OC(C)(C)C)c2cccc(C(F)(F)F)c2)CC1]

A mixture of 500 mg (1.57 mmol) of [(tert-butoxycarbonyl)amino][3-(trifluoromethyl)-phenyl]acetic acid, 243 mg (1.88 mmol) of ethyl 1-aminocyclopropanecarboxylate, 450 mg (2.35 mmol) of EDC and 317 mg (2.35 mmol) of HOBt in 10 ml of DMF was stirred at RT overnight. The reaction mixture was diluted with ethyl acetate and washed twice with 1N hydrochloric acid and once with a saturated aqueous sodium bicarbonate solution. The organic phase was dried over sodium sulphate and then freed from the solvent on a rotary evaporator. The residue was dried under high vacuum. This gave 650 mg (96% of theory) of the title compound.

LC-MS [Method 1]: $R_t$=2.11 min; MS [ESIpos]: m/z=431 (M+H)$^+$
$^1$H-NMR (400 MHz, DMSO-d$_6$): δ [ppm]=0.92 (t, 3H), 0.95-1.04 (m, 2H), 1.24-1.33 (m, 2H), 1.37 (s, 9H), 3.89 (q, 2H), 5.23 (d, 1H), 7.50 (br. d, 1H), 7.59 (t, 1H), 7.66 (d, 1H), 7.73 (d, 1H), 7.80 (s, 1H), 8.91 (s, 1H).

Example 18A

Methyl N-{[(tert-butoxycarbonyl)amino][3-(trifluoromethyl)phenyl]acetyl}-2-methylalaninate

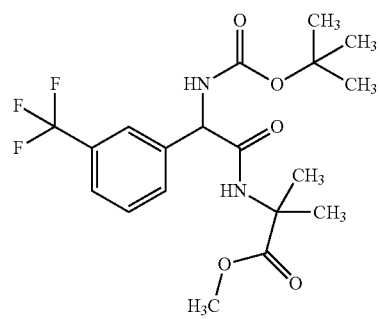 [SMILES: COC(=O)C(C)(C)NC(=O)C(NC(=O)OC(C)(C)C)c1cccc(C(F)(F)F)c1]

450 mg (2.35 mmol) of EDC were added to a mixture of 500 mg (1.57 mmol) of [(tert-butoxycarbonyl)amino][3-(trifluoromethyl)phenyl]acetic acid and 317 mg (2.35 mmol) of HOBt in 10 ml of DMF, and the mixture was stirred at RT for 20 min. 313 mg (2.04 mmol) of methyl 2-methylalaninate hydrochloride and 382 μl (2.19 mmol) of N,N'-diisopropylethylamine were added and the mixture was stirred overnight. For purification, the entire reaction mixture was separated by preparative HPLC [Method 6]. The appropriate fraction was concentrated on a rotary evaporator and the residue was dried under high vacuum. This gave 502 mg (77% of theory) of the title compound.

LC-MS [Method 3]: $R_t$=1.28 min; MS [ESIpos]: m/z=319 (M+H−BOC)$^+$; [ESIneg]: m/z=417 (M−H)$^−$.

$^1$H-NMR (400 MHz, DMSO-d$_6$): δ [ppm]=1.26 (s, 3H), 1.38 (d, 12H), 3.44 (s, 3H), 5.31 (d, 1H), 7.45 (br. d, 1H), 7.56-7.62 (m, 1H), 7.63-7.71 (m, 2H), 7.75 (br. s, 1H), 8.61-8.69 (m, 1H).

Example 19A

Methyl N-{[(tert-butoxycarbonyl)amino][3-(trifluoromethyl)phenyl]acetyl}-beta-alaninate

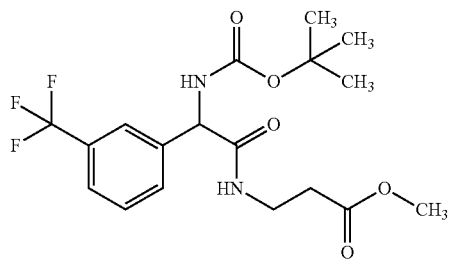 [SMILES: COC(=O)CCNC(=O)C(NC(=O)OC(C)(C)C)c1cccc(C(F)(F)F)c1]

Analogously to Example 18A, 250 mg (0.78 mmol) of [(tert-butoxycarbonyl)amino][3-(trifluoromethyl)phenyl] acetic acid and 142 mg (1.02 mmol) of methyl beta-alaninate hydrochloride gave 256 mg (81% of theory) of the title compound.

LC-MS [Method 1]: $R_t$=1.90 min; MS [ESIpos]: m/z=405 (M+H)$^+$.

$^1$H-NMR (400 MHz, DMSO-d$_6$): δ [ppm]=1.37 (s, 9H), 2.42 (t, 2H), 3.20-3.33 (m, 2H), 3.51 (s, 3H), 5.23 (d, 1H), 7.51 (br. d, 1H), 7.54-7.60 (m, 1H), 7.61-7.71 (m, 2H), 7.76 (br. s, 1H), 8.36 (t, 1H).

Example 20A tert-Butyl{2-[(3-amino-3-oxopropyl)amino]-2-oxo-1-[3-(trifluoromethyl)phenyl]ethyl}carbamate (racemate)

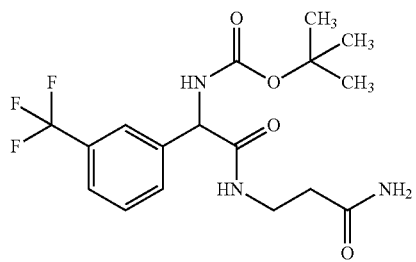 [SMILES: CC(C)(C)OC(=O)NC(C(=O)NCCC(N)=O)c1cccc(C(F)(F)F)c1]

360 mg (1.88 mmol) of EDC were added to a mixture of 400 mg (1.25 mmol) of [(tert-butoxycarbonyl)amino][3-(trifluoromethyl)phenyl]acetic acid and 254 mg (1.88 mmol) of HOBt in 12 ml of DMF, and the mixture was stirred at RT for 30 min 234 mg (1.88 mmol) of beta-alaninamide hydrochloride and 436 μl (2.50 mmol) of N,N'-diisopropylethylamine were added, and the mixture was stirred for another 1 h. The mixture was diluted with ethyl acetate and washed four times with water. The organic phase was dried over sodium sulphate and freed from the solvent on a rotary evaporator. The residue was dried under high vacuum. This gave 446 mg (91% of theory) of the title compound.

LC-MS [Method 1]: $R_t$=1.56 min; MS [ESIpos]: m/z=390 (M+H)$^+$.

$^1$H-NMR (400 MHz, DMSO-d$_6$): δ [ppm]=1.37 (s, 9H), 2.11-2.26 (m, 2H), 3.15-3.28 (m, 2H), 5.25 (d, 1H), 6.81 (br. s., 1H), 7.29 (br. s., 1H), 7.50 (d, 1H), 7.53-7.60 (m, 1H), 7.64 (d, 1H), 7.69 (d, 1H), 7.77 (s, 1H), 8.30 (t, 1H).

By chromatography on a chiral phase [Method 14a], the title compound was separated into its enantiomers: see Examples 21A and 22A.

Example 21A tert-Butyl{2-[(3-amino-3-oxopropyl)amino]-2-oxo-1-[3-(trifluoromethyl)phenyl]ethyl}carbamate (enantiomer 1)

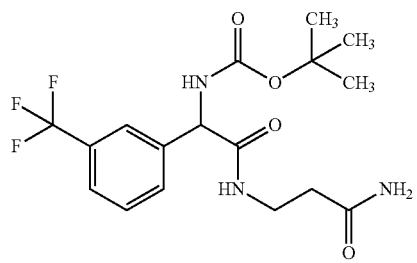 [SMILES: CC(C)(C)OC(=O)NC(C(=O)NCCC(N)=O)c1cccc(C(F)(F)F)c1]

First-eluting enantiomer (205 mg) from the chromatographic enantiomer separation of the compound of Example 20A according to Method 14a.

Chiral analytical HPLC [Method 15b]: $R_t$=3.29 min

Example 22A tert-Butyl{2-[(3-amino-3-oxopropyl)amino]-2-oxo-1-[3-(trifluoromethyl)phenyl]ethyl}carbamate (enantiomer 2)

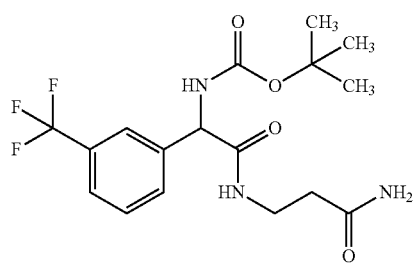 [SMILES: CC(C)(C)OC(=O)NC(C(=O)NCCC(N)=O)c1cccc(C(F)(F)F)c1]

Last-eluting enantiomer (208 mg) from the chromatographic enantiomer separation of the compound of Example 20A according to Method 14a.

Chiral analytical HPLC [Method 15b]: $R_t$=4.15 min

Example 23A tert-Butyl{2-[(1-amino-2-methyl-1-oxopropan-2-yl)amino]-2-oxo-1-[3-(trifluoromethyl)phenyl]ethyl}carbamate

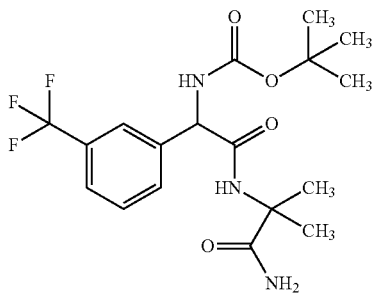 [SMILES: CC(C)(C)OC(=O)NC(C(=O)NC(C)(C)C(N)=O)c1cccc(C(F)(F)F)c1]

Analogously to Example 18A, 222 mg (0.69 mmol) of [(tert-butoxycarbonyl)amino][3-(trifluoromethyl)phenyl]acetic acid and 115 mg (0.77 mmol) of 2-methylalaninamide hydrochloride gave 237 mg (85% of theory) of the title compound.

LC-MS [Method 4]: $R_t$=2.04 min; MS [ESIpos]: m/z=404 (M+H)$^+$.

$^1$H-NMR (400 MHz, DMSO-d$_6$): δ [ppm]=1.30 (s, 3H), 1.33 (s, 3H), 1.38 (s, 9H), 5.23 (d, 1H), 6.96 (br. s, 1H), 6.99 (br. s, 1H), 7.50-7.61 (m, 2H), 7.64 (d, 1H), 7.69 (d, 1H), 7.77 (s, 1H), 8.28 (br. s., 1H).

Example 24A tert-Butyl{2-[(1-amino-2-methyl-1-oxopropan-2-yl)amino]-2-oxo-1-[2-(trifluoromethyl)phenyl]ethyl}carbamate

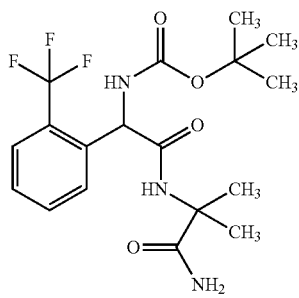 [SMILES: CC(C)(C)OC(=O)NC(C(=O)NC(C)(C)C(N)=O)c1ccccc1C(F)(F)F]

Analogously to Example 18A, 250 mg (0.78 mmol) of [(tert-butoxycarbonyl)amino][2-(trifluoromethyl)phenyl]acetic acid and 119 mg (0.86 mmol) of 2-methylalaninamide hydrochloride gave 220 mg (70% of theory) of the title compound.

LC-MS [Method 3]: $R_t$=1.07 min; MS [ESIpos]: m/z=404 (M+H)$^+$.

$^1$H-NMR (400 MHz, DMSO-d$_6$): δ [ppm]=1.38 (br. s., 9H), 1.39 (br. s., 3H), 1.41 (s, 3H), 5.36 (d, 1H), 7.12 (s, 1H), 7.22 (br. s., 1H), 7.50 (t, 1H), 7.57 (d, 1H), 7.63-7.73 (m, 2H), 7.90 (d, 1H), 8.04 (s, 1H).

Example 25A tert-Butyl{2-[(1-amino-2-methyl-1-oxopropan-2-yl)amino]-1-(2-chlorophenyl)-2-oxoethyl}carbamate

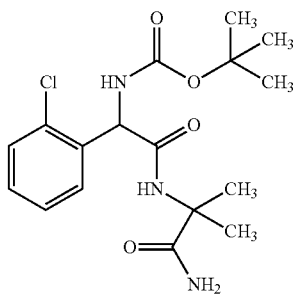 [SMILES: CC(C)(C)OC(=O)NC(C(=O)NC(C)(C)C(N)=O)c1ccccc1Cl]

Analogously to Example 18A, 250 mg (0.88 mmol) of [(tert-butoxycarbonyl)amino](2-chlorophenyl)acetic acid and 133 mg (0.96 mmol) of 2-methylalaninamide hydrochloride gave 263 mg (81% of theory) of the title compound.

LC-MS [Method 5]: $R_t$=0.81 min; MS [ESIpos]: m/z=370 (M+H)$^+$.

$^1$H-NMR (400 MHz, DMSO-d$_6$): δ [ppm]=1.38 (br. s., 3H), 1.39 (br. s., 9H), 1.41 (s, 3H), 5.40 (d, 1H), 7.08 (br. s., 1H), 7.11 (br. s., 1H), 7.29-7.35 (m, 2H), 7.37-7.48 (m, 2H), 7.69 (d, 1H), 8.06 (s, 1H).

Example 26A

[(tert-Butoxycarbonyl)amino](2,3-dichlorophenyl)acetic acid

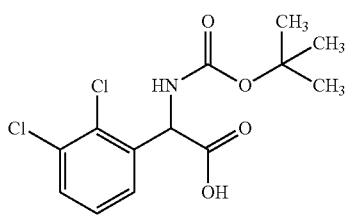 [SMILES: CC(C)(C)OC(=O)NC(C(=O)O)c1cccc(Cl)c1Cl]

A solution of 500 mg (2.27 mmol) of amino(2,3-dichlorophenyl)acetic acid in 25 ml of 5% strength aqueous sodium bicarbonate solution was diluted with 25 ml of dioxane, and 532 ml (2.32 mmol) of di-tert-butyl dicarbonate were added. The reaction mixture was stirred at RT overnight. For work-up, 150 ml of 1N hydrochloric acid were added, and the product was extracted three times with ethyl acetate. The combined organic phases were dried over sodium sulphate and freed from the solvent on a rotary evaporator. The residue was dried under high vacuum. This gave 750 mg (quant. yield) of the title compound.

LC-MS [Method 5]: $R_t$=1.00 min; MS [ESIpos]: m/z=320 (M+H)$^+$.

$^1$H-NMR (400 MHz, DMSO-d$_6$): δ [ppm]=1.38 (s, 9H), 5.62 (d, 1H), 7.35-7.45 (m, 2H), 7.61 (dd, 1H), 7.83 (d, 1H), 13.12 (br. s., 1H).

Example 27A tert-Butyl{2-[(1-amino-2-methyl-1-oxopropan-2-yl)amino]-1-(2,3-dichlorophenyl)-2-oxoethyl}carbamate

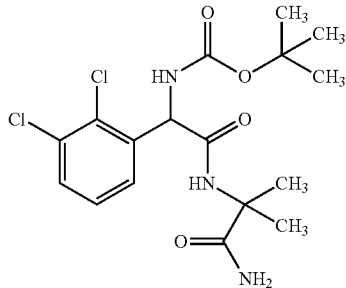 [SMILES: CC(C)(C)OC(=O)NC(C(=O)NC(C)(C)C(N)=O)c1cccc(Cl)c1Cl]

Analogously to Example 18A, 250 mg (0.78 mmol) of the compound of Example 26A and 119 mg (0.86 mmol) of 2-methylalaninamide hydrochloride gave 250 mg (77% of theory) of the title compound.

LC-MS [Method 3]: $R_t$=1.11 min; MS [ESIpos]: m/z=404 $(M+H)^+$.

$^1$H-NMR (400 MHz, DMSO-$d_6$): δ [ppm]=1.34-1.43 (m, 15H), 5.45 (d, 1H), 7.05 (br. s., 1H), 7.10 (br. s., 1H), 7.32-7.39 (m, 2H), 7.56-7.61 (m, 1H), 7.81 (d, 1H), 8.15 (s, 1H).

Example 28A

Methyl N-{(3S)-3-[(cert-butoxycarbonyl)amino]-3-[3-(trifluoromethyl)phenyl]propanoyl}-2-methylalaninate

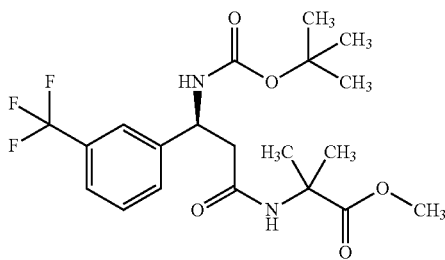 [SMILES: COC(=O)C(C)(C)NC(=O)C[C@H](NC(=O)OC(C)(C)C)c1cccc(C(F)(F)F)c1]

Analogously to Example 18A, 125 mg (0.38 mmol) of (3S)-3-[(tert-butoxycarbonyl)amino]-3-[3-(trifluoromethyl)phenyl]propanoic acid and 86 mg (0.56 mmol) of methyl 2-methylalaninate hydrochloride gave 130 mg (80% of theory) of the title compound.

LC-MS [Method 3]: $R_t$=1.26 min; MS [ESIpos]: m/z=433 $(M+H)^+$.

Example 29A tert-Butyl{2-[(1-hydroxy-2-methylpropan-2-yl)amino]-2-oxo-1-[3-(trifluoromethyl)phenyl]ethyl}-carbamate (racemate)

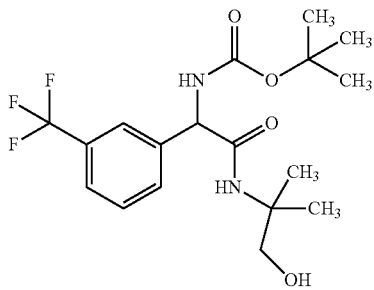 [SMILES: CC(C)(CO)NC(=O)C(NC(=O)OC(C)(C)C)c1cccc(C(F)(F)F)c1]

360 mg (1.88 mmol) of EDC were added to a mixture of 400 mg (1.25 mmol) of [(tert-butoxycarbonyl)amino][3-(trifluoromethyl)phenyl]acetic acid and 254 mg (1.88 mmol) of HOBt in 10 ml of DMF, and the mixture was stirred at RT for 20 min. The resulting solution was added dropwise to a solution of 168 mg (1.88 mmol) of 2-amino-2-methyl-1-propanol in 2 ml of DMF. The reaction mixture was stirred at RT for 20 min. For purification, 1 ml of 1N hydrochloric acid was added and the entire reaction mixture was separated by preparative HPLC [Method 6]. The appropriate fraction was concentrated on a rotary evaporator and the residue was dried under high vacuum. This gave 364 mg (74% of theory) of the title compound.

LC-MS [Method 3]: $R_t$=1.21 min; MS [ESIpos]: m/z=391 $(M+H)^+$ $^1$H-NMR (400 MHz, DMSO-$d_6$): δ [ppm]=1.13 (s, 3H), 1.14 (s, 3H), 1.38 (s, 9H), 3.26-3.32 (m, 1H), 3.41 (dd, 1H), 4.79 (t, 1H), 5.29 (d, 1H), 7.35 (d, 1H), 7.57 (t, 1H), 7.63 (d, 1H), 7.67-7.79 (m, 3H).

By chromatography on a chiral phase [Method 12], the title compound was separated into its enantiomers: see Examples 30A and 31A.

Example 30A tert-Butyl{2-[(1-hydroxy-2-methylpropan-2-yl)amino]-2-oxo-1-[3-(trifluoromethyl)-phenyl]ethyl}-carbamate (enantiomer 1)

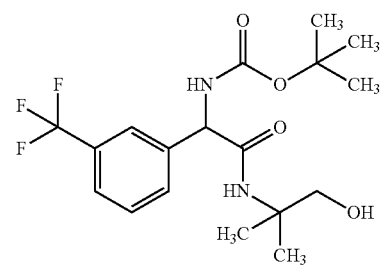 [SMILES: CC(C)(CO)NC(=O)C(NC(=O)OC(C)(C)C)c1cccc(C(F)(F)F)c1]

First-eluting enantiomer from the chromatographic enantiomer separation of the compound of Example 29A according to Method 12.

Chiral analytical HPLC [Method 13]: $R_t$=5.61 min

Example 31A tert-Butyl{2-[(1-hydroxy-2-methylpropan-2-yl)amino]-2-oxo-1-[3-(trifluoromethyl)-phenyl]ethyl}-carbamate (enantiomer 2)

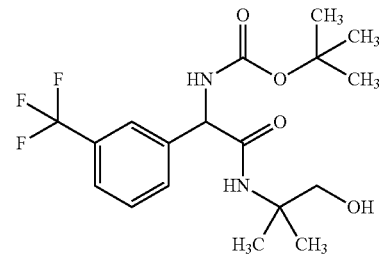 [SMILES: CC(C)(CO)NC(=O)C(NC(=O)OC(C)(C)C)c1cccc(C(F)(F)F)c1]

Last-eluting enantiomer from the chromatographic enantiomer separation of the compound of Example 29A according to Method 12.

Chiral analytical HPLC [Method 13]: $R_t$=4.85 min

Example 32A tert-Butyl{1-(2-chlorophenyl)-2-[(2-methoxyethyl)-amino]-2-oxoethyl}carbamate

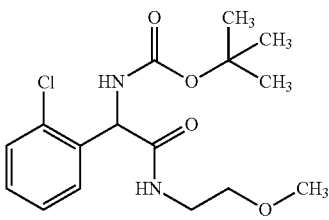 [SMILES: COCCNC(=O)C(NC(=O)OC(C)(C)C)c1ccccc1Cl]

A mixture of 250 mg (0.88 mmol) of [(tert-butoxycarbonyl)amino](2-chlorophenyl)acetic acid, 177 mg (1.31 mmol) of HOBt, 252 mg (1.31 mmol) of EDC and 72 mg (0.96 mmol) of 2-methoxyethanamine in 6.3 ml of DMF was stirred at RT for 2 h. For purification, 1 ml of 1N hydrochloric acid was added and the entire reaction mixture was separated by preparative HPLC [Method 6]. The appropriate fraction was concentrated on a rotary evaporator and the residue was dried under high vacuum. This gave 269 mg (90% of theory) of the title compound.

LC-MS [Method 5]: $R_t$=0.88 min; MS [ESIpos]: m/z=343 (M+H)$^+$ $^1$H-NMR (400 MHz, DMSO-d$_6$): δ [ppm]=1.38 (s, 9H), 3.18-3.29 (m, 2H), 3.22 (s, 3H), 3.29-3.37 (m, 2H), 5.45 (d, 1H), 7.28-7.34 (m, 2H), 7.35-7.46 (m, 2H), 7.49 (d, 1H), 8.06 (br. t, 1H).

Example 33A tert-Butyl{2-[(2-hydroxyethyl)amino]-2-oxo-1-[2-(trifluoromethyl)phenyl]ethyl}carbamate

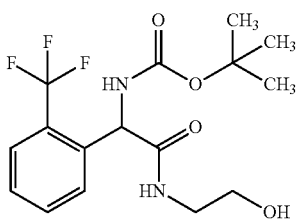 [SMILES: CC(C)(C)OC(=O)NC(C(=O)NCCO)c1ccccc1C(F)(F)F]

Analogously to Example 18A, but without N,N'-diisopropylethylamine, 500 mg (1.57 mmol) of [(tert-butoxycarbonyl)amino][2-(trifluoromethyl)phenyl]acetic acid and 287 mg (4.70 mmol) of 2-ethanolamine gave 540 mg (95% of theory) of the title compound.

LC-MS [Method 4]: $R_t$=2.04 min; MS [ESIpos]: m/z=363 (M+H)$^+$ $^1$H-NMR (400 MHz, DMSO-d$_6$): δ [ppm]=1.37 (br. s., 9H), 3.08-3.22 (m, 2H), 3.35-3.46 (m, 2H), 4.65 (t, 1H), 5.43 (d, 1H), 7.50 (t, 1H), 7.58 (d, 1H), 7.62-7.73 (m, 3H), 7.81-7.91 (m, 1H).

Example 34A tert-Butyl{2-[(2-methoxyethyl)amino]-2-oxo-1-[2-(trifluoromethyl)phenyl]ethyl}carbamate

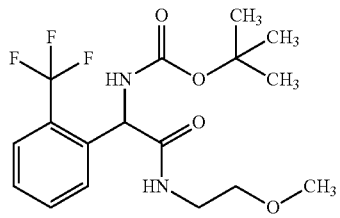 [SMILES: COCCNC(=O)C(NC(=O)OC(C)(C)C)c1ccccc1C(F)(F)F]

Analogously to Example 18A, but without N,N'-diisopropylethylamine, 500 mg (1.57 mmol) of [(tert-butoxycarbonyl)amino][2-(trifluoromethyl)phenyl]acetic acid and 176 mg (2.35 mmol) of 2-methoxyethanamine gave 510 mg (87% of theory) of the title compound.

LC-MS [Method 4]: $R_t$=2.28 min; MS [ESIpos]: m/z=377 (M+H)$^+$ $^1$H-NMR (400 MHz, DMSO-d$_6$): δ [ppm]=1.37 (br. s., 9H), 3.19-3.29 (m, 2H), 3.23 (s, 3H), 3.28-3.41 (m, 2H), 5.43 (d, 1H), 7.46-7.55 (m, 1H), 7.56-7.61 (m, 1H), 7.62-7.75 (m, 3H), 7.91-8.01 (m, 1H).

Example 35A tert-Butyl{2-[(2-hydroxyethyl)amino]-2-oxo-1-[3-(trifluoromethyl)phenyl]ethyl}carbamate

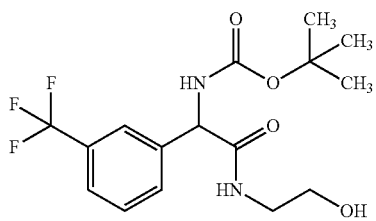 [SMILES: CC(C)(C)OC(=O)NC(C(=O)NCCO)c1cccc(C(F)(F)F)c1]

Analogously to Example 18A, but without N,N'-diisopropylethylamine, 319 mg (1.0 mmol) of [(tert-butoxycarbonyl)amino][3-(trifluoromethyl)phenyl]acetic acid and 183 mg (3.0 mmol) of 2-ethanolamine gave 210 mg (58% of theory) of the title compound.

LC-MS [Method 4]: $R_t$=1.05 min; MS [ESIpos]: m/z=363 (M+H)$^+$ $^1$H-NMR (400 MHz, DMSO-d$_6$): δ [ppm]=1.37 (d, 9H), 3.01-3.22 (m, 2H), 3.34-3.43 (m, 2H), 4.68 (t, 1H), 5.29 (d, 1H), 7.49 (d, 1H), 7.57 (t, 1H), 7.64 (d, 1H), 7.71 (d, 1H), 7.78 (s, 1H), 8.29 (t, 1H).

Example 36A

[(tert-Butoxycarbonyl)amino][3-(trifluoromethoxy)phenyl]acetic acid

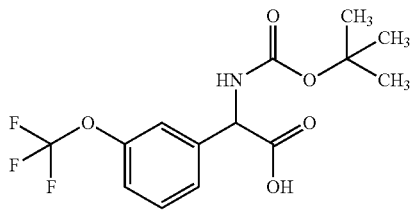 [SMILES: CC(C)(C)OC(=O)NC(C(=O)O)c1cccc(OC(F)(F)F)c1]

Analogously to Example 26A, 2.0 g (8.5 mmol) of 3-(trifluoromethoxy)-DL-phenylalanine were reacted with 1.89 g (8.68 mmol) of di-tert-butyl dicarbonate. This gave 3.0 g (quant.) of the title compound.

LC-MS [Method 4]: $R_t$=1.05 min; MS [ESIpos]: m/z=236 (M+H−BOC)$^+$; [ESIneg]: m/z=334 (M−H)$^-$.

$^1$H-NMR (400 MHz, DMSO-d$_6$): δ [ppm]=1.39 (s, 9H), 5.22 (d, 1H), 7.31 (d, 1H), 7.38-7.55 (m, 3H), 7.75 (d, 1H), 12.96 (br. s., 1H).

Example 37A tert-Butyl{2-[(2-hydroxyethyl)amino]-2-oxo-1-[3-(trifluoromethoxy)phenyl]ethyl}carbamate

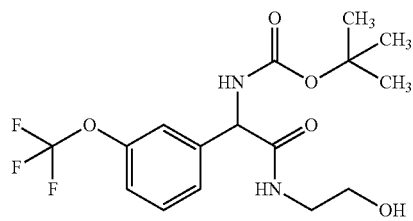 [SMILES: CC(C)(C)OC(=O)NC(C(=O)NCCO)c1cccc(OC(F)(F)F)c1]

Analogously to Example 18A, but without N,N'-diisopropylethylamine, 250 mg (0.75 mmol) of [(tert-butoxycarbonyl)amino][2-(trifluoromethoxy)phenyl]acetic acid and 55 mg (0.90 mmol) of 2-ethanolamine gave 258 mg (91% of theory) of the title compound.

LC-MS [Method 3]: $R_t$=1.10 min; MS [ESIpos]: m/z=279 (M+H−BOC)$^+$; [ESIneg]: m/z=377 (M−H)$^-$.

$^1$H-NMR (400 MHz, DMSO-d$_6$): δ [ppm]=1.37 (s, 9H), 3.02-3.22 (m, 2H), 3.33-3.43 (m, 2H), 4.68 (t, 1H), 5.24 (d, 1H), 7.27 (d, 1H), 7.37-7.50 (m, 4H), 8.27 (t, 1H).

Example 38A tert-Butyl{(1S)-3-[(2-hydroxyethyl)amino]-3-oxo-1-[2-(trifluoromethyl)phenyl]propyl}carbamate

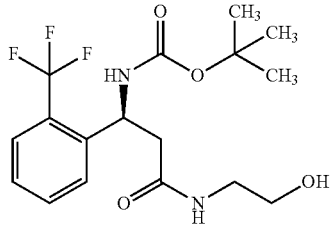 [SMILES: CC(C)(C)OC(=O)N[C@@H](CC(=O)NCCO)c1ccccc1C(F)(F)F]

Analogously to Example 32A, but with a reaction time of 15 h, 150 mg (0.45 mmol) of (3S)-3-[(tert-butoxycarbonyl)amino]-3-[2-(trifluoromethyl)phenyl]propanoic acid and 33 mg (0.54 mmol) of 2-aminoethanol gave 146 mg (86% of theory) of the title compound.

LC-MS [Method 1]: $R_t$=1.53 min; MS [ESIpos]: m/z=377 (M+H)$^+$ $^1$H-NMR (400 MHz, DMSO-d$_6$): δ [ppm]=1.32 (s, 9H), 2.24-2.34 (m, 2H), 3.02-3.19 (m, 2H), 3.34-3.41 (m, 2H), 4.64 (t, 1H), 5.20-5.30 (m, 1H), 7.39-7.55 (m, 2H), 7.61-7.73 (m, 5H).

Example 39A tert-Butyl{(1S)-3-[(2-hydroxyethyl)amino]-3-oxo-1-[3-(trifluoromethyl)phenyl]propyl}carbamate

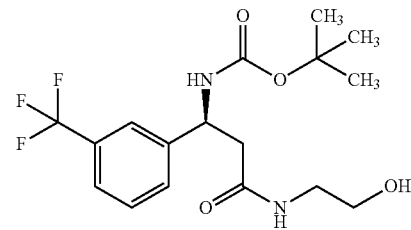 [SMILES: CC(C)(C)OC(=O)N[C@@H](CC(=O)NCCO)c1cccc(C(F)(F)F)c1]

Analogously to Example 18A, but without N,N'-diisopropylethylamine, 166 mg (0.50 mmol) of (3S)-3-[(tert-butoxycarbonyl)amino]-3-[3-(trifluoromethyl)phenyl]propanoic acid and 76 mg (1.24 mmol) of 2-aminoethanol gave 179 mg (94% of theory) of the title compound.

LC-MS [Method 4]: $R_t$=2.00 min; MS [ESIpos]: m/z=377 (M+H)$^+$ $^1$H-NMR (400 MHz, DMSO-d$_6$): δ [ppm]=1.35 (s, 9H), 3.03 (q, 2H), 3.21-3.31 (m, 2H), 4.58 (t, 1H), 4.98 (q, 1H), 7.50-7.64 (m, 5H), 7.84 (t, 1H).

Example 40A tert-Butyl{(1S)-3-[(2-methoxyethyl)amino]-3-oxo-1-[2-(trifluoromethyl)phenyl]propyl}carbamate

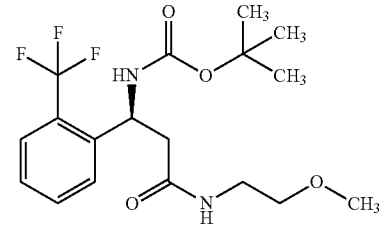 [SMILES: COCCNC(=O)C[C@H](NC(=O)OC(C)(C)C)c1ccccc1C(F)(F)F]

Analogously to Example 32A, but with a reaction time of 15 h, 142 mg (0.43 mmol) of (3S)-3-[(tert-butoxycarbonyl)amino]-3-[2-(trifluoromethyl)phenyl]propanoic acid and 38 mg (0.51 mmol) of 2-methoxyethanamine gave 133 mg (80% of theory) of the title compound.

LC-MS [Method 1]: $R_t$=1.76 min; MS [ESIpos]: m/z=391 (M+H)$^+$ $^1$H-NMR (400 MHz, DMSO-d$_6$): δ [ppm]=1.32 (s, 9H), 2.23-2.35 (m, 2H), 3.13-3.25 (m, 2H), 3.23 (s, 3H), 3.30 (t, 2H), 5.19-5.30 (m, 1H), 7.40-7.52 (m, 2H), 7.62-7.70 (m, 3H), 7.76 (br. t, 1H).

Example 41A tert-Butyl{(1S)-3-[(2-methoxyethyl)amino]-3-oxo-1-[3-(trifluoromethyl)phenyl]propyl}carbamate

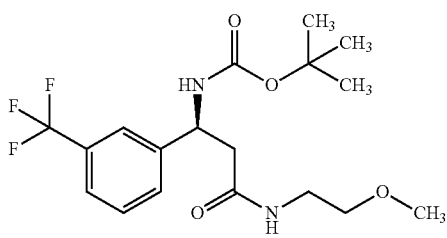 [SMILES: COCCNC(=O)C[C@H](NC(=O)OC(C)(C)C)c1cccc(C(F)(F)F)c1]

Analogously to Example 18A, but without N,N'-diisopropylethylamine, 150 mg (0.45 mmol) of (3S)-3-[(tert-butoxycarbonyl)amino]-3-[3-(trifluoromethyl)phenyl]propanoic acid and 41 mg (0.54 mmol) of 2-methoxyethanamine gave 167 mg (95% of theory) of the title compound.

LC-MS [Method 4]: $R_t$=2.20 min; MS [ESIpos]: m/z=391 (M+H)[30]

$^1$H-NMR (400 MHz, DMSO-$d_6$): δ [ppm]=1.35 (s, 9H), about 2.52 (m, 2H, partially under the DMSO signal), 3.04-3.26 (m, 4H), 3.16 (s, 3H), 4.97 (br. q, 1H), 7.46-7.66 (m, 5H), 7.93 (t, 1H).

Example 42A tert-Butyl(2-oxo-2-{[2-(trifluoromethoxy)ethyl]amino}-1-[3-(trifluoromethyl)phenyl]ethyl)-carbamate (racemate)

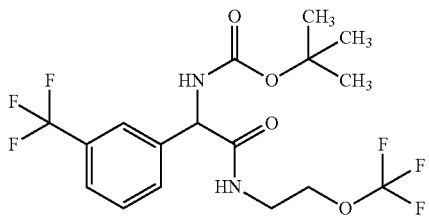 [SMILES: CC(C)(C)OC(=O)NC(C(=O)NCCOC(F)(F)F)c1cccc(C(F)(F)F)c1]

Analogously to Example 18A, 250 mg (0.78 mmol) of [(tert-butoxycarbonyl)amino][3-(trifluoromethyl)phenyl]acetic acid and 156 mg (0.94 mmol) of 2-(trifluoromethoxy)ethanamine hydrochloride gave 320 mg (95% of theory) of the title compound.

LC-MS [Method 4]: $R_t$=2.52 min; MS [ESIpos]: m/z=431 (M+H)$^+$ $^1$H-NMR (400 MHz, DMSO-$d_6$): δ [ppm]=1.38 (s, 9H), 3.27-3.48 (m, 2H), 3.94-4.07 (m, 2H), 5.29 (d, 1H), 7.53-7.60 (m, 2H), 7.62-7.67 (m, 1H), 7.70 (d, 1H), 7.78 (s, 1H), 8.53 (t, 1H).

By chromatography on a chiral phase [Method 14a], the title compound was separated into its two enantiomers: see Examples 43A and 44A.

Example 43A tert-Butyl(2-oxo-2-{[2-(trifluoromethoxy)ethyl]amino}-1-[3-(trifluoromethyl)phenyl]ethyl)-carbamate (enantiomer 1)

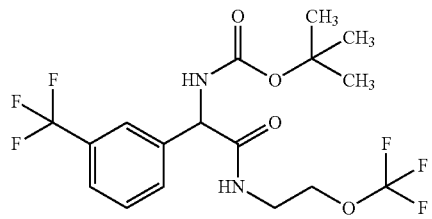 [SMILES: CC(C)(C)OC(=O)NC(C(=O)NCCOC(F)(F)F)c1cccc(C(F)(F)F)c1]

First-eluting enantiomer (150 mg) from the chromatographic enantiomer separation of the compound of Example 42A according to Method 14a.

Chiral analytical HPLC [Method 15a]: $R_t$=3.56 min

Example 44A tert-Butyl(2-oxo-2-{[2-(trifluoromethoxy)ethyl]amino}-1-[3-(trifluoromethyl)phenyl]ethyl)-carbamate (enantiomer 2)

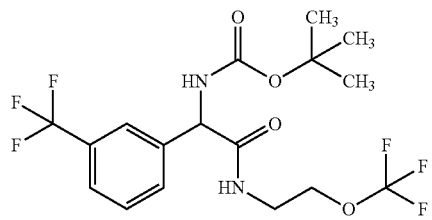 [SMILES: CC(C)(C)OC(=O)NC(C(=O)NCCOC(F)(F)F)c1cccc(C(F)(F)F)c1]

Last-eluting enantiomer (128 mg) from the chromatographic enantiomer separation of the compound of Example 42A according to Method 14a.

Chiral analytical HPLC [Method 15a]: $R_t$=3.89 min

Example 45A

Ethyl 1-({amino[3-(trifluoromethyl)phenyl]acetyl}amino)cyclopropanecarboxylate hydrochloride

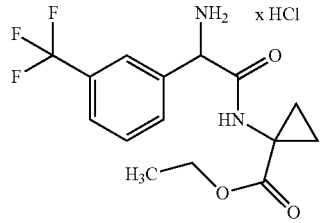 [SMILES: CCOC(=O)C1(NC(=O)C(N)c2cccc(C(F)(F)F)c2)CC1]

262 mg (0.61 mmol) of the compound of Example 17A were dissolved in 4 ml of dichloromethane, and 4 ml of a 4N solution of hydrogen chloride in dioxane were added. The solution was stirred at RT for 3 h and then freed from the volatile components on a rotary evaporator. The residue was dried under high vacuum. This gave 223 mg (quant.) of the title compound.

LC-MS [Method 3]: $R_t$=0.79 min; MS [ESIpos]: m/z=331 (M+H)$^+$

¹H-NMR (400 MHz, DMSO-d₆): δ [ppm]=0.95 (t, 3H), 0.97-1.08 (m, 2H), 1.27-1.34 (m, 1H), 1.46-1.53 (m, 1H), 3.85-3.99 (m, 2H), 5.08 (s, 1H), 7.73 (t, 1H), 7.81-7.87 (m, 2H), 7.95 (s, 1H), 8.73 (br. s., 3H), 9.24 (s, 1H).

Examples 46A to 61A in Table 1 were prepared by the same method. The reaction times to complete conversion were between 0.5 h and 16 h. The yields are greater than 90% of theory.

TABLE 1

| Example No. | Structure | Starting material | Name of the example and analytical data |
|---|---|---|---|
| 46A | 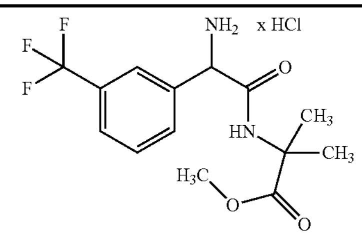 | 18A | methyl N-{amino[3-(trifluoromethyl)-phenyl]acetyl}-2-methylalaninate hydrochloride<br>LC-MS [Method 2]: R$_t$ = 1.32 min;<br>MS [ESIpos]: m/z = 319 (M + H)⁺ |
| 47A | 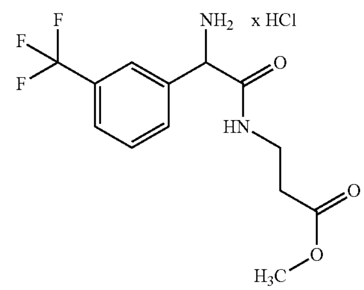 [SMILES: COC(=O)CCNC(=O)C(N)c1cccc(C(F)(F)F)c1 ; "x HCl"] | 19A | methyl N-{amino[3-(trifluoromethyl)-phenyl]acetyl}-beta-alaninate hydrochloride<br>LC-MS [Method 3]: R$_t$ = 0.66 min;<br>MS [ESIpos]: m/z = 305 (M + H)⁺ |
| 48A | 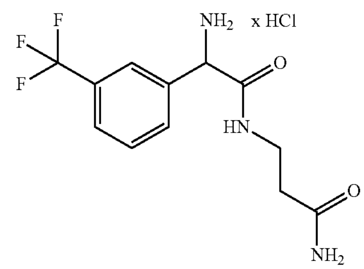 [SMILES: NC(=O)CCNC(=O)C(N)c1cccc(C(F)(F)F)c1 ; "x HCl"] | 21A | N3-{amino[3-(trifluoromethyl)-phenyl]acetyl}-beta-alaninamide hydrochloride (enantiomer 1)<br>LC-MS [Method 3]: R$_t$ = 0.28 min;<br>MS [ESIpos]: m/z = 290 (M + H)⁺ |
| 49A | 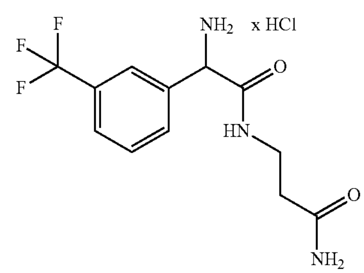 [SMILES: NC(=O)CCNC(=O)C(N)c1cccc(C(F)(F)F)c1 ; "x HCl"] | 22A | N3-{amino[3-(trifluoromethyl)-phenyl]acetyl}-beta-alaninamide hydrochloride (enantiomer 2)<br>LC-MS [Method 2]: R$_t$ = 0.86 min;<br>MS [ESIpos]: m/z = 290 (M + H)⁺ |
| 50A | 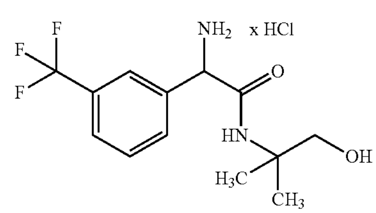 [SMILES: CC(C)(CO)NC(=O)C(N)c1cccc(C(F)(F)F)c1 ; "x HCl"] | 30A | 2-amino-N-(1-hydroxy-2-methylpropan-2-yl)-2-[3-(trifluoromethyl)phenyl]acetamide hydrochloride (enantiomer 1)<br>LC-MS [Method 2]: R$_t$ = 1.22 min;<br>MS [ESIpos]: m/z = 291 (M + H)⁺ |
| 51A | 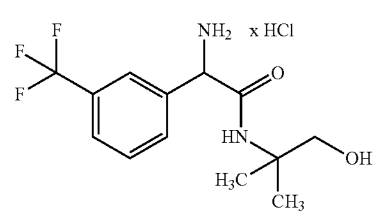 [SMILES: CC(C)(CO)NC(=O)C(N)c1cccc(C(F)(F)F)c1 ; "x HCl"] | 31A | 2-amino-N-(1-hydroxy-2-methylpropan-2-yl)-2-[3-(trifluoromethyl)phenyl]acetamide hydrochloride (enantiomer 2)<br>LC-MS [Method 2]: R$_t$ = 1.22 min;<br>MS [ESIpos]: m/z = 291 (M + H)⁺ |

TABLE 1-continued

| Example No. | Structure | Starting material | Name of the example and analytical data |
|---|---|---|---|
| 52A | 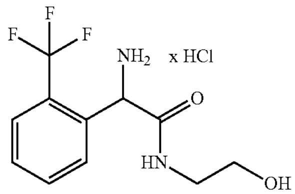 [SMILES: NC(C(=O)NCCO)c1ccccc1C(F)(F)F ; "x HCl"] | 33A | 2-amino-N-(2-hydroxyethyl)-2-[2-(trifluoromethyl)phenyl]acetamide hydrochloride (purity 75%)<br>LC-MS [Method 2]: $R_t$ = 0.22 min;<br>MS [ESIpos]: m/z = 263 (M + H)$^+$ |
| 53A | 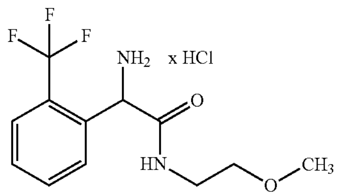 [SMILES: COCCNC(=O)C(N)c1ccccc1C(F)(F)F ; "x HCl"] | 34A | 2-amino-N-(2-methoxyethyl)-2-[2-(trifluoromethyl)phenyl]acetamide hydrochloride<br>LC-MS [Method 2]: $R_t$ = 0.93 min;<br>MS [ESIpos]: m/z = 277 (M + H)$^+$ |
| 54A | 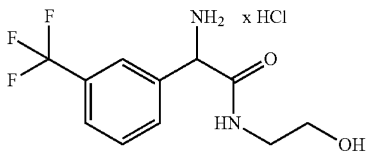 [SMILES: NC(C(=O)NCCO)c1cccc(C(F)(F)F)c1 ; "x HCl"] | 35A | 2-amino-N-(2-hydroxyethyl)-2-[3-(trifluoromethyl)phenyl]acetamide hydrochloride<br>LC-MS [Method 2]: $R_t$ = 0.97 min;<br>MS [ESIpos]: m/z = 263 (M + H)$^+$ |
| 55A | 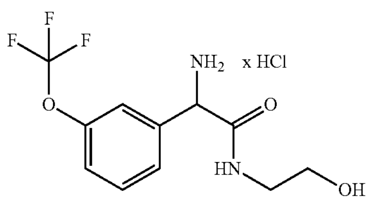 [SMILES: NC(C(=O)NCCO)c1cccc(OC(F)(F)F)c1 ; "x HCl"] | 37A | 2-amino-N-(2-hydroxyethyl)-2-[3-(trifluoromethoxy)phenyl]acetamide hydrochloride<br>LC-MS [Method 2]: $R_t$ = 1.01 min;<br>MS [ESIpos]: m/z = 279 (M + H)$^+$ |
| 56A | 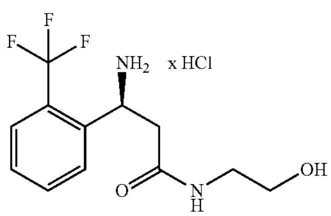 [SMILES: N[C@@H](CC(=O)NCCO)c1ccccc1C(F)(F)F ; "x HCl"] | 38A | (3S)-3-amino-N-(2-hydroxyethyl)-3-[2-(trifluoromethyl)phenyl]-propanamide hydrochloride<br>LC-MS [Method 3]: $R_t$ = 0.30 min;<br>MS [ESIpos]: m/z = 277 (M + H)$^+$ |
| 57A | 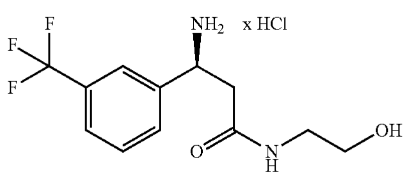 [SMILES: N[C@@H](CC(=O)NCCO)c1cccc(C(F)(F)F)c1 ; "x HCl"] | 39A | (3S)-3-amino-N-(2-hydroxyethyl)-3-[3-(trifluoromethyl)phenyl]-propanamide hydrochloride<br>LC-MS [Method 2]: $R_t$ = 0.90 min;<br>MS [ESIpos]: m/z = 277 (M + H)$^+$ |
| 58A | 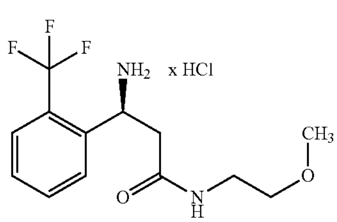 [SMILES: COCCNC(=O)C[C@H](N)c1ccccc1C(F)(F)F ; "x HCl"] | 40A | (3S)-3-amino-N-(2-methoxyethyl)-3-[2-(trifluoromethyl)phenyl]-propanamide hydrochloride<br>LC-MS [Method 3]: $R_t$ = 0.52 min;<br>MS [ESIpos]: m/z = 291 (M + H)$^+$ |
| 59A | 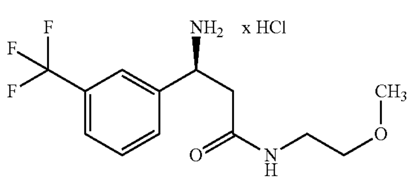 [SMILES: COCCNC(=O)C[C@H](N)c1cccc(C(F)(F)F)c1 ; "x HCl"] | 41A | (3S)-3-amino-N-(2-methoxyethyl)-3-[3-(trifluoromethyl)phenyl]-propanamide hydrochloride<br>LC-MS [Method 3]: $R_t$ = 0.62 min;<br>MS [ESIpos]: m/z = 291 (M + H)$^+$ |

TABLE 1-continued

| Example No. | Structure | Starting material | Name of the example and analytical data |
|---|---|---|---|
| 60A | (structure) | 43A | 2-amino-N-[2-(trifluoromethoxy)-ethyl]-2-[3-(trifluoromethyl)phenyl]-acetamide hydrochloride (enantiomer 1)<br>LC-MS [Method 3]: $R_t$ = 0.81 min;<br>MS [ESIpos]: m/z = 331 (M + H)$^+$ |
| 61A | (structure) | 44A | 2-amino-N-[2-(trifluoromethoxy)-ethyl]-2-[3-(trifluoromethyl)phenyl]-acetamide hydrochloride (enantiomer 2)<br>LC-MS [Method 3]: $R_t$ = 0.81 min;<br>MS [ESIpos]: m/z = 331 (M + H)$^+$ |

Example 62A

$N^2$-{Amino[2-(trifluoromethyl)phenyl]acetyl}-2-methylalaninamide hydrochloride

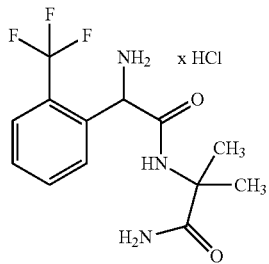 [SMILES: CC(C)(NC(=O)C(N)c1ccccc1C(F)(F)F)C(N)=O]

4.45 ml of a 4N solution of hydrogen chloride in dioxane were added to 922 mg (0.48 mmol) of the compound of Example 24A. The solution was stirred at RT for 1 h and then freed from the volatile components on a rotary evaporator. The residue was stirred with 10 ml of diethyl ether. The solid was isolated by filtration and dried under high vacuum. This gave 167 mg (96% of theory) of the title compound.

LC-MS [Method 5]: $R_t$=0.36 min; MS [ESIpos]: m/z=304 (M+H)$^+$.

$^1$H-NMR (400 MHz, DMSO-$d_6$): δ [ppm]=1.34 (s, 3H), 1.40 (s, 3H), 5.14 (s, 1H), 7.13 (s, 1H), 7.37 (s, 1H), 7.68 (t, 1H), 7.75-7.89 (m, 3H), 8.21 (br. s., 1H), 8.94 (br. s., 3H).

Examples 63A to 66A in Table 2 were prepared analogously to Example 62A. The yields are in each case greater than 90% of theory.

TABLE 2

| Example No. | Structure | Starting material | Name of the example and analytical data |
|---|---|---|---|
| 63A | (structure) | 23A | $N^2$-{amino[3-(trifluoromethyl)-phenyl]acetyl}-2-methylalaninamide hydrochloride<br>LC-MS [Method 2]: $R_t$ = 1.05 min;<br>MS [ESIpos]: m/z = 304 (M + H)$^+$ |
| 64A | (structure) | 25A | $N^2$-[amino(2-chlorophenyl)acetyl]-2-methylalaninamide hydrochloride<br>LC-MS [Method 5]: $R_t$ = 0.26 min;<br>MS [ESIpos]: m/z = 270 (M + H)$^+$ |

TABLE 2-continued

| Example No. | Structure | Starting material | Name of the example and analytical data |
|---|---|---|---|
| 65A | 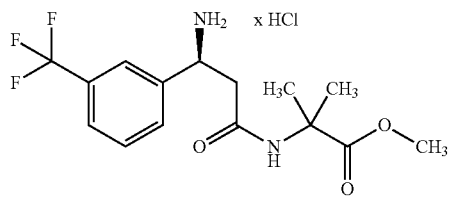 | 27A | $N^2$-[amino(2,3-dichlorophenyl)-acetyl]-2-methylalaninamide hydrochloride<br>LC-MS [Method 5]: $R_t$ = 0.44 min; MS [ESIpos]: m/z = 304 (M + H)$^+$ |
| 66A | 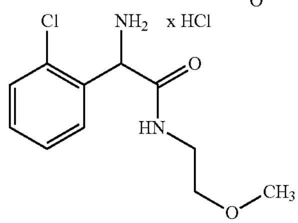 | 32A | 2-amino-2-(2-chlorophenyl)-N-(2-methoxyethyl)acetamide hydrochloride<br>LC-MS [Method 5]: $R_t$ = 0.29 min; MS [ESIpos]: m/z = 243 (M + H)$^+$ |

Example 67A

Methyl N-{(3S)-3-amino-3-[3-(trifluoromethyl)phenyl]propanoyl}-2-methylalaninate 130 mg (0.30 mmol) of the compound of Example 28A were dissolved in 2 ml of acetonitrile, and 2 ml of a 4N solution of hydrogen chloride in dioxane were added. The solution was stirred at RT for 3 h and then freed from the volatile components on a rotary evaporator. The residue was dried under high vacuum. This gave 108 mg (97% of theory) of the title compound.

LC-MS [Method 3]: $R_t$=0.75 min; MS [ESIpos]: m/z=333 (M+H)$^+$.

$^1$H-NMR (400 MHz, DMSO-d$_6$): δ [ppm]=1.16 (s, 3H), 1.24 (s, 3H), 2.78-2.91 (m, 2H), 3.41 (s, 3H), 4.66-4.76 (m, 1H), 7.63-7.70 (m, 1H), 7.73-7.81 (m, 2H), 7.87 (s, 1H), 8.48-8.68 (m, 4H).

Working Examples

Example 1

Ethyl 1-({[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylate (diastereomer mixture)

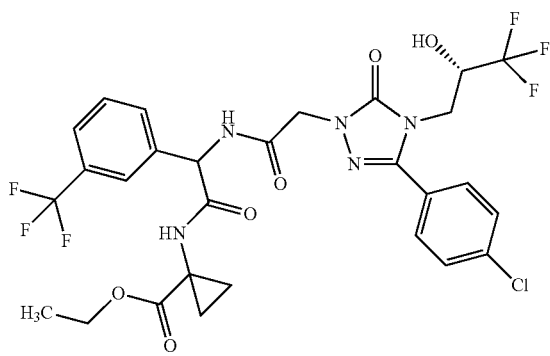 [SMILES: CCOC(=O)C1(NC(=O)C(NC(=O)Cn2nc(-c3ccc(Cl)cc3)n(C[C@H](O)C(F)(F)F)c2=O)c2cccc(C(F)(F)F)c2)CC1]

A mixture of 50 mg (0.14 mmol) of the compound of Example 8A, 55 mg (0.15 mmol) of the compound of Example 45A, 39 mg (0.21 mmol) of EDC, 28 mg (0.21 mmol) of HOBt and 29 µl (0.16 mmol) of N,N'-diisopropylethylamine in 1.4 ml of DMF was stirred at RT for 3 h and then separated by preparative HPLC [Method 6]. The suitable fraction was concentrated on a rotary evaporator and the residue was dried under high vacuum. This gave 82 mg (88% of theory) of the title compound as a diastereomer mixture.

LC-MS [Method 3]: $R_t$=1.31 min; MS [ESIpos]: m/z=678 (M+H)$^+$ $^1$H-NMR (400 MHz, DMSO-d$_6$): δ [ppm]=0.91 (td interpreted as 1 t each per diastereomer, 3H), 0.95-1.08 (m, 2H), 1.25-1.33 (m, 1H), 1.38-1.46 (m, 1H), 3.78-4.01 (m, 4H), 4.18-4.33 (m, 1H), 4.52-4.65 (m, 2H), 5.54 (d, 1H), 6.89 (dd interpreted as 1 d each per diastereomer, 1H), 7.58-7.65 (m, 3H), 7.66-7.71 (m, 1H), 7.71-7.77 (m, 3H), 7.82 (s, 1H), 9.07 (d, 1H), 9.09 (s, 1H).

Example 2

1-({[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylic acid (diastereomer mixture)

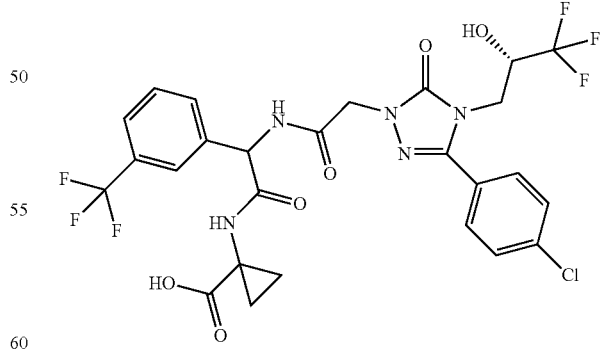

78 mg (0.115 mmol) of the compound of Example 1 were dissolved in 2.2 ml of methanol, and 460 µl of a 1M aqueous lithium hydroxide solution (0.46 mmol) were added. The mixture was stirred at RT overnight and then adjusted to pH 2 by addition of 1N hydrochloric acid, diluted with a little DMSO and separated by preparative HPLC [Method 6]. This gave 64 mg (86% of theory) of the title compound.

LC-MS [Method 3]: $R_t$=1.19 min; MS [ESIpos]: m/z=650 (M+H)$^+$

By preparative HPLC on a chiral phase [Method 14a], the two diastereomers were separated: see Example 3 and Example 4.

Example 3

1-({[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylic acid (diastereomer 1)

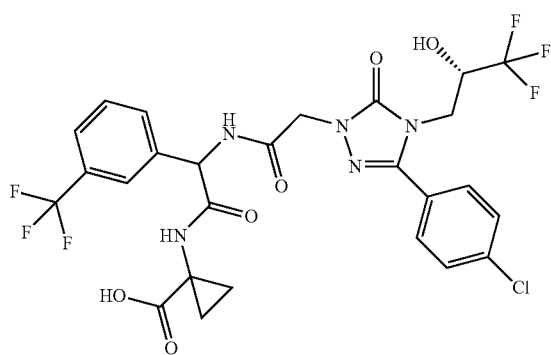 [SMILES: O=C(Cn1nc(-c2ccc(Cl)cc2)n(C[C@H](O)C(F)(F)F)c1=O)NC(C(=O)NC1(C(=O)O)CC1)c1cccc(C(F)(F)F)c1]

First-eluting diastereomer from the diastereomer separation of 64 mg of the compound of Example 2 according to Method 14a. After chromatography on the chiral phase, the product obtained was purified from solvent contaminants by preparative HPLC [Method 6]. This gave 14 mg of the title compound.

Chiral analytical HPLC [Method 15a]: $R_t$=4.60 min
LC-MS [Method 1]: $R_t$=1.92 min; MS [ESIpos]: m/z=650 (M+H)$^+$
$^1$H-NMR (400 MHz, DMSO-d$_6$): δ [ppm]=0.84-0.93 (m, 1H), 0.93-1.02 (m, 1H), 1.25-1.42 (m, 2H), 3.82 (dd, 1H), 3.96 (dd, 1H), 4.20-4.34 (m, 1H), 4.52-4.65 (m [AB], 2H), 5.55 (d, 1H), 6.91 (br. d, 1H), 7.55-7.78 (m, 6H), 7.82 (s, 1H), 8.99-9.07 (m, 2H), 12.43 (s, 1H).

Example 4

1-({[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}amino)cyclopropanecarboxylic acid (diastereomer 2)

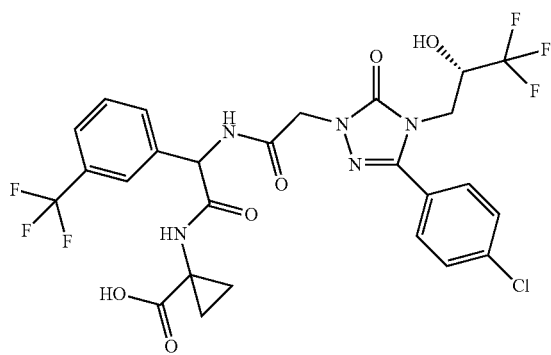 [SMILES: O=C(Cn1nc(-c2ccc(Cl)cc2)n(C[C@H](O)C(F)(F)F)c1=O)NC(C(=O)NC1(C(=O)O)CC1)c1cccc(C(F)(F)F)c1]

Last-eluting diastereomer from the diastereomer separation of 64 mg of the compound of Example 2 according to Method 14a. After chromatography on the chiral phase, the product obtained was purified from solvent contaminants by preparative HPLC [Method 6]. This gave 16 mg of the title compound.

Chiral analytical HPLC [Method 15a]: $R_t$=5.85 min
LC-MS [Method 1]: $R_t$=1.91 min; MS [ESIpos]: m/z=650 (M+H)$^+$
$^1$H-NMR (400 MHz, DMSO-d$_6$): δ [ppm]=0.83-0.92 (m, 1H), 0.93-1.02 (m, 1H), 1.25-1.42 (m, 2H), 3.82 (dd, 1H), 3.96 (dd, 1H), 4.20-4.34 (m, 1H), 4.52-4.67 (m [AB], 2H), 5.55 (d, 1H), 6.89 (d, 1H), 7.55-7.78 (m, 7H), 7.83 (s, 1H), 8.89-9.14 (m, 2H), 12.43 (s, 1H).

Example 5

Ethyl 1-({({[3-(4-chlorophenyl)-4-cyclopropyl-5-oxo-4,5-dihydro-1H-1,2,4-triazol-1-yl]acetyl}-amino) [3-(trifluoromethyl)phenyl]acetyl}amino)cyclopropanecarboxylate (racemate)

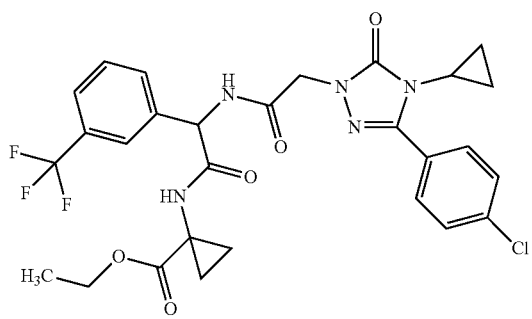 [SMILES: CCOC(=O)C1(NC(=O)C(NC(=O)Cn2nc(-c3ccc(Cl)cc3)n(C3CC3)c2=O)c2cccc(C(F)(F)F)c2)CC1]

Analogously to Example 1, 50 mg (0.17 mmol) of [3-(4-chlorophenyl)-4-cyclopropyl-5-oxo-4,5-dihydro-1H-1,2,4-triazol-1-yl]acetic acid (for the preparation, see WO 2007/134862, Example 88A) and 69 mg (0.19 mmol) of the compound of Example 45A were used to prepare the title compound. This gave 83 mg (80% of theory) of the title compound.

LC-MS [Method 3]: $R_t$=1.27 min; MS [ESIpos]: m/z=606 (M+H)$^+$
$^1$H-NMR (400 MHz, DMSO-d$_6$): δ [ppm]=0.51-0.60 (m, 2H), 0.85-0.92 (m, 2H), 0.91 (t, 3H), 0.94-1.08 (m, 2H), 1.24-1.33 (m, 1H), 1.38-1.46 (m, 1H), 3.17 (tt, 1H), 3.82-3.98 (m, 2H), 4.45-4.59 (m [AB], 2H), 5.52 (d, 1H), 7.54-7.65 (m, 3H), 7.65-7.71 (m, 1H), 7.71-7.84 (m, 4H), 9.03 (d, 1H), 9.08 (s, 1H).

Example 6

1-({({[3-(4-Chlorophenyl)-4-cyclopropyl-5-oxo-4,5-dihydro-1H-1,2,4-triazol-1-yl]acetyl}-amino)[3-(trifluoromethyl)phenyl}acetyl]amino)cyclopropanecarboxylic acid (racemate)

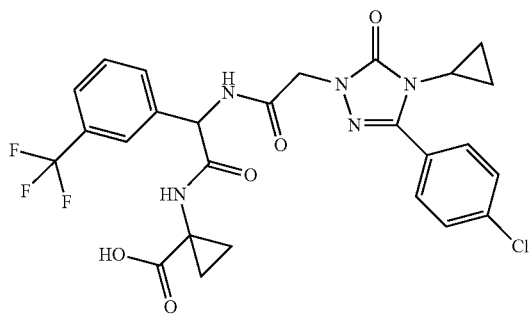 [SMILES: O=C(Cn1nc(-c2ccc(Cl)cc2)n(C2CC2)c1=O)NC(C(=O)NC1(C(=O)O)CC1)c1cccc(C(F)(F)F)c1]

64 mg (0.106 mmol) of the compound of Example 5 were dissolved in 3 ml of methanol, and 422 μl of a 1M aqueous lithium hydroxide solution (0.42 mmol) were added. The mixture was stirred at RT overnight. Since the reaction was very slow, another 210 μl (0.21 mmol) of a 1M sodium hydroxide solution were added and the mixture was stirred at RT for another 5 days. By addition of 1N hydrochloric acid, the mixture was adjusted to pH 2, diluted with a little DMSO and separated by preparative HPLC [Method 6]. This gave 37 mg (61% of theory) of the title compound.

LC-MS [Method 3]: $R_t$=1.15 min; MS [ESIpos]: m/z=578 (M+H)$^+$ $^1$H-NMR (400 MHz, DMSO-$d_6$): δ [ppm]=0.51-0.61 (m, 2H), 0.83-0.93 (m, 3H), 0.94-1.02 (m, 1H), 1.25-1.41 (m, 2H), 3.17 (tt, 1H), 4.47-4.58 (m [AB], 2H), 5.54 (d, 1H), 7.55-7.62 (m, 3H), 7.64-7.68 (m, 1H), 7.70 (d, 1H), 7.76-7.84 (m, 3H), 8.98 (d, 1H), 9.01 (s, 1H), 12.43 (br. s., 1H).

Example 7

Ethyl 1-({({[3-(5-chloro-2-thienyl)-4-(2-methoxy-ethyl)-5-oxo-4,5-dihydro-1H-1,2,4-triazol-1-yl]acetyl}amino) [3-(trifluoromethyl)phenyl]acetyl}amino)cyclopropanecarboxylate (racemate)

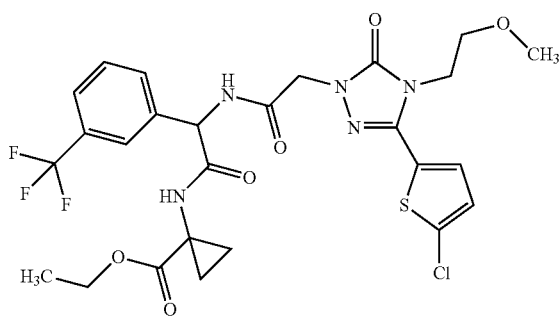 [SMILES: CCOC(=O)C1(NC(=O)C(NC(=O)Cn2nc(-c3ccc(Cl)s3)n(CCOC)c2=O)c2cccc(C(F)(F)F)c2)CC1]

Analogously to Example 1, 25 mg (79 μmol) of the compound of Example 15A and 32 mg (87 μmol) of the compound of Example 45A were employed. Purification by HPLC [Method 7] gave 47 mg (95% of theory) of the title compound.

LC-MS [Method 5]: $R_t$=1.05 min; MS [ESIpos]: m/z=630 (M+H)$^+$ $^1$H-NMR (400 MHz, DMSO-$d_6$): δ [ppm]=0.91 (t, 3H), 0.95-1.09 (m, 2H), 1.24-1.32 (m, 1H), 1.38-1.46 (m, 1H), 3.19 (s, 3H), 3.53 (t, 2H), 3.84-3.94 (m, 2H), 3.96 (t, 2H), 4.49-4.60 (m [AB], 2H), 5.53 (d, 1H), 7.26 (d, 1H), 7.55 (d, 1H), 7.62 (t, 1H), 7.69 (d, 1H), 7.74 (d, 1H), 7.81 (s, 1H), 9.07 (d, 1H), 9.09 (s, 1H).

Example 8

1-({({[3-(5-Chloro-2-thienyl)-4-(2-methoxyethyl)-5-oxo-4,5-dihydro-1H-1,2,4-triazol-1-yl]acetyl}-amino)[3-(trifluoromethyl)phenyl]acetyl}amino)cyclopropanecarboxylic acid (racemate)

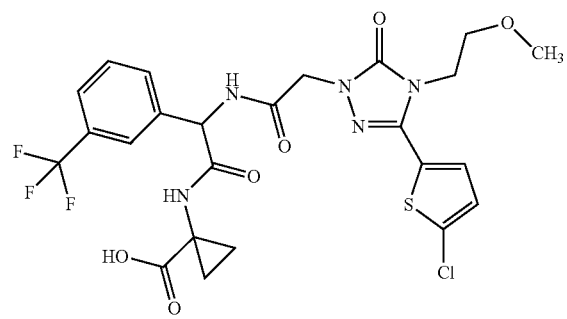 [SMILES: COCCn1c(-c2ccc(Cl)s2)nn(CC(=O)NC(C(=O)NC2(C(=O)O)CC2)c2cccc(C(F)(F)F)c2)c1=O]

43 mg (68 μmol) of the compound of Example 7 were dissolved in 3 ml of methanol, and 273 μl of a 1M aqueous lithium hydroxide solution (0.27 mmol) were added. The mixture was stirred at RT overnight and then acidified by addition of 1N hydrochloric acid and diluted with water. The precipitated solid was filtered off with suction, washed with a little water and dried in a vacuum drying cabinet at 50° C. This gave 32 mg (74% of theory) of the title compound.

LC-MS [Method 3]: $R_t$=1.16 min; MS [ESIpos]: m/z=602 (M+H)$^+$ $^1$H-NMR (400 MHz, DMSO-$d_6$): δ [ppm]=0.84-0.93 (m, 1H), 0.94-1.04 (m, 1H), 1.25-1.43 (m, 2H), 3.19 (s, 3H), 3.50-3.60 (m, 2H), 3.97 (t, 2H), 4.46-4.64 (m, 2H), 5.54 (d, 1H), 7.26 (d, 1H), 7.53-7.63 (m, 2H), 7.69 (dd, 2H), 7.82 (s, 1H), 8.98-9.08 (m, 2H), 12.44 (br. s., 1H).

Example 9

Methyl N-{({[3-(5-chloro-2-thienyl)-4-(2-methoxy-ethyl)-5-oxo-4,5-dihydro-1H-1,2,4-triazol-1-yl]acetyl}amino)[3-(trifluoromethyl)phenyl]acetyl}-2-methylalaninate (racemate)

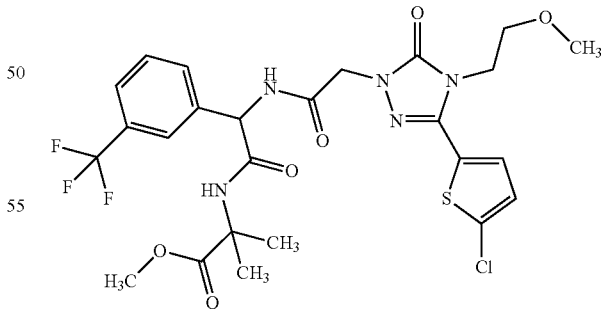

Analogously to Example 1, 25 mg (79 μmol) of the compound of Example 15A and 31 mg (87 μmol) of the compound of Example 46A were employed. Purification by HPLC [Method 7] gave 44 mg (90% of theory) of the title compound.

LC-MS [Method 5]: $R_t$=1.05 min; MS [ESIpos]: m/z=618 (M+H)$^+$

¹H-NMR (400 MHz, DMSO-d₆): δ [ppm]=1.27 (s, 3H), 1.40 (s, 3H), 3.20 (s, 3H), 3.44 (s, 3H), 3.54 (t, 2H), 3.97 (t, 2H), 4.49-4.61 (m, 2H), 5.63 (d, 1H), 7.26 (d, 1H), 7.56 (d, 1H), 7.59-7.65 (m, 1H), 7.66-7.72 (m, 2H), 7.76 (s, 1H), 8.84 (s, 1H), 9.02 (d, 1H).

Example 10

N-{({[3-(5-Chloro-2-thienyl)-4-(2-methoxyethyl)-5-oxo-4,5-dihydro-1H-1,2,4-triazol-1-yl]acetyl}-amino)[3-(trifluoromethyl)phenyl]acetyl}-2-methylalanine (racemate)

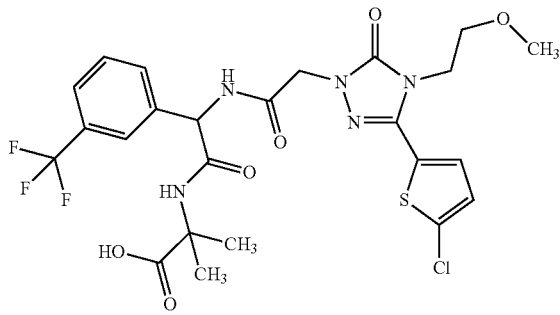 [SMILES: COCCn1c(-c2ccc(Cl)s2)nn(CC(=O)NC(C(=O)NC(C)(C)C(=O)O)c2cccc(C(F)(F)F)c2)c1=O]

Analogously to Example 8, 40 mg (65 μmol) of the compound of Example 9 were hydrolysed. This gave 31 mg (75% of theory) of the title compound.

LC-MS [Method 3]: $R_t$=1.20 min; MS [ESIpos]: m/z=604 (M+H)⁺

¹H-NMR (400 MHz, DMSO-d₆): δ [ppm]=1.27 (s, 3H), 1.38 (s, 3H), 3.20 (s, 3H), 3.54 (t, 2H), 3.97 (t, 2H), 4.49-4.61 (m, 2H), 5.65 (d, 1H), 7.26 (d, 1H), 7.54-7.62 (m, 2H), 7.63-7.73 (m, 2H), 7.79 (s, 1H), 8.68 (s, 1H), 9.00 (d, 1H), 12.28 (br. s., 1H).

Example 11

Methyl N-{({[3-(4-chlorophenyl)-4-cyclopropyl-5-oxo-4,5-dihydro-1H-1,2,4-triazol-1-yl]acetyl}-amino)[3-(trifluoromethyl)phenyl]acetyl}-2-methylalaninate (racemate)

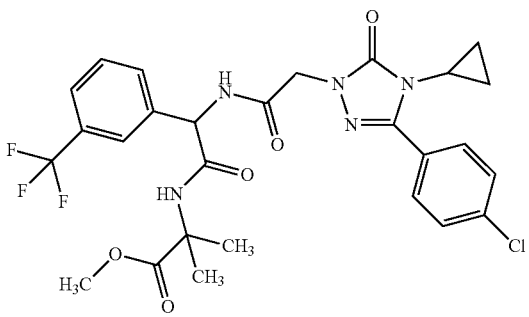 [SMILES: COC(=O)C(C)(C)NC(=O)C(NC(=O)Cn1nc(-c2ccc(Cl)cc2)n(C2CC2)c1=O)c1cccc(C(F)(F)F)c1]

Analogously to Example 1, 50 mg (0.17 mmol) of [3-(4-chlorophenyl)-4-cyclopropyl-5-oxo-4,5-dihydro-1H-1,2,4-triazol-1-yl]acetic acid (for the preparation, see WO 2007/134862, Example 88A) and 72 mg (0.19 mmol) of the compound of Example 46A were used to prepare the title compound. This gave 89 mg (88% of theory) of the title compound.

LC-MS [Method 3]: $R_t$=1.28 min; MS [ESIpos]: m/z=594 (M+H)⁺

¹H-NMR (400 MHz, DMSO-d₆): δ [ppm]=0.40-0.68 (m, 2H), 0.79-1.00 (m, 2H), 1.27 (s, 3H), 1.40 (s, 3H), 3.18 (dt, 1H), 3.44 (s, 3H), 4.46-4.58 (m [AB], 2H), 5.62 (d, 1H), 7.55-7.64 (m, 3H), 7.65-7.72 (m, 2H), 7.74-7.83 (m, 3H), 8.83 (s, 1H), 8.98 (d, 1H).

Example 12

N-{({[3-(4-Chlorophenyl)-4-cyclopropyl-5-oxo-4,5-dihydro-1H-1,2,4-triazol-1-yl]acetyl}amino)[3-(trifluoromethyl)phenyl]acetyl}-2-methylalanine (racemate)

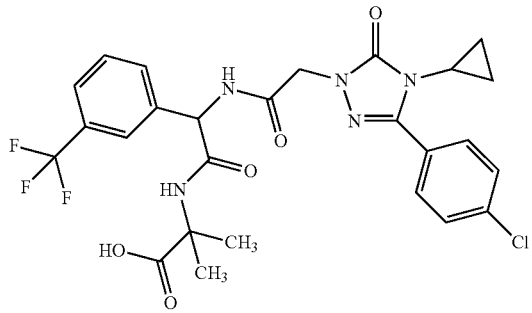 [SMILES: CC(C)(NC(=O)C(NC(=O)Cn1nc(-c2ccc(Cl)cc2)n(C2CC2)c1=O)c1cccc(C(F)(F)F)c1)C(=O)O]

Analogously to Example 6, 68 mg (114 μmol) of the compound of Example 9 were hydrolysed. This gave 55 mg (83% of theory) of the title compound.

LC-MS [Method 3]: $R_t$=1.19 min; MS [ESIpos]: m/z=580 (M+H)⁺

¹H-NMR (400 MHz, DMSO-d₆): δ [ppm]=0.51-0.62 (m, 2H), 0.84-0.94 (m, 2H), 1.27 (s, 3H), 1.38 (s, 3H), 3.18 (tt, 1H), 4.52 (s, 2H), 5.64 (d, 1H), 7.54-7.61 (m, 3H), 7.63-7.68 (m, 1H), 7.70 (d, 1H), 7.76-7.84 (m, 3H), 8.67 (s, 1H), 8.96 (d, 1H), 12.27 (s, 1H).

Example 13

Methyl N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninate (diastereomer mixture)

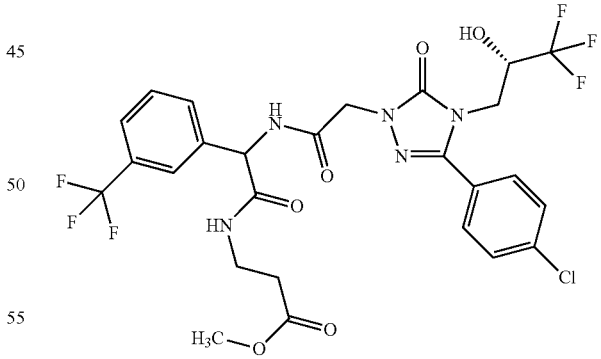

Analogously to Example 1, 50 mg (0.14 mmol) of the compound of Example 8A and 51 mg (0.15 mmol) of the compound of Example 47A were used to prepare the title compound. This gave 88 mg (99% of theory) of the title compound as a diastereomer mixture.

LC-MS [Method 3]: $R_t$=1.25 min; MS [ESIpos]: m/z=652 (M+H)⁺

¹H-NMR (400 MHz, DMSO-d₆): δ [ppm]=2.44 (t, 2H), 3.25-3.31 (m, 2H), 3.52 (s, 3H), 3.82 (dd, 1H), 3.91-4.00 (m, 1H), 4.19-4.33 (m, 1H), 4.52-4.66 (m, 2H), 5.55 (d, 1H), 6.89

Example 14

N-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alanine (diastereomer mixture)

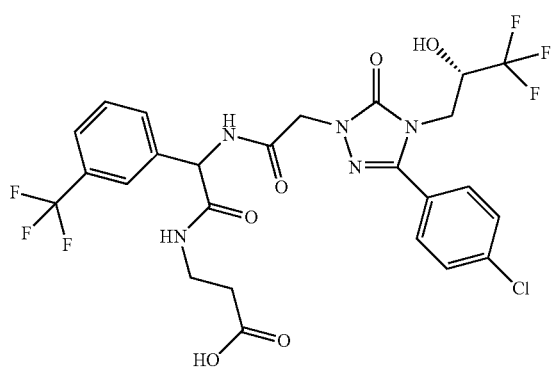 [SMILES: O=C(O)CCNC(=O)C(NC(=O)Cn1nc(-c2ccc(Cl)cc2)n(C[C@H](O)C(F)(F)F)c1=O)c1cccc(C(F)(F)F)c1]

78 mg (0.12 mmol) of the compound of Example 13 were dissolved in 2.3 ml of methanol, and 360 µl of a 1M aqueous lithium hydroxide solution (0.36 mmol) were added. The mixture was stirred at RT for 1 h and then adjusted to pH 2 by addition of 1N hydrochloric acid, diluted with a little DMSO and separated by preparative HPLC [Method 6]. This gave 67 mg (88% of theory) of the title compound.

LC-MS [Method 3]: $R_t$=1.17 min; MS [ESIpos]: m/z=638 (M+H)$^+$ $^1$H-NMR (400 MHz, DMSO-$d_6$): δ [ppm]=2.36 (t, 2H), 3.17-3.30 (m, 2H), 3.82 (dd, 1H), 3.96 (br. d, 1H), 4.17-4.35 (m, 1H), 4.50-4.68 (m, 2H), 5.57 (d, 1H), 6.89 (t interpreted as 1 d each per diastereomer, 1H), 7.52-7.82 (m, 8H), 8.59 (t interpreted as 1 d each per diastereomer, 1H), 9.04 (d, 1H), 12.23 (br. s., 1H).

Example 15

Methyl N-{({[3-(4-chlorophenyl)-4-cyclopropyl-5-oxo-4,5-dihydro-1H-1,2,4-triazol-1-yl]acetyl}-amino)[3-(trifluoromethyl)phenyl]acetyl}-beta-alaninate (racemate)

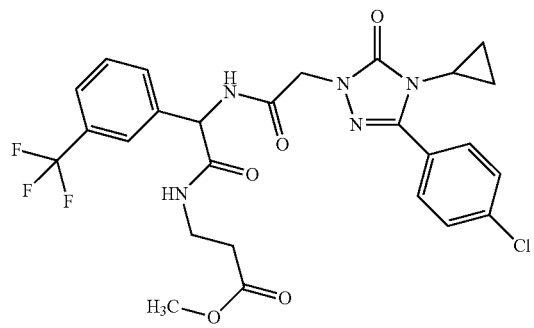 [SMILES: COC(=O)CCNC(=O)C(NC(=O)Cn1nc(-c2ccc(Cl)cc2)n(C2CC2)c1=O)c1cccc(C(F)(F)F)c1]

A mixture of 50 mg (0.14 mmol) of [3-(4-chlorophenyl)-4-cyclopropyl-5-oxo-4,5-dihydro-1H-1,2,4-triazol-1-yl]acetic acid (for the preparation, see WO 2007/134862, Example 88A), 49 mg (0.26 mmol) of EDC and 35 mg (0.26 mmol) of HOBt in 1.7 ml of DMF was stirred at RT for 20 min 64 mg (0.19 mmol) of the compound of Example 47A and 36 µl (0.20 mmol) of N,N'-diisopropylethylamine were added, and the mixture was stirred further overnight at RT and then separated by preparative HPLC [Method 6]. The appropriate fraction was concentrated on a rotary evaporator and the residue was dried under high vacuum. This gave 80 mg (81% of theory) of the title compound.

LC-MS [Method 3]: $R_t$=1.21 min; MS [ESIpos]: m/z=580 (M+H)$^+$ $^1$H-NMR (400 MHz, DMSO-$d_6$): δ [ppm]=0.50-0.60 (m, 2H), 0.84-0.94 (m, 2H), 2.41-2.47 (m, 2H), 3.17 (tt, 1H), 3.25-3.31 (m, 2H), 3.52 (s, 3H), 4.44-4.59 (m [AB], 2H), 5.55 (s, 1H), 7.53-7.63 (m, 3H), 7.63-7.72 (m, 2H), 7.72-7.83 (m, 3H), 8.59 (t, 1H), 9.01 (d, 1H).

Example 16

N-{({[3-(4-Chlorophenyl)-4-cyclopropyl-5-oxo-4,5-dihydro-1H-1,2,4-triazol-1-yl]acetyl}amino) [3-(trifluoromethyl)phenyl]acetyl}-beta-alanine (racemate)

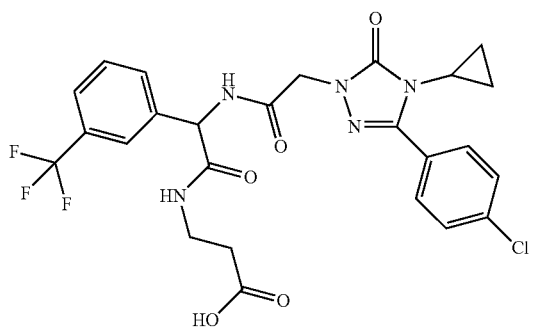 [SMILES: O=C(O)CCNC(=O)C(NC(=O)Cn1nc(-c2ccc(Cl)cc2)n(C2CC2)c1=O)c1cccc(C(F)(F)F)c1]

Analogously to Example 2, 52 mg (90 µmol) of the compound of Example 15 were hydrolysed and purified. This gave 33 mg (65% of theory) of the title compound.

LC-MS [Method 3]: $R_t$=1.13 min; MS [ESIpos]: m/z=566 (M+H)$^+$ $^1$H-NMR (400 MHz, DMSO-$d_6$): δ [ppm]=0.52-0.61 (m, 2H), 0.82-0.95 (m, 2H), 2.36 (t, 2H), 3.12-3.30 (m, 3H), 4.46-4.59 (m, 2H), 5.56 (d, 1H), 7.52-7.62 (m, 3H), 7.69 (t, 2H), 7.74-7.82 (m, 3H), 8.58 (t, 1H), 9.01 (d, 1H), 12.25 (br. s., 1H).

Example 17

N$^3$-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninamide (diastereomer 1)

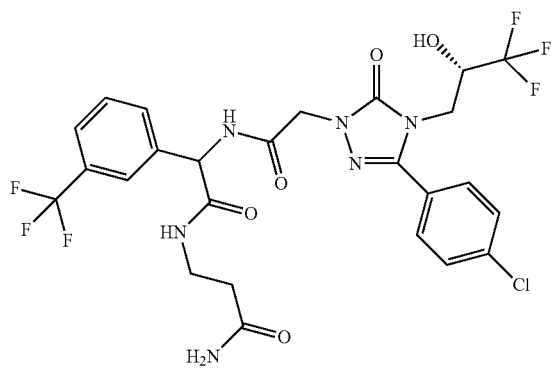 [SMILES: NC(=O)CCNC(=O)C(NC(=O)Cn1nc(-c2ccc(Cl)cc2)n(C[C@H](O)C(F)(F)F)c1=O)c1cccc(C(F)(F)F)c1]

A mixture of 19 mg (51 µmol) of the compound of Example 8A, 20 mg (61 µmol) of Example 48A, 15 mg (77 µmol) of EDC, 10 mg (77 µmol) of HOBt and 13 µl (77 µmol) of N,N'-diisopropylethylamine in 1 ml of DMF was stirred at RT for 20 min, 1 ml of 1N hydrochloric acid was then added and the mixture was separated by preparative HPLC [Method 6]. The appropriate fraction was concentrated on a rotary evaporator and the residue was dried under high vacuum. This gave 30 mg (92% of theory) of the title compound.

LC-MS [Method 1]: $R_t$=1.79 min; MS [ESIpos]: m/z=637 (M+H)$^+$ $^1$H-NMR (400 MHz, DMSO-$d_6$): δ [ppm]=2.15-2.25 (m, 2H), 3.16-3.30 (m, 2H), 3.82 (dd, 1H), 3.96 (dd, 1H), 4.18-4.34 (m, 1H), 4.59 (s, 2H), 5.58 (d, 1H), 6.82 (br. s., 1H), 6.90 (d, 1H), 7.29 (br. s., 1H), 7.55-7.68 (m, 4H), 7.69-7.77 (m, 3H), 7.78 (s, 1H), 8.55 (t, 1H), 9.04 (d, 1H).

Example 18

N$^3$-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-beta-alaninamide (diastereomer 2)

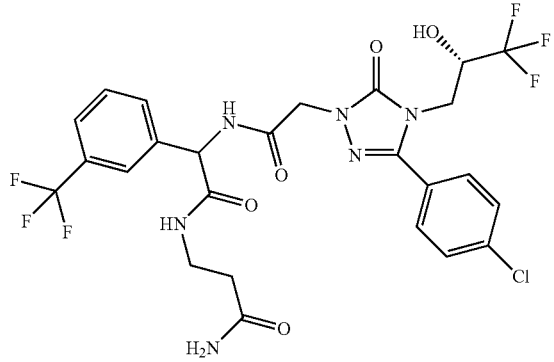 [SMILES: NC(=O)CCNC(=O)C(NC(=O)Cn1nc(-c2ccc(Cl)cc2)n(C[C@H](O)C(F)(F)F)c1=O)c1cccc(C(F)(F)F)c1]

Analogously to Example 17, 19 mg (51 µmol) of the compound of Example 8A and 25 mg (61 µmol) of the compound of Example 49A gave the title compound. Yield: 19 mg (58% of theory).

LC-MS [Method 1]: $R_t$=1.77 min; MS [ESIpos]: m/z=637 (M+H)$^+$ $^1$H-NMR (400 MHz, DMSO-$d_6$): δ [ppm]=2.13-2.26 (m, 2H), 3.16-3.32 (m, 2H), 3.82 (dd, 1H), 3.96 (dd, 1H), 4.19-4.33 (m, 1H), 4.53-4.65 (m [AB], 2H), 5.57 (d, 1H), 6.82 (br. s., 1H), 6.89 (d, 1H), 7.29 (br. s., 1H), 7.62 (d, 4H), 7.73 (s, 3H), 7.77-7.81 (m, 1H), 8.55 (t, 1H), 9.04 (d, 1H).

Example 19

N$^3$-{(2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-beta-alaninamide

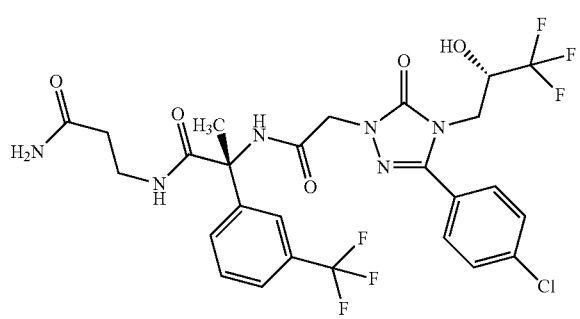 [SMILES: C[C@](NC(=O)Cn1nc(-c2ccc(Cl)cc2)n(C[C@H](O)C(F)(F)F)c1=O)(C(=O)NCCC(N)=O)c1cccc(C(F)(F)F)c1]

Analogously to Example 17, 40 mg (69 µmol) of the compound of Example 16A and 25 mg (103 µmol) of beta-alaninamide hydrochloride gave the title compound. Yield: 38 mg (85% of theory).

LC-MS [Method 1]: $R_t$=1.83 min; MS [ESIpos]: m/z=651 (M+H)$^+$ $^1$H-NMR (400 MHz, DMSO-$d_6$): δ [ppm]=1.84 (s, 3H), 2.09-2.22 (m, 2H), 3.13-3.28 (m, 2H), 3.82 (dd, 1H), 3.96 (dd, 1H), 4.19-4.36 (m, 1H), 4.58 (s, 2H), 6.76 (br. s., 1H), 6.90 (d, 1H), 7.25 (br. s., 1H), 7.51-7.58 (m, 1H), 7.60-7.66 (m, 3H), 7.69 (d, 1H), 7.75 (d, 3H), 7.90 (t, 1H), 8.69 (s, 1H).

Example 20

Methyl N-{(2R)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalaninate

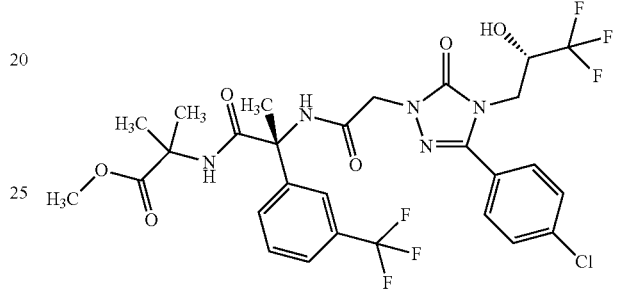

Analogously to Example 17, 40 mg (69 µmol) of the compound of Example 16A and 16 mg (103 µmol) of methyl 2-methylalaninate hydrochloride gave the title compound. Yield: 36 mg (77% of theory).

LC-MS [Method 1]: $R_t$=2.24 min; MS [ESIpos]: m/z=680 (M+H)$^+$ $^1$H-NMR (400 MHz, DMSO-$d_6$): δ [ppm]=1.26 (s, 3H), 1.29 (s, 3H), 1.82 (s, 3H), 3.52 (s, 3H), 3.82 (dd, 1H), 3.95 (dd, 1H), 4.17-4.32 (m, 1H), 4.52-4.63 (m [AB], 2H), 6.89 (d, 1H), 7.56-7.67 (m, 4H), 7.68-7.79 (m, 4H), 7.98 (s, 1H), 8.69 (s, 1H).

Example 21

N-{(2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propanoyl}-2-methylalanine

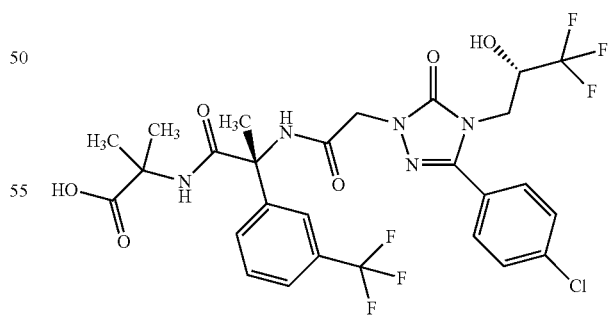 [SMILES: COC(=O)C(C)(C)NC(=O)[C@](C)(NC(=O)Cn1nc(-c2ccc(Cl)cc2)n(C[C@H](O)C(F)(F)F)c1=O)c1cccc(C(F)(F)F)c1]

32 mg (47 µmol) of the compound of Example 20 were dissolved in 1.6 ml of acetonitrile, and 235 µl (235 µmol) of a 1M aqueous lithium hydroxide solution were added. The mixture was stirred at RT overnight, 1 ml of 1N hydrochloric acid was then added and the mixture was separated by preparative HPLC [Method 6]. This gave 31 mg (99% of theory) of the title compound.

¹H-NMR (400 MHz, DMSO-d₆): δ [ppm]=1.27 (s, 3H), 1.29 (s, 3H), 1.80 (s, 3H), 3.82 (dd, 1H), 3.95 (dd, 1H), 4.19-4.33 (m, 1H), 4.51-4.64 (m [AB], 2H), 6.90 (d, 1H), 7.52-7.58 (m, 1H), 7.59-7.66 (m, 3H), 7.69-7.78 (m, 4H), 7.82 (s, 1H), 8.71 (s, 1H), 12.29 (s, 1H).

Example 22

N²-{(2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl}propanoyl]-2-methylalaninamide

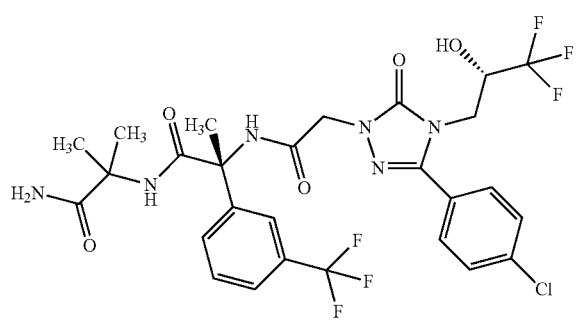 [SMILES: CC(C)(NC(=O)[C@](C)(NC(=O)Cn1nc(-c2ccc(Cl)cc2)n(C[C@H](O)C(F)(F)F)c1=O)c1cccc(C(F)(F)F)c1)C(N)=O]

A mixture of 31 mg (47 µmol) of the compound of Example 21, 13 mg (70 µmol) of EDC and 9.4 mg (70 µmol) of HOBt in 2 ml of DMF was stirred at RT for 20 min and then poured into 2 ml of ammonia (35% strength solution in water). The reaction mixture was stirred at RT for 30 min, then briefly concentrated on a rotary evaporator, acidified with 1N hydrochloric acid and separated by preparative HPLC [Method 6]. The appropriate fraction was concentrated on a rotary evaporator and the residue was dried under high vacuum. This gave 29 mg (92% of theory) of the title compound.

LC-MS [Method 3]: R$_t$=1.21 min; MS [ESIpos]: m/z=665 (M+H)⁺

¹H-NMR (400 MHz, DMSO-d₆): δ [ppm]=1.27 (s, 3H), 1.30 (s, 3H), 1.78 (s, 3H), 3.83 (dd, 1H), 3.96 (dd, 1H), 4.20-4.36 (m, 1H), 4.56-4.71 (m [AB], 2H), 6.85 (s, 2H), 6.89 (d, 1H), 7.55-7.69 (m, 4H), 7.73-7.84 (m, 5H), 8.91 (s, 1H).

Example 23

Methyl N-{[({3-(4-chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninate (diastereomer mixture)

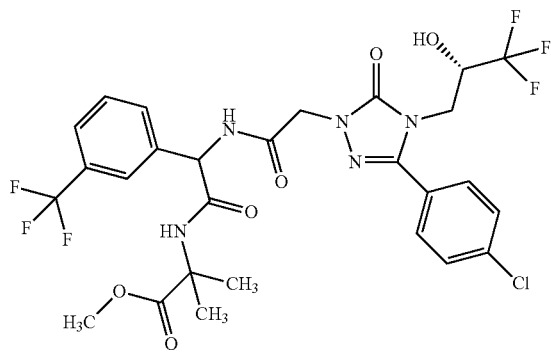 [SMILES: COC(=O)C(C)(C)NC(=O)C(NC(=O)Cn1nc(-c2ccc(Cl)cc2)n(C[C@H](O)C(F)(F)F)c1=O)c1cccc(C(F)(F)F)c1]

Analogously to Example 1, 398 mg (1.09 mmol) of the compound of Example 8A and 457 mg (1.20 mmol) of the compound of Example 46A were used to prepare the title compound. This gave 664 mg (91% of theory) of the title compound as a diastereomer mixture.

LC-MS [Method 3]: R$_t$=1.32 min; MS [ESIpos]: m/z=666 (M+H)⁺

¹H-NMR (400 MHz, DMSO-d₆): δ [ppm]=1.27 (s, 3H), 1.40 (s, 3H), 3.44 (d, interpreted as 3.440 and 3.444, 1 s each per diastereomer, 3H in total), 3.83 (dd, 1H), 3.96 (br. dd, 1H), 4.20-4.33 (m, 1H), 4.52-4.65 (m, 2H), 5.64 (d, 1H), 6.86-6.92 (dd, interpreted as 6.89 and 6.90, 1 d each per diastereomer, 1H), 7.58-7.80 (m, 7H), 8.84 (s, 1H), 9.02 (d, 1H).

Example 24

N-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer mixture)

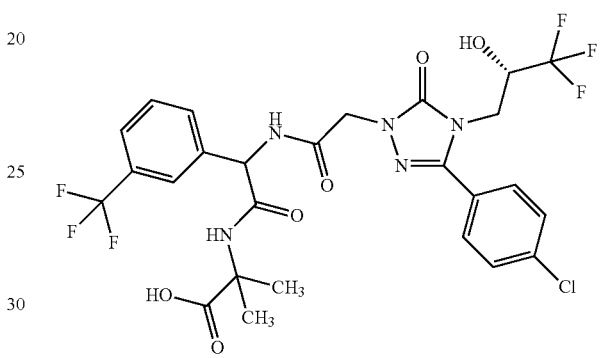

Analogously to Example 2, 69 mg (0.104 mmol) of the compound of Example 23 were hydrolysed and purified. This gave 63 mg (93% of theory) of the title compound as a diastereomer mixture.

LC-MS [Method 3]: R$_t$=1.22 min; MS [ESIpos]: m/z=652 (M+H)⁺

By preparative HPLC on a chiral phase [Method 14a], the two diastereomers were separated: see Example 25 and Example 26.

Example 25

N-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer 1)

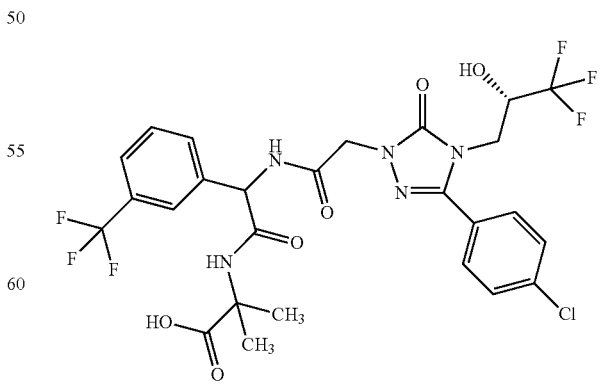

First-eluting diastereomer from the diastereomer separation of 63 mg of the compound of Example 24 according to Method 14a. After chromatography on the chiral phase, the product obtained was purified from solvent contaminants by preparative HPLC [Method 6]. This gave 15 mg of the title compound.

Chiral analytical HPLC [Method 15a]: $R_t$=5.02 min
LC-MS [Method 1]: $R_t$=1.99 min; MS [ESIpos]: m/z=652 (M+H)$^+$
$^1$H-NMR (400 MHz, DMSO-d$_6$): δ [ppm]=1.28 (s, 3H), 1.38 (s, 3H), 3.83 (dd, 1H), 3.96 (dd, 1H), 4.19-4.34 (m, 1H), 4.59 (s, 2H), 5.66 (d, 1H), 6.91 (d, 1H), 7.55-7.77 (m, 7H), 7.79 (s, 1H), 8.62-8.73 (m, 1H), 9.00 (d, 1H), 12.28 (s, 1H).

Example 26

N-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalanine (diastereomer 2)

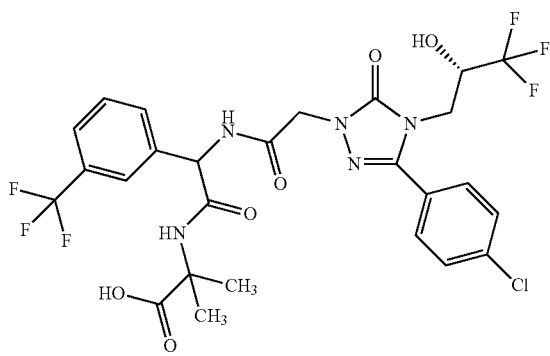 [SMILES: CC(C)(NC(=O)C(NC(=O)Cn1nc(-c2ccc(Cl)cc2)n(C[C@H](O)C(F)(F)F)c1=O)c1cccc(C(F)(F)F)c1)C(=O)O]

Last-eluting diastereomer from the diastereomer separation of 63 mg of the compound of Example 24 according to Method 14a. After chromatography on the chiral phase, the product obtained was purified from solvent contaminants by preparative HPLC [Method 6]. This gave 12 mg of the title compound.

Chiral analytical HPLC [Method 15a]: $R_t$=6.77 min
LC-MS [Method 1]: $R_t$=1.99 min; MS [ESIpos]: m/z=652 (M+H)$^+$
$^1$H-NMR (400 MHz, DMSO-d$_6$): δ [ppm]=1.27 (s, 3H), 1.38 (s, 3H), 3.83 (dd, 1H), 3.97 (dd, 1H), 4.18-4.34 (m, 1H), 4.53-4.65 (m [AB], 2H), 5.66 (d, 1H), 6.89 (d, 1H), 7.56-7.77 (m, 7H), 7.79 (s, 1H), 8.67 (s, 1H), 9.00 (d, 1H), 12.27 (s, 1H).

Example 27

N$^2$-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer mixture)

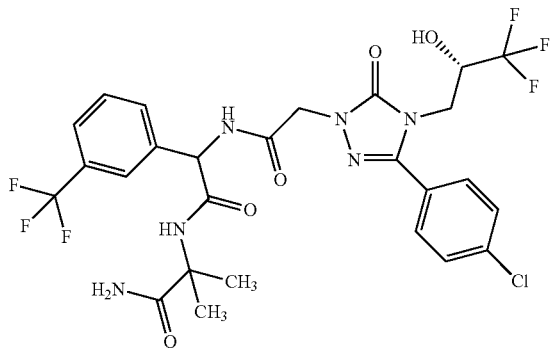 [SMILES: CC(C)(NC(=O)C(NC(=O)Cn1nc(-c2ccc(Cl)cc2)n(C[C@H](O)C(F)(F)F)c1=O)c1cccc(C(F)(F)F)c1)C(N)=O]

Analogously to Example 1, 195 mg (0.53 mmol) of the compound of Example 8A and 198 mg (0.58 mmol) of the compound of Example 63A gave the title compound as a diastereomer mixture: 330 mg (95% of theory).

LC-MS [Method 4]: $R_t$=2.22 min; MS [ESIpos]: m/z=651 (M+H)$^+$

By preparative HPLC on a chiral phase [Method 14b], the two diastereomers were separated: see Example 28 and Example 29.

Example 28

N$^2$-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer 1)

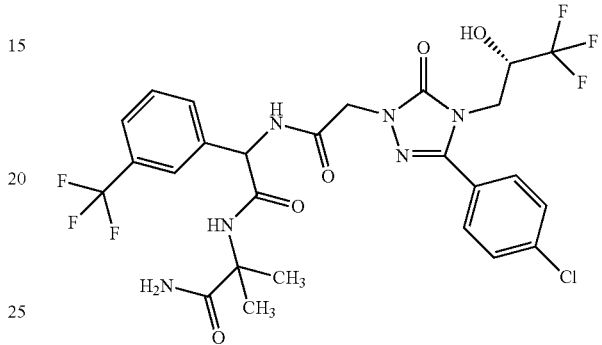

First-eluting diastereomer from the diastereomer separation of 320 mg of the compound of Example 27 according to Method 14b. After chromatography on the chiral phase, the product obtained was purified from solvent contaminants by preparative HPLC [Method 6]. This gave 130 mg of the title compound.

Chiral analytical HPLC [Method 15b]: $R_t$=3.52 min
LC-MS [Method 1]: $R_t$=1.90 min; MS [ESIpos]: m/z=651 (M+H)$^+$
$^1$H-NMR (400 MHz, DMSO-d$_6$): δ [ppm]=1.28 (s, 3H), 1.33 (s, 3H), 3.83 (dd, 1H), 3.96 (dd, 1H), 4.19-4.34 (m, 1H), 4.59 (s, 2H), 5.60 (d, 1H), 6.89 (br. s, 1H), 6.91 (d, 1H), 6.97 (br. s., 1H), 7.56-7.68 (m, 4H), 7.71-7.77 (m, 3H), 7.81 (s, 1H), 8.43 (s, 1H), 8.97 (d, 1H).

Example 29

N$^2$-{[({3-(4-Chlorophenyl)-5-oxo-4-[(2S)-3,3,3-trifluoro-2-hydroxypropyl]-4,5-dihydro-1H-1,2,4-triazol-1-yl}acetyl)amino][3-(trifluoromethyl)phenyl]acetyl}-2-methylalaninamide (diastereomer 2)

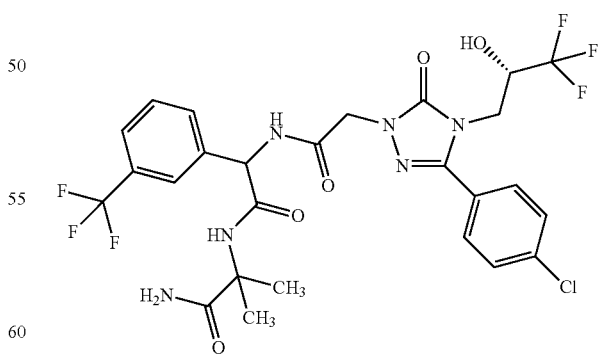

Last-eluting diastereomer from the diastereomer separation of 320 mg of the compound of Example 27 according to Method 14b. After chromatography on the chiral phase, the product obtained was purified from solvent contaminants by preparative HPLC [Method 6]. This gave 141 mg of the title compound.

Chiral analytical HPLC [Method 15b]: R$_t$=5.01 min
LC-MS [Method 1]: R$_t$=1.89 min; MS [ESIpos]: m/z=651 (M+H)$^+$
$^1$H-NMR (400 MHz, DMSO-d$_6$): δ [ppm]=1.27 (s, 3H), 1.33 (s, 3H), 3.83 (dd, 1H), 3.97 (dd, 1H), 4.19-4.33 (m, 1H), 4.52-4.65 (m [AB], 2H), 5.61 (s, 1H), 6.89 (br. s, 2H), 6.97 (s, 1H), 7.55-7.77 (m, 7H), 7.81 (s, 1H), 8.44 (s, 1H), 8.96 (d, 1H).

Example 30

N$^2$-{({[3-(4-Chlorophenyl)-4-(2-fluorobenzyl)-5-oxo-4,5-dihydro-1H-1,2,4-triazol-1-yl]acetyl}-amino) [2-(trifluoromethyl)phenyl]acetyl}-2-methylalaninamide (racemate)

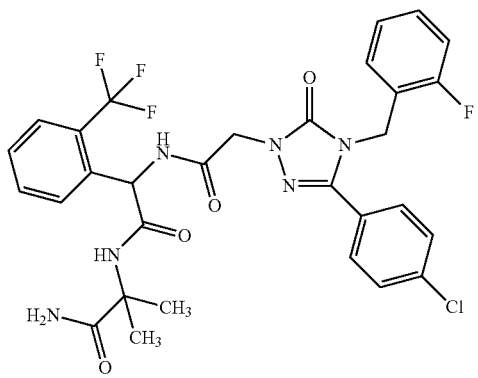 [SMILES: CC(C)(NC(=O)C(NC(=O)Cn1nc(-c2ccc(Cl)cc2)n(Cc2ccccc2F)c1=O)c1ccccc1C(F)(F)F)C(N)=O]

Analogously to Example 1, 25 mg (69 μmol) of [3-(4-chlorophenyl)-4-(2-fluorobenzyl)-5-oxo-4,5-dihydro-1H-1,2,4-triazol-1-yl]acetic acid (for the preparation, see WO 2007/134862, Example 156A) and 28 mg (76 mol) of the compound of Example 62A were employed. Purification by HPLC [Method 7] gave 28 mg (63% of theory) of the title compound.

LC-MS [Method 5]: R$_t$=1.01 min; MS [ESIpos]: m/z=647 (M+H)$^+$
$^1$H-NMR (400 MHz, DMSO-d$_6$): δ [ppm]=1.35 (s, 3H), 1.37 (s, 3H), 4.51-4.68 (m [AB], 2H), 5.02 (s, 2H), 5.65 (d, 1H), 7.00-7.18 (m, 5H), 7.26-7.34 (m, 1H), 7.49-7.59 (m, 5H), 7.66-7.77 (m, 3H), 8.03 (s, 1H), 9.15 (d, 1H).

Example 31

N$^2$-{[({3-(4-Chlorophenyl)-5-oxo-4-[(1E)-3,3,3-trifluoroprop-1-en-1-yl]-4,5-dihydro-1H-1,2,4-triazol-1-yl}acetyl)amino][2-(trifluoromethyl)phenyl]acetyl}-2-methylalaninamide (racemate)

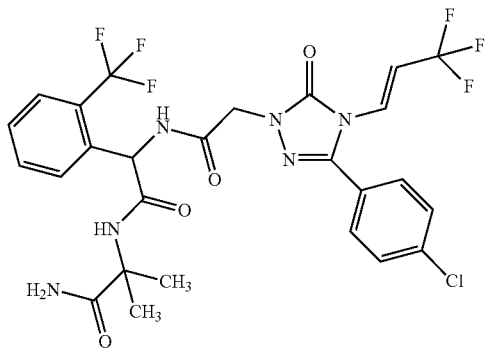 [SMILES: CC(C)(NC(=O)C(NC(=O)Cn1nc(-c2ccc(Cl)cc2)n(/C=C/C(F)(F)F)c1=O)c1ccccc1C(F)(F)F)C(N)=O]

Analogously to Example 1, 25 mg (72 μmol) of the compound of Example 11A and 29 mg (79 μmol) of the compound of Example 62A were employed. Purification by HPLC [Method 7] gave 32 mg (70% of theory) of the title compound.

LC-MS [Method 5]: R$_t$=1.04 min; MS [ESIpos]: m/z=633 (M+H)$^+$
$^1$H-NMR (400 MHz, DMSO-d$_6$): δ [ppm]=1.36 (s, 3H), 1.38 (s, 3H), 4.52-4.68 (m [AB], 2H), 5.65 (d, 1H), 6.85 (dq, 1H), 7.03 (br. s, 1H), 7.06 (br. s, 1H), 7.17 (dq, 1H), 7.55 (t, 1H), 7.61-7.78 (m, 7H), 8.02 (s, 1H), 9.16 (d, 1H).

Example 32

N$^2$-{({[3-(4-Chlorophenyl)-5-oxo-4-(3,3,3-trifluoropropyl)-4,5-dihydro-1H-1,2,4-triazol-1-yl] acetyl}amino) [2-(trifluoromethyl)phenyl]acetyl}-2-methylalaninamide (racemate)

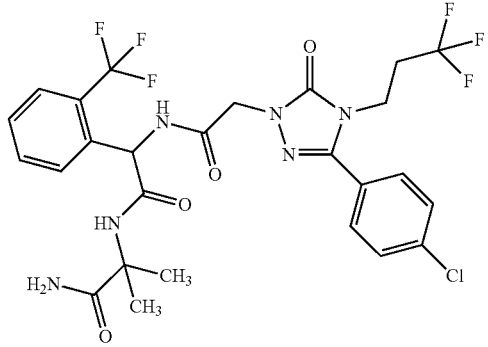 [SMILES: CC(C)(NC(=O)C(NC(=O)Cn1nc(-c2ccc(Cl)cc2)n(CCC(F)(F)F)c1=O)c1ccccc1C(F)(F)F)C(N)=O]

A solution of 25 mg (39 μmol) of the compound of Example 31 in 10 ml of methanol was hydrogenated in an H-Cube fitted with a platinum cartridge (5% Pt/C) (continuous-flow hydrogenation apparatus from Thales Nano, Budapest, Model HC-2-SS) at a flow rate of 1 ml/min, at 60° C. and under hydrogen at standard pressure. The resulting solution was freed from methanol on a rotary evaporator, and the residue was dissolved in 2 ml of acetonitrile and purified by preparative HPLC [Method 7]. This gave 8 mg (32% of theory) of the title compound.

LC/MS [Method 5]: R$_t$=0.96 min; m/z=635 (M+H)$^+$
$^1$H-NMR (400 MHz, DMSO-d$_6$): δ [ppm]=1.35 (s, 3H), 1.38 (s, 3H), 2.56-2.66 (m, 2H), 3.98 (t, 2H), 4.46-4.62 (m [AB], 2H), 5.63 (d, 1H), 7.03 (br.s, 1H), 7.04 (br.s, 1H), 7.51-7.58 (m, 1H), 7.60-7.77 (m, 7H), 8.01 (s, 1H), 9.11 (d, 1H).

Example 33

N$^2$-[(2-Chlorophenyl)({[3-(4-chlorophenyl)-4-(2-fluorobenzyl)-5-oxo-4,5-dihydro-1H-1,2,4-triazol-1-yl]acetyl}amino)acetyl]-2-methylalaninamide (racemate)

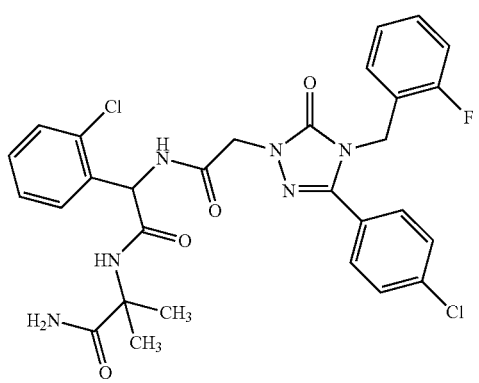 [SMILES: CC(C)(NC(=O)C(NC(=O)Cn1nc(-c2ccc(Cl)cc2)n(Cc2ccccc2F)c1=O)c1ccccc1Cl)C(N)=O]

Analogously to Example 1, 25 mg (69 μmol) of [3-(4-chlorophenyl)-4-(2-fluorobenzyl)-5-oxo-4,5-dihydro-1H-1, 2,4-triazol-1-yl]acetic acid (for the preparation, see WO 2007/134862, Example 156A) and 26 mg (76 µmol) of the compound of Example 64A were employed. Purification by HPLC [Method 7] gave 35 mg (83% of theory) of the title compound.

LC-MS [Method 5]: $R_t$=0.97 min; MS [ESIpos]: m/z=613 (M+H)$^+$ $^1$H-NMR (400 MHz, DMSO-$d_6$): δ [ppm]=1.35 (s, 3H), 1.38 (s, 3H), 4.53-4.66 (m [AB], 2H), 5.03 (s, 2H), 5.70 (d, 1H), 6.97 (br. s., 1H), 7.01 (br. s., 1H), 7.02-7.18 (m, 3H), 7.26-7.39 (m, 3H), 7.44-7.51 (m, 2H), 7.53 (s, 4H), 8.12 (s, 1H), 9.01 (d, 1H).

Example 34

N$^2$-{(2-Chlorophenyl) [({3-(4-chlorophenyl)-5-oxo-4-[(1E)-3,3,3-trifluoroprop-1-en-1-yl]-4,5-dihydro-1H-1,2,4-triazol-1-yl}acetyl)amino]acetyl}-2-methylalaninamide (racemate)

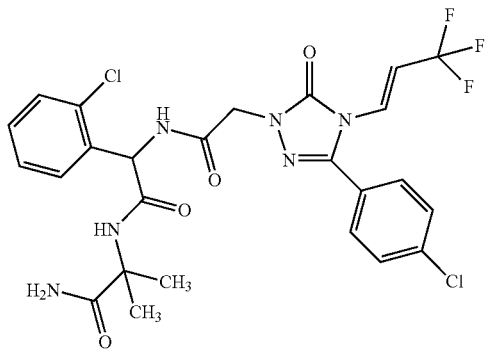 [SMILES: CC(C)(NC(=O)C(NC(=O)Cn1nc(-c2ccc(Cl)cc2)n(/C=C/C(F)(F)F)c1=O)c1ccccc1Cl)C(N)=O]

Analogously to Example 1, 25 mg (72 µmol) of the compound of Example 11A and 27 mg (79 µmol) of the compound of Example 64A were employed. Purification by HPLC [Method 7] gave 34 mg (79% of theory) of the title compound.

LC-MS [Method 5]: $R_t$=1.01 min; MS [ESIpos]: m/z=599 (M+H)$^+$ $^1$H-NMR (400 MHz, DMSO-$d_6$): δ [ppm]=1.35 (s, 3H), 1.39 (s, 3H), 4.54-4.66 (m [AB], 2H), 5.69 (d, 1H), 6.85 (dq, 1H), 6.96 (br. s., 1H), 7.02 (br. s., 1H), 7.17 (dq, 1H), 7.32-7.39 (m, 2H), 7.44-7.51 (m, 2H), 7.61-7.70 (m, 4H), 8.12 (s, 1H), 9.02 (d, 1H).

Example 35

N$^2$-[(2-Chlorophenyl)({[3-(4-chlorophenyl)-5-oxo-4-(3,3,3-trifluoropropyl)-4,5-dihydro-1H-1,2,4-triazol-1-yl]acetyl}amino)acetyl]-2-methylalaninamide (racemate)

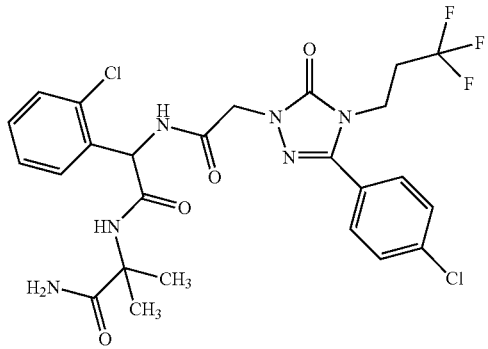 [SMILES: CC(C)(NC(=O)C(NC(=O)Cn1nc(-c2ccc(Cl)cc2)n(CCC(F)(F)F)c1=O)c1ccccc1Cl)C(N)=O]

Analogously to Example 32, 20 mg (33 µmol) of the compound of Example 34 were hydrogenated and purified. This gave 11 mg (54% of theory) of the title compound.

LC-MS [Method 5]: $R_t$=0.98 min; MS [ESIpos]: m/z=601 (M+H)$^+$ $^1$H-NMR (400 MHz, DMSO-$d_6$): δ [ppm]=1.35 (s, 3H), 1.38 (s, 3H), 2.59-2.66 (m, 2H), 3.98 (t, 2H), 4.48-4.62 (m [AB], 2H), 5.68 (d, 1H), 6.96 (br. s, 1H), 7.01 (br. s, 1H), 7.31-7.40 (m, 2H), 7.42-7.52 (m, 2H), 7.65 (q, 4H), 8.10 (s, 1H), 8.97 (d, 1H).

Example 36

N$^2$-[({[3-(4-Chlorophenyl)-4-(2-fluorobenzyl)-5-oxo-4,5-dihydro-1H-1,2,4-triazol-1-yl]acetyl}-amino)(2,3-dichlorophenyl)acetyl]-2-methylalaninamide (racemate)

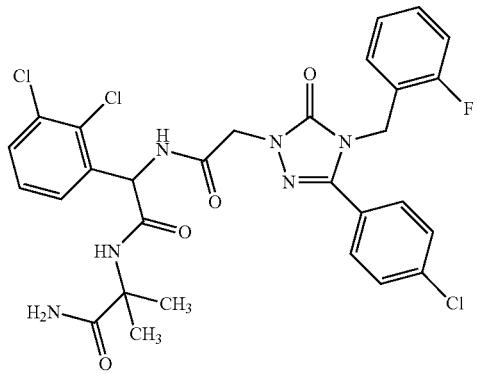 [SMILES: CC(C)(NC(=O)C(NC(=O)Cn1nc(-c2ccc(Cl)cc2)n(Cc2ccccc2F)c1=O)c1cccc(Cl)c1Cl)C(N)=O]

Analogously to Example 1, 25 mg (69 µmol) of [3-(4-chlorophenyl)-4-(2-fluorobenzyl)-5-oxo-4,5-dihydro-1H-1,2,4-triazol-1-yl]acetic acid (for the preparation, see WO 2007/134862, Example 156A) and 28 mg (76 µmol) of the compound of Example 65A were reacted. Purification by HPLC [Method 7] gave 35 mg (78% of theory) of the title compound.

LC-MS [Method 5]: $R_t$=1.03 min; MS [ESIpos]: m/z=647 (M+H)$^+$ $^1$H-NMR (400 MHz, DMSO-$d_6$): δ [ppm]=1.36 (s, 3H), 1.37 (s, 3H), 4.54-4.68 (m [AB], 2H), 5.02 (s, 2H), 5.75 (d, 1H), 6.97 (br. s., 1H), 6.99 (br. s., 1H), 7.01-7.07 (m, 1H), 7.07-7.19 (m, 2H), 7.26-7.34 (m, 1H), 7.39 (t, 1H), 7.46 (dd, 1H), 7.53 (s, 4H), 7.62 (dd, 1H), 8.21 (s, 1H), 9.08 (d, 1H).

Example 37

N$^2$-{[({3-(4-Chlorophenyl)-5-oxo-4-[(1E)-3,3,3-trifluoroprop-1-en-1-yl]-4,5-dihydro-1H-1,2,4-triazol-1-yl}acetyl)amino](2,3-dichlorophenyl)acetyl}-2-methylalaninamide (racemate)

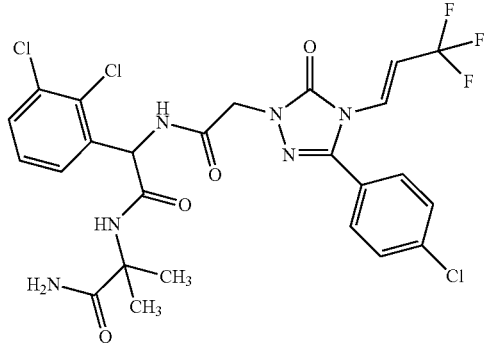 [SMILES: CC(C)(NC(=O)C(NC(=O)Cn1nc(-c2ccc(Cl)cc2)n(/C=C/C(F)(F)F)c1=O)c1cccc(Cl)c1Cl)C(N)=O]

Analogously to Example 1, 25 mg (72 µmol) of the compound of Example 11A and 29 mg (79 µmol) of the compound of Example 65A were reacted. Purification by HPLC [Method 7] gave 35 mg (77% of theory) of the title compound.

LC-MS [Method 5]: $R_t$=1.06 min; MS [ESIpos]: m/z=633 (M+H)$^+$ $^1$H-NMR (400 MHz, DMSO-d$_6$): δ [ppm]=1.35 (s, 3H), 1.38 (s, 3H), 4.55-4.66 (m [AB], 2H), 5.74 (d, 1H), 6.85 (dq, 1H), 6.96 (br. s., 1H), 7.00 (br. s., 1H), 7.14-7.21 (m, 1H), 7.39 (t, 1H), 7.45 (dd, 1H), 7.60-7.70 (m, 5H), 8.22 (s, 1H), 9.09 (d, 1H).

Example 38

Methyl N-{(3S)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninate

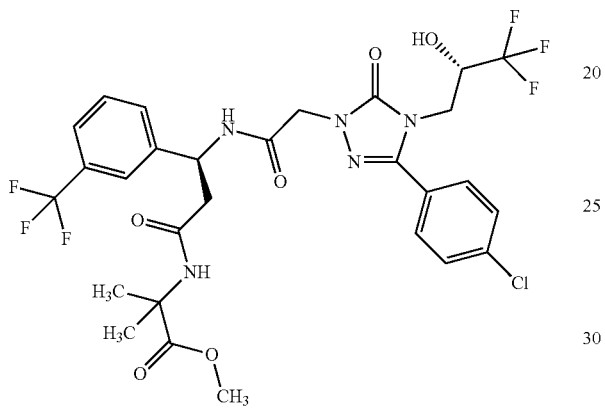

Analogously to Example 1, 93 mg (0.26 mmol) of the compound of Example 8A and 108 mg (0.29 mmol) of the compound of Example 67A gave the title compound. Yield: 134 mg (77% of theory).

LC-MS [Method 3]: $R_t$=1.32 min; MS [ESIpos]: m/z=680 (M+H)$^+$ $^1$H-NMR (400 MHz, DMSO-d$_6$): δ [ppm]=1.18 (s, 3H), 1.23 (s, 3H), 2.56-2.67 (m, 2H), 3.44 (s, 3H), 3.82 (dd, 1H), 3.96 (dd, 1H), 4.21-4.34 (m, 1H), 4.48 (s, 2H), 5.26 (q, 1H), 6.89 (d, 1H), 7.53-7.66 (m, 6H), 7.75 (d, 2H), 8.29 (s, 1H), 8.81 (d, 1H).

Example 39

N-{(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalanine

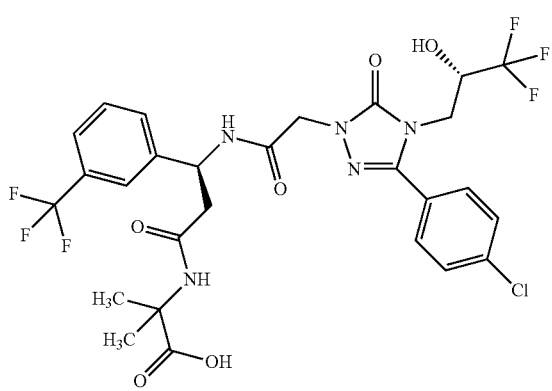 [SMILES: CC(C)(NC(=O)C[C@H](NC(=O)Cn1nc(-c2ccc(Cl)cc2)n(C[C@H](O)C(F)(F)F)c1=O)c1cccc(C(F)(F)F)c1)C(=O)O]

478 µl (478 µmol) of a 1N aqueous solution of lithium hydroxide were added to a solution of 130 mg (0.19 mmol) of the compound of Example 38 in 5 ml of acetonitrile, and the mixture was stirred at RT overnight. After addition of 1 ml of 1N hydrochloric acid, the entire mixture was separated by preparative HPLC [Method 6]. This gave 103 mg (81% of theory) of the title compound.

LC-MS [Method 1]: $R_t$=1.97 min; MS [ESIpos]: m/z=666 (M+H)$^+$ $^1$H-NMR (400 MHz, DMSO-d$_6$): δ [ppm]=1.18 (s, 3H), 1.22 (s, 3H), 2.53-2.66 (m, 2H), 3.82 (dd, 1H), 3.92-4.01 (m, 1H), 4.20-4.33 (m, 1H), 4.48 (s, 2H), 5.27 (q, 1H), 6.90 (d, 1H), 7.50-7.57 (m, 1H), 7.57-7.65 (m, 5H), 7.75 (d, 2H), 8.10 (s, 1H), 8.81 (d, 1H), 12.15 (s, 1H).

Example 40

N$^2$-{(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propanoyl}-2-methylalaninamide

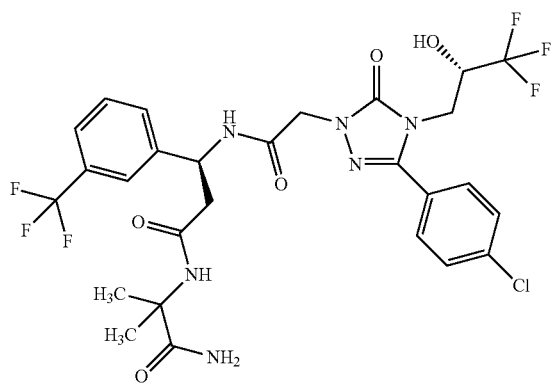

A mixture of 50 mg (75 µmol) of the compound of Example 39, 29 mg (0.15 mmol) of EDC and 20 mg (0.15 mmol) of HOBt in 2 ml of DMF was stirred at RT for 20 min and then poured into 5 ml of ammonia (35% strength solution in water). The reaction mixture was stirred at RT for 30 min and then concentrated on a rotary evaporator, acidified with 2.5 N hydrochloric acid and separated by preparative HPLC [Method 6]. The appropriate fraction was concentrated on a rotary evaporator and the residue was dried under high vacuum. This gave 42 mg (84% of theory) of the title compound.

LC-MS [Method 1]: $R_t$=1.85 min; MS [ESIpos]: m/z=665 (M+H)$^+$ $^1$H-NMR (400 MHz, DMSO-d$_6$): δ [ppm]=1.21 (s, 3H), 1.22 (s, 3H), 2.56-2.68 (m, 2H), 3.82 (dd, 1H), 3.96 (dd, 1H), 4.19-4.33 (m, 1H), 4.42-4.54 (m [AB], 2H), 5.23-5.32 (m, 1H), 6.79 (br. s., 1H), 6.86-6.96 (m, 1H), 7.52-7.58 (m, 1H), 7.58-7.66 (m, 6H), 7.75 (d, 2H), 7.90 (s, 1H), 8.82 (d, 1H).

Example 41

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(1-hydroxy-2-methylpropan-2-yl)-2-[3-(trifluoromethyl)phenyl]-acetamide (diastereomer 1)

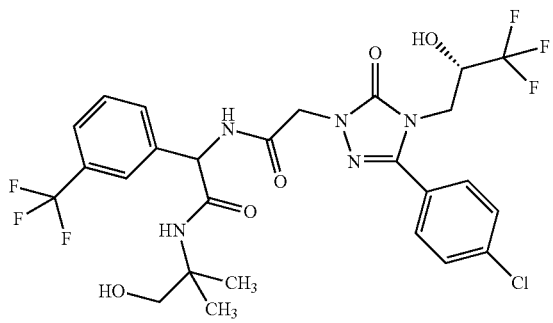 [SMILES: CC(C)(CO)NC(=O)C(NC(=O)Cn1nc(-c2ccc(Cl)cc2)n(C[C@H](O)C(F)(F)F)c1=O)c1cccc(C(F)(F)F)c1]

A mixture of 50 mg (0.14 mmol) of the compound of Example 8A, 67 mg (0.21 mmol) of the compound of Example 50A, 39 mg (0.21 mmol) of EDC, 28 mg (0.21 mmol) of HOBt and 48 μl (0.27 mmol) of N,N'-diisopropylethylamine in 1.3 ml of DMF was stirred at RT overnight, 1 ml of 1N hydrochloric acid was then added and the mixture was separated by preparative HPLC [Method 6]. The appropriate fraction was concentrated on a rotary evaporator and the residue was dried under high vacuum. This gave 61 mg (70% of theory) of the title compound.

LC-MS [Method 4]: $R_t$=2.38 min; MS [ESIpos]: m/z=638 (M+H)$^+$ $^1$H-NMR (400 MHz, DMSO-d$_6$): δ [ppm]=1.14 (s, 3H), 1.15 (s, 3H), 3.28-3.34 (m, 1H), 3.39-3.46 (m, 1H), 3.83 (dd, 1H), 3.97 (dd, 1H), 4.19-4.33 (m, 1H), 4.54-4.66 (m [AB], 2H), 4.78 (t, 1H), 5.63 (d, 1H), 6.89 (d, 1H), 7.56-7.68 (m, 4H), 7.69-7.76 (m, 3H), 7.79 (s, 1H), 7.99 (s, 1H), 8.93 (d, 1H).

Example 42

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(1-hydroxy-2-methylpropan-2-yl)-2-[3-(trifluoromethyl)phenyl]-acetamide (diastereomer 2)

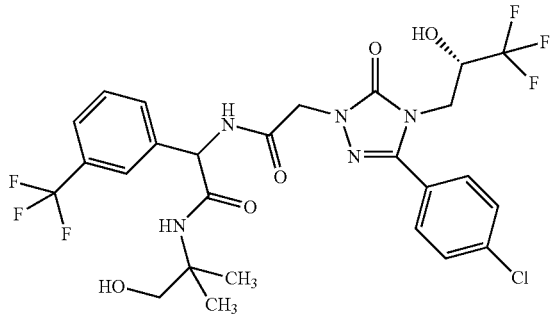 [SMILES: CC(C)(CO)NC(=O)C(NC(=O)Cn1nc(-c2ccc(Cl)cc2)n(C[C@H](O)C(F)(F)F)c1=O)c1cccc(C(F)(F)F)c1]

Analogously to Example 41, 50 mg (0.14 mmol) of the compound of Example 8A and 67 mg (0.21 mmol) of the compound of Example 51A were used to prepare the title compound. This gave 65 mg (75% of theory).

LC-MS [Method 3]: $R_t$=1.27 min; MS [ESIpos]: m/z=638 (M+H)$^+$ $^1$H-NMR (400 MHz, DMSO-d$_6$): δ [ppm]=1.14 (s, 3H), 1.15 (s, 3H), 3.29-3.34 (m, 1H), 3.40-3.46 (m, 1H), 3.83 (dd, 1H), 3.96 (dd, 1H), 4.19-4.33 (m, 1H), 4.60 (s, 2H), 4.78 (t, 1H), 5.64 (d, 1H), 6.90 (d, 1H), 7.55-7.67 (m, 4H), 7.69-7.77 (m, 3H), 7.78 (br. s, 1H), 7.98 (s, 1H), 8.93 (d, 1H).

Example 43

2-({[3-(5-Chloro-2-thienyl)-4-(2-methoxyethyl)-5-oxo-4,5-dihydro-1H-1,2,4-triazol-1-yl]acetyl}amino)-N-(1-hydroxy-2-methylpropan-2-yl)-2-[3-(trifluoromethyl)phenyl]acetamide (enantiomer 1)

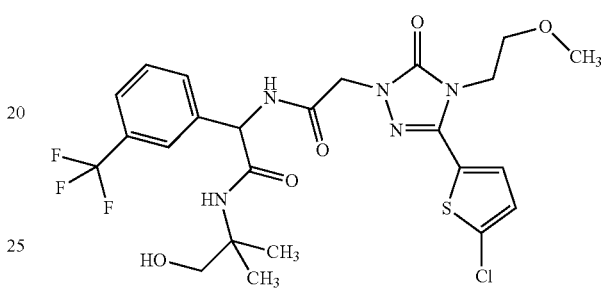

Analogously to Example 1, 25 mg (79 μmol) of the compound of Example 15A and 28 mg (87 μmol) of the compound of Example 50A were employed. Purification by HPLC [Method 7] gave 30 mg (65% of theory) of the title compound.

LC-MS [Method 5]: $R_t$=0.99 min; MS [ESIpos]: m/z=590 (M+H)$^+$ $^1$H-NMR (400 MHz, DMSO-d$_6$): δ [ppm]=1.14 (s, 3H), 1.15 (s, 3H), 3.19 (s, 3H), 3.28-about 3.33 (m, 1H), 3.39-3.47 (m, 1H), 3.54 (t, 2H), 3.97 (t, 2H), 4.56 (s, 2H), 4.78 (t, 1H), 5.63 (d, 1H), 7.26 (d, 1H), 7.56 (d, 1H), 7.57-7.62 (m, 1H), 7.63-7.68 (m, 1H), 7.71 (d, 1H), 7.78 (s, 1H), 7.99 (s, 1H), 8.93 (d, 1H).

Example 44

2-({[3-(5-Chloro-2-thienyl)-4-(2-methoxyethyl)-5-oxo-4,5-dihydro-1H-1,2,4-triazol-1-yl]acetyl}-amino)-N-(1-hydroxy-2-methylpropan-2-yl)-2-[3-(trifluoromethyl)phenyl]acetamide (enantiomer 2)

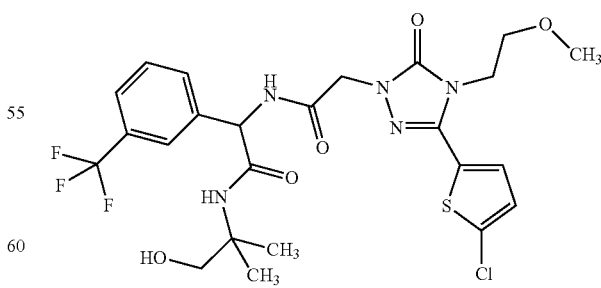

Analogously to Example 1, 25 mg (79 μmol) of the compound of Example 15A and 28 mg (87 μmol) of the compound of Example 51A were employed. Purification by HPLC [Method 7] gave 33 mg (71% of theory) of the title compound.

LC-MS [Method 5]: $R_t$=0.99 min; MS [ESIpos]: m/z=590 (M+H)$^+$

Example 45

2-(2-Chlorophenyl)-2-({[3-(4-chlorophenyl)-4-(2-fluorobenzyl)-5-oxo-4,5-dihydro-1H-1,2,4-triazol-1-yl]acetyl}amino)-N-(2-methoxyethyl)acetamide (racemate)

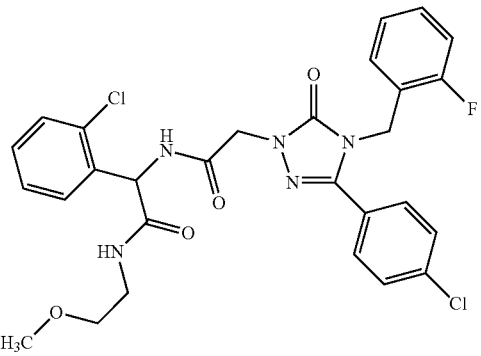 [SMILES: COCCNC(=O)C(NC(=O)Cn1nc(-c2ccc(Cl)cc2)n(Cc2ccccc2F)c1=O)c1ccccc1Cl]

Analogously to Example 1, 25 mg (69 µmol) of [3-(4-chlorophenyl)-4-(2-fluorobenzyl)-5-oxo-4,5-dihydro-1H-1,2,4-triazol-1-yl]acetic acid (for the preparation, see WO 2007/134862, Example 156A) and 21 mg (76 µmol) of the compound of Example 66A were employed. Purification by HPLC [Method 7] gave 35 mg (86% of theory) of the title compound.

LC-MS [Method 5]: $R_t$=1.03 min; MS [ESIpos]: m/z=586 (M+H)$^+$ $^1$H-NMR (400 MHz, DMSO-d$_6$): δ [ppm]=3.22 (s, 3H), 3.22-3.28 (m, 2H), 3.34-3.38 (m, 2H), 4.51-4.67 (m [AB], 2H), 5.03 (s, 2H), 5.72 (d, 1H), 7.04 (dt, 1H), 7.08-7.19 (m, 2H), 7.26-7.39 (m, 3H), 7.41-7.49 (m, 2H), 7.53 (s, 4H), 8.34 (t, 1H), 8.93 (d, 1H).

Example 46

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[2-(trifluoromethyl)phenyl]acetamide (diastereomer mixture)

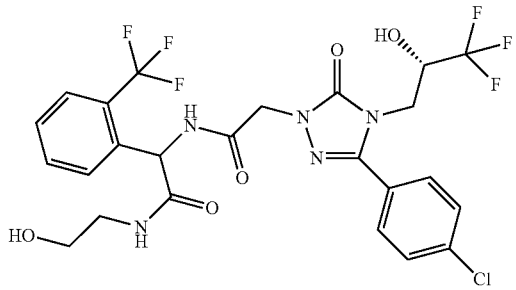 [SMILES: O=C(Cn1nc(-c2ccc(Cl)cc2)n(C[C@H](O)C(F)(F)F)c1=O)NC(C(=O)NCCO)c1ccccc1C(F)(F)F]

47 mg (0.25 mmol) of EDC were added to a mixture of 50 mg (0.14 mmol) of the compound of Example 8A and 33 mg (0.25 mmol) of HOBt in 2.9 ml of DMF, and the mixture was stirred at RT for 20 min 49 mg (0.16 mmol) of the compound of Example 52A and 57 µl (0.33 mmol) of N,N'-diisopropylethylamine were added, and the mixture was stirred overnight. After addition of 1 ml of 1N hydrochloric acid, the reaction mixture was separated by preparative HPLC [Method 6]. The appropriate fraction was concentrated on a rotary evaporator and the residue was dried under high vacuum. This gave 24 mg (28% of theory) of the title compound as a diastereomer mixture.

LC-MS [Method 3]: $R_t$=1.11 min; MS [ESIpos]: m/z=610 (M+H)$^+$

By preparative chromatography on a chiral phase (Method 10), the two diastereomers were separated: see Example 47 and Example 48.

Example 47

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[2-(trifluoromethyl)phenyl]acetamide (diastereomer 1)

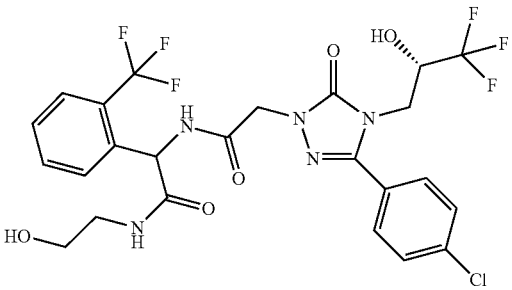 [SMILES: O=C(Cn1nc(-c2ccc(Cl)cc2)n(C[C@H](O)C(F)(F)F)c1=O)NC(C(=O)NCCO)c1ccccc1C(F)(F)F]

First-eluting diastereomer (11 mg) from the chromatographic diastereomer separation according to Method 10 of 24 mg of the compound of Example 46.

Chiral analytical HPLC [Method 11]: $R_t$=1.87 min

LC-MS [Method 1]: $R_t$=1.78 min; MS [ESIpos]: m/z=610 (M+H)$^+$ $^1$H-NMR (400 MHz, DMSO-d$_6$): δ [ppm]=3.08-3.24 (m, 2H), 3.36-3.45 (m, 2H), 3.82 (dd, 1H), 3.96 (dd, 1H), 4.19-4.35 (m, 1H), 4.48 (d, 1H), 4.62 (d, 1H), 4.67 (t, 1H), 5.69 (d, 1H), 6.92 (d, 1H), 7.50-7.58 (m, 1H), 7.60-7.66 (m, 3H), 7.67-7.78 (m, 4H), 8.17 (t, 1H), 9.03 (d, 1H).

Example 48

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[2-(trifluoromethyl)phenyl]acetamide (diastereomer 2)

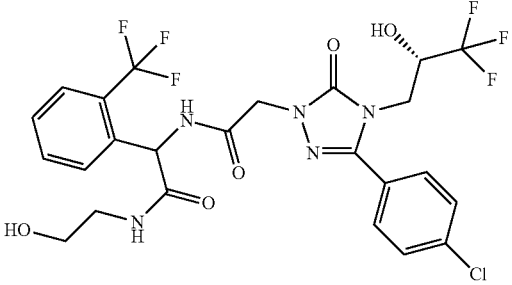 [SMILES: O=C(Cn1nc(-c2ccc(Cl)cc2)n(C[C@H](O)C(F)(F)F)c1=O)NC(C(=O)NCCO)c1ccccc1C(F)(F)F]

Last-eluting diastereomer (10 mg) from the chromatographic diastereomer separation according to Method 10 of 24 mg of the compound of Example 46.

Chiral analytical HPLC [Method 11]: $R_t$=4.12 min

LC-MS [Method 1]: $R_t$=1.76 min; MS [ESIpos]: m/z=610 (M+H)$^+$ $^1$H-NMR (400 MHz, DMSO-d$_6$): δ [ppm]=3.07-3.24 (m, 2H), 3.36-3.46 (m, 2H), 3.82 (dd, 1H), 3.96 (dd, 1H), 4.20-4.34 (m, 1H), 4.47 (d, 1H), 4.59-4.69 (m, 2H), 5.69 (d, 1H), 6.90 (d, 1H), 7.54 (t, 1H), 7.60-7.66 (m, 3H), 7.67-7.77 (m, 4H), 8.17 (t, 1H), 9.04 (d, 1H).

Example 49

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer mixture)

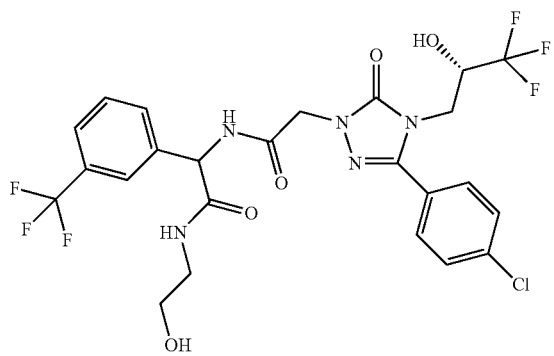 [SMILES: O=C(Cn1nc(-c2ccc(Cl)cc2)n(C[C@H](O)C(F)(F)F)c1=O)NC(C(=O)NCCO)c1cccc(C(F)(F)F)c1]

Analogously to Example 46, 30 mg (82 μmol) of the compound of Example 8A and 29 mg (98 μmol) of the compound of Example 54A were used to prepare the title compound. This gave 37 mg (74% of theory) as diastereomer mixture.

LC-MS [Method 3]: $R_t$=1.17 min; MS [ESIpos]: m/z=610 (M+H)$^+$

By preparative chromatography on a chiral phase (Method 10), the two diastereomers were separated: see Examples 50 and 51.

Example 50

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer 1)

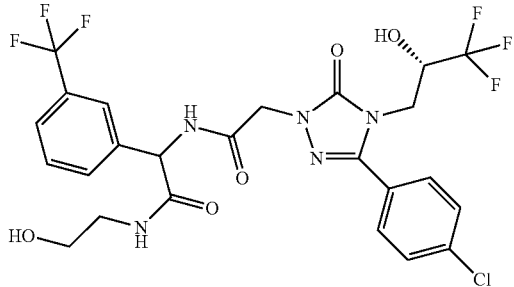 [SMILES: O=C(Cn1nc(-c2ccc(Cl)cc2)n(C[C@H](O)C(F)(F)F)c1=O)NC(C(=O)NCCO)c1cccc(C(F)(F)F)c1]

First-eluting diastereomer (11 mg) from the chromatographic diastereomer separation according to Method 10 of 37 mg of the compound of Example 49.

Chiral analytical HPLC [Method 11]: $R_t$=2.32 min

LC-MS [Method 4]: $R_t$=2.29 min; MS [ESIpos]: m/z=610 (M+H)$^+$ $^1$H-NMR (400 MHz, DMSO-d$_6$): δ [ppm]=3.01-3.12 (m, 1H), 3.14-3.25 (m, 1H), 3.36-3.43 (m, 2H), 3.82 (dd, 1H), 3.96 (dd, 1H), 4.20-4.32 (m, 1H), 4.53-4.66 (m [AB], 2H), 4.72 (t, 1H), 5.61 (d, 1H), 6.90 (s, 1H), 7.56-7.69 (m, 4H), 7.70-7.77 (m, 3H), 7.80 (s, 1H), 8.54 (t, 1H), 9.04 (d, 1H).

Example 51

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethyl)phenyl]acetamide (diastereomer 2)

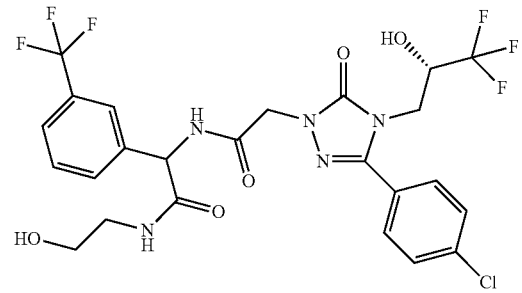 [SMILES: O=C(Cn1nc(-c2ccc(Cl)cc2)n(C[C@H](O)C(F)(F)F)c1=O)NC(C(=O)NCCO)c1cccc(C(F)(F)F)c1]

Last-eluting diastereomer (13 mg) from the chromatographic diastereomer separation according to Method 10 of 37 mg of the compound of Example 49.

Chiral analytical HPLC [Method 11]: $R_t$=4.01 min

LC-MS [Method 3]: $R_t$=1.16 min; MS [ESIpos]: m/z=610 (M+H)$^+$ $^1$H-NMR (400 MHz, DMSO-d$_6$): δ [ppm]=3.01-3.11 (m, 1H), 3.15-3.25 (m, 1H), 3.35-3.44 (m, 2H), 3.82 (dd, 1H), 3.96 (dd, 1H), 4.20-4.33 (m, 1H), 4.52-4.66 (m [AB], 2H), 4.71 (t, 1H), 5.61 (d, 1H), 6.88 (d, 1H), 7.55-7.69 (m, 4H), 7.70-7.77 (m, 3H), 7.80 (s, 1H), 8.54 (t, 1H), 9.04 (d, 1H).

Example 52

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-2-[3-(trifluoromethoxy)phenyl]acetamide (diastereomer mixture)

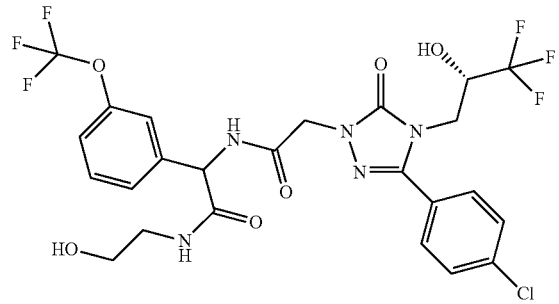 [SMILES: O=C(Cn1nc(-c2ccc(Cl)cc2)n(C[C@H](O)C(F)(F)F)c1=O)NC(C(=O)NCCO)c1cccc(OC(F)(F)F)c1]

Analogously to Example 1 (reaction time: overnight), 40 mg (0.11 mmol) of the compound of Example 8A and 38 mg (0.12 mmol) of the compound of Example 55A were used to prepare the title compound. This gave 64 mg (93% of theory) as a diastereomer mixture.

LC-MS [Method 3]: $R_t$=1.20 min; MS [ESIpos]: m/z=626 (M+H)$^+$ $^1$H-NMR (400 MHz, DMSO-d$_6$): δ [ppm]=3.02-3.12 (m, 1H), 3.14-3.24 (m, 1H), 3.34-3.43 (m, 2H), 3.82 (dd, 1H), 3.96 (dd, 1H), 4.20-4.33 (m, 1H), 4.53-4.65 (m [AB], 2H), 4.72 (t, 1H), 5.57 (d, 1H), 6.90 (dd, 1H, interpreted as 1 d each (6.889 and 6.904) per diastereomer), 7.29 (d, 1H), 7.42 (s, 1H), 7.44-7.52 (m, 2H), 7.62 (d, 2H), 7.71-7.78 (m, 2H), 8.54 (t, 1H), 9.00 (d, 1H).

Example 53

(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[2-(trifluoromethyl)phenyl]propanamide

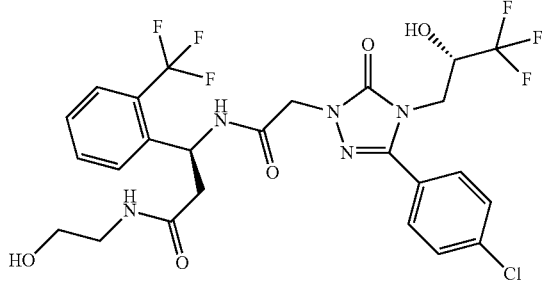 [SMILES: O=C(C[C@H](NC(=O)Cn1nc(-c2ccc(Cl)cc2)n(C[C@H](O)C(F)(F)F)c1=O)c1ccccc1C(F)(F)F)NCCO]

Analogously to Example 46, 35 mg (96 μmol) of the compound of Example 8A and 36 mg (115 μmol) of the compound of Example 56A were used to prepare the title compound. This gave 25 mg (42% of theory).

LC-MS [Method 4]: $R_t$=2.18 min; MS [ESIpos]: m/z=624 (M+H)$^+$ $^1$H-NMR (400 MHz, DMSO-d$_6$): δ [ppm]=2.45 (dd, 1H), 2.58 (dd, 1H), 3.09 (q, 2H), 3.31-3.38 (m, 2H), 3.82 (dd, 1H), 3.96 (dd, 1H), 4.19-4.33 (m, 1H), 4.39-4.51 (m, 2H), 4.64 (t, 1H), 5.46-5.54 (m, 1H), 6.89 (d, 1H), 7.42-7.51 (m, 1H), 7.59-7.70 (m, 5H), 7.74 (d, 2H), 7.82 (t, 1H), 8.76 (d, 1H).

Example 54

(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-hydroxyethyl)-3-[3-(trifluoromethyl)phenyl]propanamide

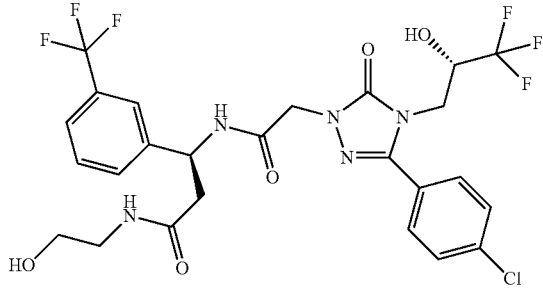 [SMILES: O=C(C[C@H](NC(=O)Cn1nc(-c2ccc(Cl)cc2)n(C[C@H](O)C(F)(F)F)c1=O)c1cccc(C(F)(F)F)c1)NCCO]

Analogously to Example 1, 74 mg (0.20 mmol) of the compound of Example 8A and 70 mg (0.22 mmol) of the compound of Example 57A were used to prepare the title compound. This gave 103 mg (81% of theory).

LC-MS [Method 3]: $R_t$=1.16 min; MS [ESIpos]: m/z=624 (M+H)$^+$.

$^1$H-NMR (400 MHz, DMSO-d$_6$): δ [ppm]=2.57-2.64 (m, 2H), 3.03 (q, 2H), 3.23-3.29 (m, 2H), 3.82 (dd, 1H), 3.96 (dd, 1H), 4.20-4.35 (m, 1H), 4.48 (s, 2H), 4.57-4.63 (m, 1H), 5.27 (q, 1H), 6.89 (br. s., 1H), 7.51-7.66 (m, 6H), 7.70-7.78 (m, 2H), 7.93 (t, 1H), 8.81 (d, 1H).

Example 55

(3S)-3-({[3-(4-Chlorophenyl)-4-cyclopropyl-5-oxo-4,5-dihydro-1H-1,2,4-triazol-1-yl]acetyl}-amino)-N-(2-hydroxyethyl)-3-[2-(trifluoromethyl)phenyl]propanamide

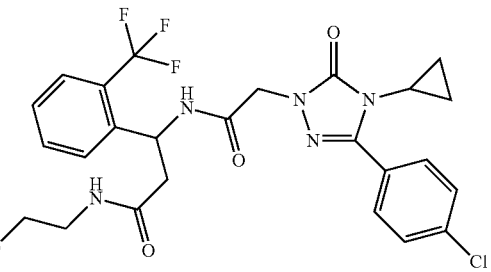

Analogously to Example 46, 50 mg (0.17 mmol) of [3-(4-chlorophenyl)-4-cyclopropyl-5-oxo-4,5-dihydro-1H-1,2,4-triazol-1-yl]acetic acid (for the preparation, see WO 2007/134862, Example 88A) and 64 mg (0.20 mmol) of the compound of Example 56A were used to prepare the title compound. This gave 43 mg (46% of theory).

LC-MS [Method 4: $R_t$=1.99; MS [ESIpos]: m/z=552 (M+H)$^+$.

$^1$H-NMR (400 MHz, DMSO-d$_6$): δ [ppm]=0.50-0.66 (m, 2H), 0.81-0.95 (m, 2H), 2.43 (dd, 1H), 2.54-2.60 (m, 1H), 3.07 (q, 2H), 3.16 (tt, 1H), 3.28-3.38 (m, 2H), 4.32-4.43 (m [AB], 2H), 4.63 (t, 1H), 5.41-5.52 (m, 1H), 7.41-7.50 (m, 1H), 7.55-7.70 (m, 5H), 7.76-7.86 (m, 3H), 8.76 (d, 1H).

Example 56

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-2-[2-(trifluoromethyl)phenyl]acetamide (diastereomer mixture)

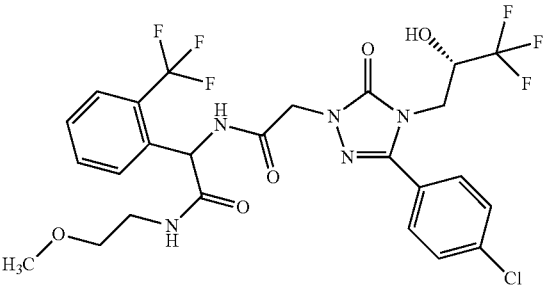 [SMILES: COCCNC(=O)C(NC(=O)Cn1nc(-c2ccc(Cl)cc2)n(C[C@H](O)C(F)(F)F)c1=O)c1ccccc1C(F)(F)F]

Analogously to Example 46, 30 mg (82 μmol) of the compound of Example 8A and 31 mg (98 μmol) of the compound of Example 53A were used to prepare the title compound. This gave 42 mg (82% of theory).

LC-MS [Method 1]: $R_t$=1.93 min; MS [ESIpos]: m/z=624 (M+H)$^+$ $^1$H-NMR (400 MHz, DMSO-d$_6$): δ [ppm]=3.23 (d, 3H, interpreted as 1 s each per diastereomer), 3.20-3.29 (m, 2H), 3.29-3.40 (m, 2H), 3.82 (dd, 1H), 3.96 (dd, 1H), 4.20-4.34 (m, 1H), 4.47 (dd, 1H), 4.62 (dd, 1H), 5.69 (dd, 1H, interpreted as 1 d each per diastereomer), 6.91 (dd, 1H, interpreted as 1 d each per diastereomer), 7.55 (t, 1H), 7.59-7.66 (m, 3H), 7.67-7.79 (m, 4H), 8.27 (t, 1H), 9.04 (dd, 1H, interpreted as 1 d each per diastereomer).

Example 57

(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[3-(trifluoromethyl)phenyl]propanamide

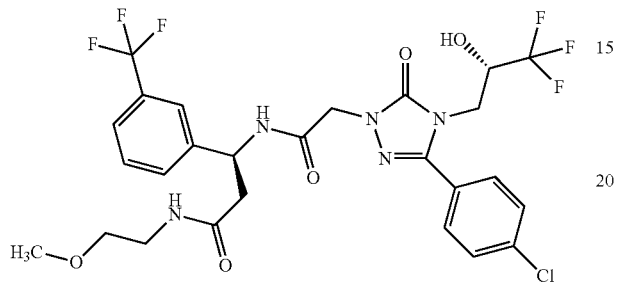

Analogously to Example 46, 50 mg (0.14 mmol) of the compound of Example 8A and 54 mg (0.16 mmol) of the compound of Example 59A were used to prepare the title compound. This gave 77 mg (88% of theory).

LC-MS [Method 3]: $R_t$=1.25 min; MS [ESIpos]: m/z=638 (M+H)$^+$ $^1$H-NMR (400 MHz, DMSO-d$_6$): δ [ppm]=2.57-2.65 (m, 2H), 3.04-3.24 (m, 4H), 3.15 (s, 3H), 3.82 (dd, 1H), 3.96 (dd, 1H), 4.21-4.34 (m, 1H), 4.48 (s, 2H), 5.23-5.32 (m, 1H), 6.89 (d, 1H), 7.51-7.65 (m, 6H), 7.71-7.79 (m, 2H), 8.01 (t, 1H), 8.82 (d, 1H).

Example 58

(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-(2-methoxyethyl)-3-[2-(trifluoromethyl)phenyl]propanamide

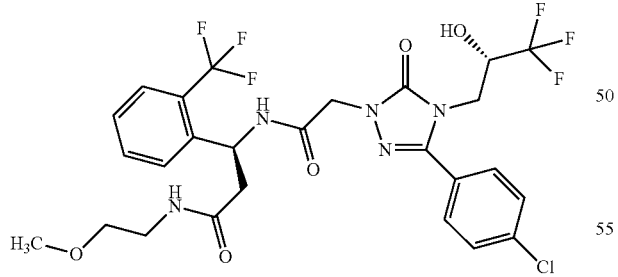

Analogously to Example 46, 35 mg (96 μmol) of the compound of Example 8A and 38 mg (115 μmol) of the compound of Example 58A were used to prepare the title compound. This gave 53 mg (87% of theory).

LC-MS [Method 4]: $R_t$=2.37 min; MS [ESIpos]: m/z=638 (M+H)$^+$ $^1$H-NMR (400 MHz, DMSO-d$_6$): δ [ppm]=2.45 (dd, 1H), 2.58 (dd, 1H), 3.14-3.20 (m, 2H), 3.21 (s, 3H), 3.25-3.29 (m, 2H), 3.82 (dd, 1H), 3.96 (dd, 1H), 4.21-4.32 (m, 1H), 4.44 (s, 2H), 5.45-5.55 (m, 1H), 6.89 (d, 1H), 7.44-7.50 (m, 1H), 7.59-7.70 (m, 5H), 7.72-7.77 (m, 2H), 7.90 (t, 1H), 8.77 (d, 1H).

Example 59

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-[2-(trifluoromethoxy)ethyl]-2-[3-(trifluoromethyl)phenyl]acetamide (diastereomer 1)

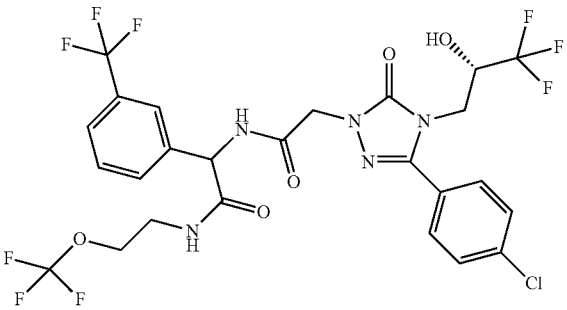 [SMILES: O=C(Cn1nc(-c2ccc(Cl)cc2)n(C[C@H](O)C(F)(F)F)c1=O)NC(C(=O)NCCOC(F)(F)F)c1cccc(C(F)(F)F)c1]

Analogously to Example 1, 37 mg (0.10 mmol) of the compound of Example 8A and 45 mg (0.12 mmol) of the compound of Example 60A were used to prepare the title compound. This gave 61 mg (88% of theory).

LC-MS [Method 1]: $R_t$=2.26 min; MS [ESIpos]: m/z=678 (M+H)$^+$ $^1$H-NMR (400 MHz, DMSO-d$_6$): δ [ppm]=3.30-3.40 (m, 1H), 3.40-3.51 (m, 1H), 3.82 (dd, 1H), 3.96 (dd, 1H), 3.98-4.07 (m, 2H), 4.20-4.32 (m, 1H), 4.54-4.65 (m [AB], 2H), 5.60 (d, 1H), 6.90 (d, 1H), 7.56-7.64 (m, 3H), 7.65-7.69 (m, 1H), 7.70-7.77 (m, 3H), 7.78 (br. s, 1H), 8.76 (t, 1H), 9.08 (d, 1H).

Example 60

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-N-[2-(trifluoromethoxy)ethyl]-2-[3-(trifluoromethyl)phenyl]acetamide (diastereomer 2)

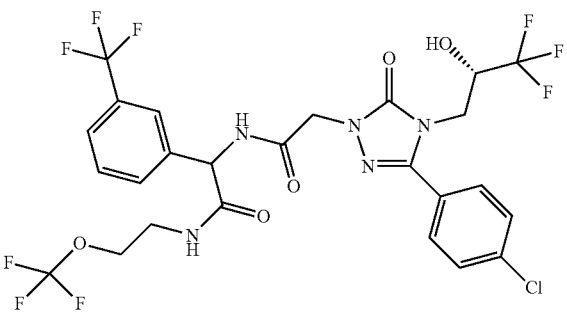 [SMILES: O=C(Cn1nc(-c2ccc(Cl)cc2)n(C[C@H](O)C(F)(F)F)c1=O)NC(C(=O)NCCOC(F)(F)F)c1cccc(C(F)(F)F)c1]

Analogously to Example 1, 50 mg (0.14 mmol) of the compound of Example 8A and 60 mg (0.16 mmol) of the compound of Example 61A were used to prepare the title compound. This gave 73 mg (79% of theory)

LC-MS [Method 1]: $R_t$=2.26 min; MS [ESIpos]: m/z=678 (M+H)$^+$ $^1$H-NMR (400 MHz, DMSO-d$_6$): δ [ppm]=3.31-3.40 (m, 1H), 3.40-3.50 (m, 1H), 3.82 (dd, 1H), 3.96 (dd, 1H), 3.97-4.07 (m, 2H), 4.19-4.35 (m, 1H), 4.52-4.68 (m [AB], 2H), 5.60 (d, 1H), 6.88 (d, 1H), 7.56-7.65 (m, 3H), 7.65-7.69 (m, 1H), 7.70-7.76 (m, 3H), 7.79 (s, 1H), 8.76 (t, 1H), 9.08 (d, 1H).

B. EVALUATION OF THE PHARMACOLOGICAL ACTIVITY

Abbreviations

EDTA ethylenediaminetetraacetic acid
DMEM Dulbecco's Modified Eagle Medium
FCS foetal calf serum
HEPES 4-(2-hydroxyethyl)-1-piperazineethanesulphonic acid
SmGM Smooth Muscle Cell Growth Media
Tris-HCl 2-amino-2-(hydroxymethyl)-1,3-propanediol hydrochloride
UtSMC Uterine Smooth Muscle Cells The pharmacological action of the compounds according to the invention can be shown in the following assays:

B-1. Cellular In Vitro Assay for Determining the Vasopressin Receptor Activity

The identification of agonists and antagonists of the V1a and V2 vasopressin receptors from humans and rats and also the quantification of the activity of the substances described here takes place using recombinant cell lines. These cells derive originally from a hamster's ovary epithelial cell (Chinese Hamster Ovary, CHO K1, ATCC: American Type Culture Collection, Manassas, Va. 20108, USA). The test cell lines constitutively express a modified form of the calcium-sensitive photoprotein aequorin, which, after reconstitution with the cofactor coelenterazine, emits light when there are increases in the free calcium concentration (Rizzuto R., Simpson A. W., Brini M., Pozzan T.; *Nature* 358 (1992) 325-327). In addition, the cells are stably transfected with the human or rat V1a or V2 receptors. In the case of the Gs-coupling V2 receptors, the cells are stably transfected with a further gene, which codes for the promiscuous $G_{\alpha 16}$ protein (Amatruda T. T., Steele D. A., Slepak V. Z., Simon M A., *Proc. Na. Acad. Sci. USA* 88 (1991), 5587-5591), either independently or as a fusion gene. The resulting vasopressin receptor test cells react to stimulation of the recombinantly expressed vasopressin receptors by intracellular release of calcium ions, which can be quantified by the resulting aequorin luminescence using a suitable luminometer (Milligan G., Marshall F., Rees S., *Trends in Pharmaco. Sci.* 17 (1996) 235-237).

Test Procedure:

On the day before the assay, the cells are plated out in culture medium (DMEM, 10% FCS, 2 mM glutamine, 10 mM HEPES) in 384-well microtiter plates and kept in a cell incubator (96% atmospheric humidity, 5% v/v carbon dioxide, 37° C.). On the day of the assay, the culture medium is replaced by a Tyrode solution (140 mM sodium chloride, 5 mM potassium chloride, 1 mM magnesium chloride, 2 mM calcium chloride, 20 mM glucose, 20 mM HEPES), which additionally contains the cofactor coelenterazine (50 µM), and the microtiter plate is then incubated for a further 3-4 hours. The test substances in various concentrations are placed for 10 to 20 minutes in the wells of the microtiter plate before the agonist [Arg8]-vasopressin is added, and the resulting light signal is measured immediately in the luminometer. The $IC_{50}$ values are calculated using the GraphPad PRISM computer program (Version 3.02).

Table A below lists representative $IC_{50}$ values for the compounds according to the invention transfected with the human V1a or V2 receptor:

TABLE A

| Example No. | $IC_{50}$ hV1a [µM] | $IC_{50}$ hV2 [µM] |
| --- | --- | --- |
| 1 | 0.0092 | 0.058 |
| 3 | 0.554 | 0.467 |
| 4 | 0.0019 | 0.0041 |
| 5 | 0.042 | 1.17 |
| 6 | 0.047 | 0.324 |
| 10 | 0.15 | 0.96 |
| 11 | 0.028 | 0.497 |
| 12 | 0.024 | 0.182 |
| 14 | 0.053 | 0.009 |
| 15 | 0.012 | 0.31 |
| 16 | 0.524 | 0.262 |
| 17 | 1.42 | 0.022 |
| 18 | 0.0012 | 0.0019 |
| 19 | 0.0006 | 0.0011 |
| 20 | 0.0024 | 0.0045 |
| 21 | 0.0010 | 0.0008 |
| 22 | 0.0012 | 0.0027 |
| 25 | 0.502 | 0.282 |
| 26 | 0.0017 | 0.0023 |
| 28 | 1.38 | 0.346 |
| 29 | 0.0010 | 0.0033 |
| 31 | 0.0078 | 1.18 |
| 32 | 0.0071 | 1.27 |
| 33 | 0.017 | 1.05 |
| 35 | 0.0089 | 0.655 |
| 36 | 0.0882 | 0.78 |
| 38 | 0.0328 | 0.0386 |
| 39 | 0.0049 | 0.0008 |
| 40 | 0.0111 | 0.0081 |
| 41 | 0.0015 | 0.0036 |
| 42 | 0.038 | 0.158 |
| 43 | 0.060 | 1.60 |
| 49 | 0.0022 | 0.0076 |
| 52 | 0.0097 | 0.042 |
| 53 | 0.0009 | 0.0026 |
| 54 | 0.0038 | 0.0026 |
| 55 | 0.0060 | 0.569 |
| 56 | 0.0030 | 0.144 |
| 57 | 0.0145 | 0.0074 |
| 58 | 0.0035 | 0.136 |
| 59 | 0.136 | 0.061 |
| 60 | 0.0030 | 0.0197 |

B-2. Cellular In Vitro Assay for Detecting the Action of Vasopressin V1a Receptor Antagonists on the Regulation of Pro-Fibrotic Genes The cell line H9C2 described as a cardiomyocyte type (American Type Culture Collection ATCC No. CRL-1446), isolated from rat cardiac tissue, endogenously expresses the vasopressin VIA receptor AVPR1A in high copy number, whereas the AVPR2 expression cannot be detected. For cell assays for the inhibition of the AVPR1A receptor-dependent regulation of gene expression by receptor antagonists, the procedure is as follows:

H9C2 cells are seeded in 12-well microtiter plates for cell culture, at a cell density of 100 000 cells/well, in 1.0 ml of Opti-MEM medium (Invitrogen Corp., Carlsbad Calif., USA, Cat. No. 11058-021) with 2% FCS and 1% penicillin/streptomycin solution (Invitrogen, Cat. No. 10378-016), and held in a cell incubator (96% atmospheric humidity, 5% v/v carbon dioxide, 37° C.). After 24 hours, sets of three wells (triplicate) are charged with vehicle solution (negative control), vasopressin solution ([Arg[8]]-vasopressin acetate, Sigma, Cat. No. V9879) or test substances (dissolved in vehicle: water with 20% by volume ethanol) and vasopressin solution. In the cell culture, the final vasopressin concentration is 0.05 µM. The test substance solution is added to the cell culture in small volumes, and so a final concentration of 0.1% of ethanol in the cell assay is not exceeded. After an incubation time of 6 hours, the culture supernatant is drawn off under suction, the adherent cells are lysed in 250 µl of RLT buffer (Qiagen, Ratingen, Cat. No. 79216), and the RNA is isolated from this lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and RTPCR (pPCR MasterMix RT-QP2X-03-075 from Eurogentec, Seraing, Belgium). All procedures take place in accordance with the working protocols of the test reagents' manufacturers. The primer sets for the RTPCR are selected on the basis of the mRNA gene sequences (NCBI Genbank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 96-well or 384-well microtiter plate format in accordance with the instrument operating instructions. The relative gene expression is represented by the delta-delta Ct value [Applied Biosystems, User Bulletin No. 2 ABI Prism 7700 SDS Dec. 11, 1997 (updated 10/2001)] with reference to the level of expression of the ribosomal protein L-32 gene (Genbank Acc. No. NM_013226) and the threshold Ct value of Ct=35.

B-3. In Vivo Assay for Detecting the Cardiovascular Effect: Blood Pressure Measurement on Anaesthetized Rats (Vasopressin 'Challenge' Model)

In male Sprague-Dawley rats (250-350 g body weight) under ketamine/xylazine/pentobarbital injection anaesthesia, polyethylene tubes (PE-50; Intramedic®), which are prefilled with heparin-containing (500 IU/ml) isotonic sodium chloride solution, are introduced into the jugular vein and the femoral vein and then tied in. Via one venous access, with the aid of a syringe, argininevasopressin is injected; the test substances are administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment the experimental animal is administered 3-4 successive bolus injections at intervals of 10-15 min with a defined amount of arginineva-sopressin (30 ng/kg) in isotonic sodium chloride solution and, when the blood pressure has reached initial levels again, the substance under test is administered as a bolus, with subsequent ongoing infusion, in a suitable solvent. After this, at defined intervals (10-15 min), the same amount of vasopressin as at the start is administered again. On the basis of the blood pressure values, a determination is made of the extent to which the test substance counteracts the hypertensive effect of the vasopressin. Control animals receive only solvent instead of the test substance.

Following intravenous administration, the compounds of the invention, in comparison to the solvent controls, bring about an inhibition in the blood pressure increase caused by arginine-vasopressin.

B-4. In Vivo Assay for Detecting the Cardiovascular Effect: Diuresis Investigations on Conscious Rats in Metabolism Cages Wistar rats (220-400 g body weight) are kept with free access to feed (Altromin) and drinking water. During the experiment, the animals are kept with free access to drinking water for 4 to 8 hours individually in metabolism cages suitable for rats of this weight class (Tecniplast Deutschland GmbH, D-82383 Hohenpeißenberg). At the beginning of the experiment, the animals are administered the substance under test in a volume of 1 to 3 ml/kg body weight of a suitable solvent by means of gavage into the stomach. Control animals receive only solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per unit time is determined separately for each animal, and the concentration of the sodium and potassium ions excreted in the urine is measured by standard methods of flame photometry. To obtain a sufficient volume of urine, the animals are given a defined amount of water by gavage at the beginning of the experiment (typically 10 ml per kilogram of body weight). Before the beginning of the experiment and after the end of the experiment, the body weight of the individual animals is determined.

Following oral administration, in comparison with control animals, the compounds of the invention bring about an increased excretion of urine, which is based essentially on an increased excretion of water (aquaresis).

B-5. In Vivo Assay for Detecting the Cardiovascular Effect: Haemodynamic Investigations on Anaesthetized Dogs Male or female mongrel dogs (Mongrels, Marshall BioResources, USA) with a weight of between 20 and 30 kg are anaesthetized with pentobarbital (30 mg/kg iv, Narcoren®, Merial, Germany) for the surgical interventions and the haemodynamic and functional investigation termini. Alcuronium chloride (Alloferin®, ICN Pharmaceuticals, Germany, 3 mg/animal iv) serves additionally as a muscle relaxant. The dogs are intubated and ventilated with an oxygen/ambient air mixture (40/60%), about 5-6 L/min) Ventilation takes place using a ventilator from Draeger (Sulla 808) and is monitored using a carbon dioxide analyser (Engström).

The anaesthesia is maintained by continual infusion of pentobarbital (50 μag/kg/min); fentanyl is used as an analgesic (10 μg/kg/h). One alternative to pentobarbital is to use isoflurane (1-2% by volume).

In preparatory interventions, the dogs are fitted with a cardiac pacemaker.

At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with illumination, into the right ventricle.

At the same time as the implanting of the pacemaker, through retrograde advancing of 7F biopsy forceps (Cordis) via a sheath introducer (Avanti+®; Cordis) in the fermoral artery, and after atraumatic passage through the aortic valve, there is defined lesion of the mitral valve, with monitoring by echocardiography and illumination. Thereafter all of the accesses are removed and the dog wakes spontaneously from the anaesthesia.

After a further 7 days (i.e. 14 days before the first drug testing), the above-described pacemaker is activated and the heart is stimulated at a frequency of 220 beats per minute.

The actual drug testing experiments take place 14 and 28 days after the beginning of pacemaker stimulation, using the following instrumentation:

Introduction of a bladder catheter for bladder relief and for measuring the flow of urine Attachment of ECG leads to the extremities (for ECG measurement)

Introduction of a Fluidmedic PE-300 tube filled with sodium chloride solution into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through the left atrium or through a port secured in the carotid artery, for measuring cardiac haemodynamics Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure Siting of a venous catheter in the cephalic vein, for infusing pentobarbital, for liquid replacement and for blood sampling (determination of the plasma levels of substance or other clinical blood values)

Siting of a venous catheter in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (Gould amplifier, Gould Instrument Systems, Valley View, USA or Edwards-Vigilance-Monitor, Edwards, Irvine, USA) and subsequently fed into the Ponemah system (DataSciences Inc, Minneapolis, USA) for evaluation. The signals are recorded continuously throughout the experimental period, and are further processed digitally by said software, and averaged over 30 seconds.

B-6. Determination of the Solubility

Reagents Required:

PBS buffer pH 6.5: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1N hydrochloric acid (for example from Merck, Art. No. 1.09057.1000) the pH is then adjusted to 6.5.

PEG/water solution (30:70 v/v): 30 ml of polyethylene glycol 400 (for example from Merck, Art. No. 8.17003.1000) and 70 ml of distilled water are homogenized in a 100 ml measuring flask.

PEG/PBS buffer pH 6.5 (80:20 v/v): 80 ml of polyethylene glycol 400 (for example from Merck, Art. No. 8.17003.1000) and 20 ml of PBS buffer pH 6.5 are homogenized in a 100 ml measuring flask.

Dimethyl sulphoxide (for example from Baker, Art. No. 7157.2500)

Distilled water.

Preparation of the Starting Solution (Original Solution):

At least 4 mg of the test substance are weighed accurately into a wide-necked 10 mm screw V vial (from Glastechnik Gräfenroda GmbH, Art. No. 8004-WM-H/V150 with fitting screw cap and septum, in a pipetting robot DMSO is added to a concentration of 50 mg/ml and the mixture is shaken for 10 minutes.

Preparation of the Calibration Solutions:

Preparation of the starting solution for calibration solutions (stock solution): With the aid of a pipetting robot, 10 µl of the original solution are transferred into a microtiter plate and made up with DMSO to a concentration of 600 µg/ml. The sample is shaken until everything has gone into solution.

Calibration solution 1 (20 µg/ml): 1000 µl of DMSO are added to 34.4 µl of the stock solution, and the mixture is homogenized.

Calibration solution 2 (2.5 µg/ml): 700 µl of DMSO are added to 100 µl of calibration solution 1, and the mixture is homogenized.

Preparation of the Sample Solutions:

Sample solution for solubilities of up to 5 g/liter in PBS buffer pH 6.5: 10 µl of the original solution are transferred into a microtiter plate, and 1000 µl of PBS buffer pH 6.5 are added.

Sample solution for solubilities of up to 5 g/liter in PEG/water (30:70): 10 µl of the original solution are transferred into a microtiter plate, and 1000 µl of PEG/water (30:70) are added.

Sample solution for solubilities of up to 5 g/liter in PEG/PBS buffer pH 6.5 (80:20): 10 µl of the original solution are transferred into a microtiter plate, and 1000 µl of PEG/PBS buffer pH 6.5 (80:20) are added.

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 µl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 µl of the supernatant are removed and diluted 1:5 and 1:100 with DMSO. From each dilution, a sample is transferred into a vessel suitable for HPLC analysis.

Analysis:

The samples are analysed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 µg/ml; 3) sample solution 1:5; 4) sample solution 1:100.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

Representative solubilities of the compounds of the formula (I) according to the invention are shown in Table B below.

TABLE B

| Example | Solubility [mg/l] PBS buffer pH 6.5 |
|---------|-------------------------------------|
| 6       | 340                                 |
| 10      | 360                                 |
| 21      | 360                                 |
| 31      | 110                                 |
| 52      | 100                                 |
| 54      | 400                                 |

C. EXEMPLARY EMBODIMENTS OF PHARMACEUTICAL COMPOSITIONS

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

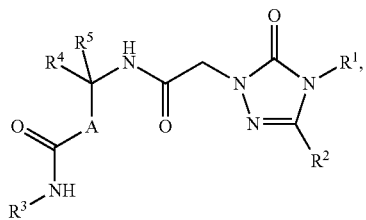

in which
A represents a bond or —C(R$^{6A}$R$^{6B}$)—,
where
R$^{6A}$ represents hydrogen, (C$_1$-C$_4$)-alkyl or trifluoromethyl,
R$^{6B}$ represents hydrogen or (C$_1$-C$_4$)-alkyl,
R$^1$ represents (C$_1$-C$_6$)-alkyl, (C$_2$-C$_6$)-alkenyl, (C$_2$-C$_6$)-alkynyl or (C$_3$-C$_7$)-cycloalkyl, where (C$_1$-C$_6$)-alkyl, (C$_2$-C$_6$)-alkenyl and (C$_2$-C$_6$)-alkynyl may be substituted by 1 to 3 substituents independently of one another selected from the group consisting of deuterium, halogen, cyano, oxo, hydroxy, trifluoromethyl, (C$_3$-C$_7$)-cycloalkyl, (C$_1$-C$_6$)-alkoxy, trifluoromethoxy and phenyl,
in which (C$_3$-C$_7$)-cycloalkyl may be substituted by 1 or 2 substituents independently of one another selected from the group consisting of (C$_1$-C$_4$)-alkyl, oxo, hydroxy, (C$_1$-C$_4$)-alkoxy and amino,
and
in which (C$_1$-C$_6$)-alkoxy may be substituted by 1 or 2 substituents independently of one another selected from the group consisting of amino, hydroxy, (C$_1$-C$_4$)-alkoxy, hydroxycarbonyl and (C$_1$-C$_4$)-alkoxycarbonyl
and
in which phenyl may be substituted by 1 to 3 substituents independently of one another selected from the group consisting of halogen, cyano, nitro, (C$_1$-C$_4$)-alkyl, trifluoromethyl, hydroxy, hydroxymethyl, (C$_1$-C$_4$)-alkoxy, trifluoromethoxy, (C$_1$-C$_4$)-alkoxymethyl, hydroxycarbonyl, (C1-C$_4$)-alkoxycarbonyl, aminocarbonyl, mono-(C$_1$-C$_4$)-alkylaminocarbonyl and di-(C$_1$-C$_4$)-alkylaminocarbonyl,
and
where (C$_3$-C$_7$)-cycloalkyl may be substituted by 1 or 2 substituents independently of one another selected from the group consisting of fluorine, (C$_1$-C$_4$)-alkyl, (C$_1$-C$_4$)-alkoxy, hydroxy, amino and oxo,
R$^2$ represents benzothienyl, phenyl, thienyl or furyl,
where benzothienyl, phenyl, thienyl and furyl may be substituted by 1 to 3 substituents independently of one another selected from the group consisting of halogen, cyano, nitro, (C$_1$-C$_4$)-alkyl, trifluoromethyl, hydroxy, (C$_1$-C$_4$)-alkoxy and trifluoromethoxy,
R$^3$ represents a group of the formula

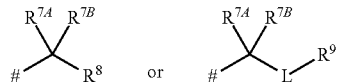

where
# represents the point of attachment to the nitrogen atom,
L represents (C$_1$-C$_4$)-alkanediyl,
where (C$_1$-C$_4$)-alkanediyl may be substituted by 1 to 3 substituents independently of one another selected from the group consisting of fluorine and (C$_1$-C$_4$)-alkyl,
R$^{7A}$ represents hydrogen or (C$_1$-C$_4$)-alkyl,
R$^{7B}$ represents hydrogen or (C$_1$-C$_4$)-alkyl,
or
R$^{7A}$ and R$^{7B}$ together with the carbon atom to which they are attached form a 3- to 6-membered carbocycle,
R$^8$ represents hydroxycarbonyl, (C$_1$-C$_4$)-alkoxycarbonyl, aminocarbonyl, mono-(C$_1$-C$_4$)-alkylaminocarbonyl or di-(C$_1$-C$_4$)-alkylaminocarbonyl,
R$^9$ represents hydroxy, trifluoromethoxy, (C$_1$-C$_4$)-alkoxy, hydroxycarbonyl, (C$_1$-C$_4$)-alkoxycarbonyl, aminocarbonyl, mono-(C$_1$-C$_4$)-alkylaminocarbonyl or di-(C$_1$-C$_4$)-alkylaminocarbonyl,
R$^4$ represents phenyl, naphthyl or 5- to 10-membered heteroaryl,
where phenyl, naphthyl and 5- to 10-membered heteroaryl may be substituted by 1 to 3 substituents independently of one another selected from the group consisting of halogen, cyano, nitro, (C$_1$-C$_4$)-alkyl, difluoromethyl, trifluoromethyl, hydroxy, $(C_1-C_4)$-alkoxy, difluoromethoxy and trifluoromethoxy, $R^5$ represents hydrogen, deuterium, trifluoromethyl or $(C_1-C_4)$-alkyl, and its salts, solvates and solvates of the salts.

2. The compound of claim 1, in which

A represents a bond or —C($R^{6A}R^{6B}$)—,
where
$R^{6A}$ represents hydrogen,
$R^{6B}$ represents hydrogen, $R^1$ represents $(C_1-C_6)$-alkyl, $(C_2-C_6)$-alkenyl or $(C_3-C_6)$-cycloalkyl,
where $(C_1-C_6)$-alkyl and $(C_2-C_6)$-alkenyl may be substituted by 1 to 3 substituents independently of one another selected from the group consisting of fluorine, chlorine, cyano, oxo, hydroxy, trifluoromethyl, $(C_3-C_6)$-cycloalkyl, $(C_1-C_4)$-alkoxy, trifluoromethoxy and phenyl,
in which $(C_3-C_6)$-cycloalkyl may be substituted by 1 or 2 substituents independently of one another selected from the group consisting of methyl, ethyl, oxo, hydroxy, methoxy, ethoxy and amino,
and
in which phenyl may be substituted by a substituent selected from the group consisting of fluorine, chlorine, cyano, methyl, ethyl, trifluoromethyl, methoxy, ethoxy, trifluoromethoxy, methoxymethyl, ethoxymethyl, hydroxycarbonyl, methoxycarbonyl, ethoxycarbonyl and aminocarbonyl,
and
where $(C_3-C_6)$-cycloalkyl may be substituted by 1 or 2 substituents independently of one another selected from the group consisting of fluorine, methyl, ethyl, methoxy, ethoxy, hydroxy, amino and oxo, $R^2$ represents phenyl or thienyl,
where phenyl and thienyl may be substituted by 1 or 2 substituents independently of one another selected from the group consisting of fluorine, chlorine, bromine, methyl, ethyl, trifluoromethyl, hydroxy, methoxy, ethoxy and trifluoromethoxy, $R^3$ represents a group of the formula

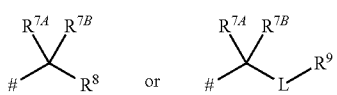

where
# represents the point of attachment to the nitrogen atom,
L represents methylene,
where methylene may be substituted by 1 or 2 methyl substituents,
$R^{7A}$ represents hydrogen or methyl,
$R^{7B}$ represents hydrogen or methyl,
or
$R^{7A}$ and $R^{7B}$ together with the carbon atom to which they are attached form a cyclopropyl ring,
$R^8$ represents hydroxycarbonyl, methoxycarbonyl, ethoxycarbonyl, aminocarbonyl, methylaminocarbonyl, ethylaminocarbonyl, dimethylaminocarbonyl or diethylaminocarbonyl,
$R^9$ represents hydroxy, trifluoromethoxy, methoxy, ethoxy, hydroxycarbonyl, methoxycarbonyl, ethoxycarbonyl, aminocarbonyl, methylaminocarbonyl, ethylaminocarbonyl, dimethylaminocarbonyl or diethylaminocarbonyl, $R^4$ represents phenyl,
where phenyl is substituted by 1 to 3 substituents independently of one another selected from the group consisting of fluorine, chlorine, cyano, methyl, ethyl, difluoromethyl, trifluoromethyl, methoxy, difluoromethoxy and trifluoromethoxy, $R^5$ represents hydrogen or methyl,
and its salts, solvates and solvates of the salts.

3. The compound of claim 1, in which

A represents a bond or —C($R^{6A}R^{6B}$)—,
where
$R^{6A}$ represents hydrogen,
$R^{6B}$ represents hydrogen, $R^1$ represents $(C_2-C_4)$-alkyl, $(C_2-C_4)$-alkenyl or cyclopropyl, where $(C_2-C_4)$-alkyl and $(C_2-C_4)$-alkenyl may be substituted by 1 or 2 substituents independently of one another selected from the group consisting of fluorine, oxo, hydroxy and trifluoromethyl, $R^2$ represents phenyl,
where phenyl is substituted by a substituent selected from the group consisting of fluorine and chlorine, $R^3$ represents a group of the formula

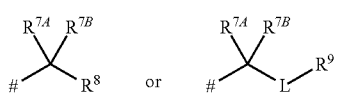

where
# represents the point of attachment to the nitrogen atom,
L represents methylene,
$R^{7A}$ represents hydrogen or methyl,
$R^{7B}$ represents hydrogen or methyl,
or
$R^{7A}$ and $R^{7B}$ together with the carbon atom to which they are attached form a cyclopropyl ring,
$R^8$ represents hydroxycarbonyl, methoxycarbonyl, ethoxycarbonyl or aminocarbonyl,
$R^9$ represents hydroxy, methoxy, hydroxycarbonyl, methoxycarbonyl, ethoxycarbonyl or aminocarbonyl, $R^4$ represents a group of the formula

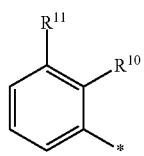

where
* represents the point of attachment to the group —C($R^5$)(AC(=O)NHR$^3$)—,
$R^{10}$ represents hydrogen, chlorine, trifluoromethyl, trifluoromethoxy or methoxy,
$R^{11}$ represents hydrogen, fluorine, chlorine, trifluoromethyl, trifluoromethoxy or methoxy,
where at least one of the radicals $R^{10}$ and $R^{11}$ is different from hydrogen, $R^5$ represents hydrogen or methyl,
and its salts, solvates and solvates of the salts.

4. A process for preparing compounds of the formula (I) as defined in claim 1, comprising:
[A] coupling a compound of the formula (II)

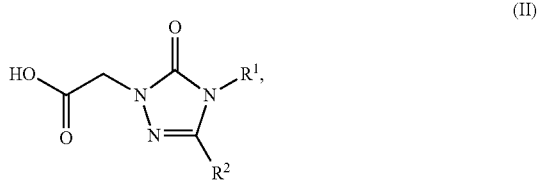

in which $R^1$ and $R^2$ each have the meanings given in claim 1,
in an inert solvent with activation of the carboxylic acid function with a compound of the formula (III)

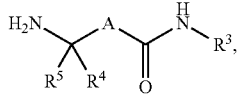
(III)

in which A, $R^3$, $R^4$ and $R^5$ each have the meanings given in claim 1,
or
[B] reacting a compound of the formula (IV)

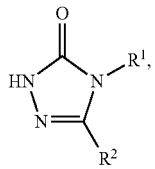
(IV)

in which $R^1$ and $R^2$ each have the meanings given in claim 1,
in an inert solvent in the presence of a base with a compound of the formula (V)

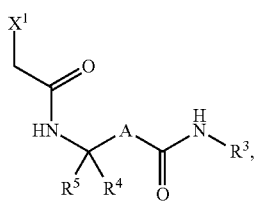
(V)

in which A, $R^3$, $R^4$ and $R^5$ each have the meanings given in claim 1
and
$X^1$ represents a leaving group, or
[C] coupling a compound of the formula (VI)

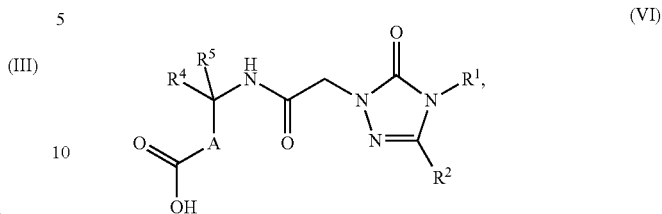
(VI)

in which A, $R^1$, $R^2$, $R^4$ and $R^5$ each have the meanings given in claim 1,
in an inert solvent with activation of the carboxylic acid function with a compound of the formula (VII)

$H_2N-R^3$ (VII), in which $R^3$ has the meaning given in claim 1,
and optionally converting the resulting compounds of formula (I) with the appropriate (i) solvents and/or (ii) acids or bases into their solvates, salts and/or solvates of the salts.

5. A pharmaceutical composition comprising a compound of claim 1 and an inert, non-toxic, pharmaceutically suitable auxiliary.

6. The pharmaceutical composition of claim 5, further comprising one or more active substances selected from the group consisting of diuretics, angiotensin AII antagonists, ACE inhibitors, beta-receptor blockers, mineralocorticoid receptor antagonists, organic nitrates, NO donors and positive-inotropic active substances.

7. A method for the treatment of acute and chronic heart failure, hypervolaemic and euvolaemic hyponatraemia, cirrhosis of the liver, ascites, oedema and the syndrome of inadequate ADH secretion (SIADH) comprising administering to a human or animal in need thereof an effective amount of at least one compound of claim 1.

8. A method for the treatment of acute and chronic heart failure, hypervolaemic and euvolaemic hyponatraemia, cirrhosis of the liver, ascites, oedema and the syndrome of inadequate ADH secretion (SIADH) comprising administering to a human or animal in need thereof an effective amount of at least one pharmaceutical composition of claim 5.

* * * * *